US012714682B2

(12) United States Patent
Gesell et al.

(10) Patent No.: US 12,714,682 B2
(45) Date of Patent: Aug. 25, 2026

(54) CALIXARENE COMPOUNDS AND USES THEREOF

(71) Applicant: UNIVERSITÄT WIEN, Vienna (AT)

(72) Inventors: Tanja Gesell, Vienna (AT); Robert Konrat, Vienna (AT); Marco Sealey Cardona, Vienna (AT)

(73) Assignee: Universität Wien, Vienna (AT)

(*) Notice: Subject to any disclaimer, the term of this patent is extended or adjusted under 35 U.S.C. 154(b) by 1046 days.

(21) Appl. No.: 17/620,301

(22) PCT Filed: Jun. 18, 2020

(86) PCT No.: PCT/EP2020/066991

§ 371 (c)(1),
(2) Date: Dec. 17, 2021

(87) PCT Pub. No.: WO2020/254507

PCT Pub. Date: Dec. 24, 2020

(65) Prior Publication Data

US 2022/0249411 A1 Aug. 11, 2022

(30) Foreign Application Priority Data

Jun. 18, 2019 (EP) .................................... 19181021

(51) Int. Cl.

| | |
|---|---|
| ***A61K 31/185*** | (2006.01) |
| ***A61K 9/00*** | (2006.01) |
| ***A61K 31/194*** | (2006.01) |
| ***A61K 31/403*** | (2006.01) |
| ***A61K 31/42*** | (2006.01) |
| ***A61K 31/44*** | (2006.01) |

(Continued)

(52) U.S. Cl.

CPC .......... *A61K 31/185* (2013.01); *A61K 9/0056* (2013.01); *A61K 31/194* (2013.01); *A61K 31/403* (2013.01); *A61K 31/42* (2013.01); *A61K 31/44* (2013.01); *A61K 31/4706* (2013.01); *A61K 31/4995* (2013.01); *A61K 31/519* (2013.01); *A61K 31/655* (2013.01); *A61K 38/13* (2013.01); *A61P 11/06* (2018.01); *A61P 17/06* (2018.01); *A61P 19/02* (2018.01); *A61P 29/00* (2018.01); *A61P 37/06* (2018.01); *A61P 39/06* (2018.01); *C07C 309/43* (2013.01); *C07D 209/70* (2013.01); *C07D 221/22* (2013.01); *C07D 471/08* (2013.01); *C07D 487/08* (2013.01)

(58) Field of Classification Search

CPC .. A61K 31/185; A61K 9/0056; A61K 31/194; A61K 31/403; A61K 31/42; A61K 31/44; A61K 31/4706; A61K 31/4995; A61K 31/519; A61K 31/655; A61K 38/13; A61P 39/06; A61P 17/06; A61P 11/06; A61P 37/06; A61P 19/02; A61P 29/00; C07C 309/43; C07D 209/70; C07D 221/22; C07D 471/08; C07D 487/08

See application file for complete search history.

(56) References Cited

U.S. PATENT DOCUMENTS 5,409,959 A 4/1995 Hwang et al.
5,441,983 A 8/1995 Hwang et al.

(Continued)

FOREIGN PATENT DOCUMENTS

CN 108329336 A1 7/2018
CN 108601758 A 9/2018

(Continued)

OTHER PUBLICATIONS

Sigma Millipore Heparin vs. Heparan Sulfate web page, accessed May 31, 2025. https://www.sigmaaldrich.com/US/en/technical-documents/technical-article/cell-culture-and-cell-culture-analysis/mammalian-cell-culture/what-is-heparin?srsltid=AfmBOoo2a7M31w-i-UMI9cACc96Hgz43j42InOkuHalwcDmL_OGBXopt (Year: 2025).*

(Continued)

*Primary Examiner* — Adam C Milligan
*Assistant Examiner* — William Y Lee
(74) *Attorney, Agent, or Firm* — Maier & Maier, PLLC

(57) ABSTRACT

Compounds of general Formula (I)

(I)

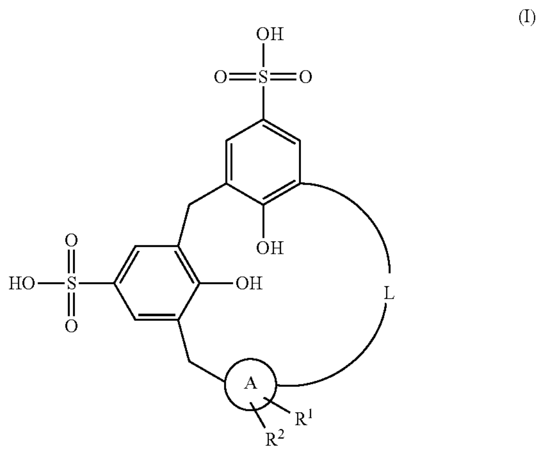

wherein the elements A, L, $R^1$ and $R^2$ have a defined meaning, and their medical and non-medical use. The compounds may be used treatment of a subject in need of any one or more of anti-inflammatory, anti-oxidative, anti-ageing, or lipid metabolism modulation therapy or prophylaxis. The compounds may also be used as food or feed products, dietary supplements or cosmetic preparations.

7 Claims, 28 Drawing Sheets

(51) Int. Cl.

| | |
|---|---|
| *A61K 31/4706* | (2006.01) |
| *A61K 31/4995* | (2006.01) |
| *A61K 31/519* | (2006.01) |
| *A61K 31/655* | (2006.01) |
| *A61K 38/13* | (2006.01) |
| *A61P 11/06* | (2006.01) |
| *A61P 17/06* | (2006.01) |
| *A61P 19/02* | (2006.01) |
| *A61P 29/00* | (2006.01) |
| *A61P 37/06* | (2006.01) |
| *A61P 39/06* | (2006.01) |
| *C07C 309/43* | (2006.01) |
| *C07D 209/70* | (2006.01) |
| *C07D 221/22* | (2006.01) |
| *C07D 471/08* | (2006.01) |
| *C07D 487/08* | (2006.01) |

(56) References Cited

U.S. PATENT DOCUMENTS

| | | | | |
|---|---|---|---|---|
| 5,489,612 | A | 2/1996 | Atwood et al. | |
| 11,179,358 | B2 * | 11/2021 | Konrat | A61P 25/28 |
| 2017/0052154 | A1 | 2/2017 | Hof et al. | |
| 2020/0360315 | A1 * | 11/2020 | Konrat | A61P 25/16 |

FOREIGN PATENT DOCUMENTS

| | | | |
|---|---|---|---|
| JP | 2007056055 | A | 3/2007 |
| JP | 2018535272 | A | 11/2018 |
| WO | 9403165 | A1 | 2/1994 |
| WO | 0007585 | A1 | 2/2000 |
| WO | 2017093363 | A1 | 6/2017 |

OTHER PUBLICATIONS

Mayo Clinic Progeria website accessed May 31, 2025. https://www.mayoclinic.org/diseases-conditions/progeria/symptoms-causes/syc-20356038 (Year: 2025).*

Giatti et al. Neuroactive steroids, their metabolites, and neuroinflammation Journal of Molecular Endocrinology (2012) 49, R125-R134 (Year: 2012).*

Gola et al. The New Role of Steroids in Viral Infections Frontiers in Clinical Drug Research—Anti Infectives: vol. 4 , pp. 93-141 Nov. 2017 (abstract only). (Year: 2017).*

Abuduli et al., "Effects of dietary phosphate on glucose and lipid metabolism"; American Journal of Physiology-Endocrinology and Metabolism; 2016; vol. 310, No. 7, pp. E526-E538.

Ahmed et al., "Nrf2 signaling pathway: Pivotal roles in inflammation"; Biochimica et Biophysica Acta; 2017; pp. 585-597.

Ali et al., "Regulation of Cholesterol Homeostasis by Hedgehog Signaling in Osteoarthritic Cartilage"; Arthritis & Rheumatology; 2016; vol. 68, No. 1, pp. 127-137.

Anders et al., "Differential expression analysis for sequence count data"; Genome Biology; 2010; pp. 1-12.

Bandari et al., "Sweet on Hedgehogs: Regulatory Roles of Heparan Sulfate Proteoglycans in Hedgehog-Dependent Cell Proliferation and Differentiation"; Current Protein and Peptide Science; 2015; pp. 1-12.

Billings et al., "Interactions of signaling proteins, growth factors and other proteins with heparan sulfate: Mechanisms and mysteries"; Connect Tissue Res.; 2015; vol. 56, No. 4, pp. 1-20.

Bindea et al., "ClueGO: a Cytoscape plug-in to decipher functionally grouped gene ontology and pathway annotation networks"; Systems biology; 2009; vol. 25, No. 8, pp. 1091-1093.

Bizzarri et al., "Inositol and pulmonary function. Could myo-inositol treatment downregulate inflammation and cytokine release syndrome in SARS-CoV-2?"; European Review for Medical and Pharmacological Sciences; 2020; vol. 24, pp. 3426-3432.

Böhmer et al., "A New Synthetic Access to Cyclic Oligonuclear Phenolic Compounds"; Makromol. Chem.; 1979; vol. 180, pp. 2503-2506.

Bosshart et al., "THP-1 cells as a model for human monocytes"; Annals of Translational Medicine; 2016; vol. 4, No. 21, pp. 1-4.

Collins et al., "Heparan sulfate as a regulator of inflammation and immunity"; Journal of Leukocyte Biology; 2018; vol. 105, pp. 81-92.

Damsker et al., "VBP15, a Glucocorticoid Analogue, Is Effective at Reducing Allergic Lung Inflammation in Mice"; PLoS One; 2013; vol. 8, No. 5, pp. 1-9.

Dennis et al., "Eicosanoid Storm in Infection and Inflammation"; Nat Rev Immunol; 2015; vol. 15, No. 8, pp. 1-29.

Elekes et al., "Inhibitory effects of synthetic somatostatin receptor subtype 4 agonists on acute and chronic airway Inflammation and hyperreactivity in the mouse"; European Journal of Pharmacology; 2008; vol. 578, pp. 313-322.

Evaldsson et al., "Anti-inflammatory effects of exogenous uridine in an animal model of lung inflammation"; International Immunopharmacology; 2007; vol. 7, pp. 1025-1032.

Farzan et al., "Hedgehog Processing and Biological Activity"; Am J Physiol Gastrointest Liver Physiol; 2008; vol. 294, No. 14, pp. 1-10.

Feyzi et al., "Age-dependent Modulation of Heparan Sulfate Structure and Function"; The Journal of Biological Chemistry; 1998; vol. 273, No. 22, pp. 13395-13398.

Freishtat et al., "Asthmatic Airway Epithelium Is Intrinsically Inflammatory and Mitotically Dyssynchronous"; American Journal of Respiratory Cell and Molecular Biology; 2011; vol. 44, pp. 863-869.

Gaber et al., "Metabolic regulation of inflammation"; Nature Reviews | Rheumatology; 2017; vol. 13, pp. 267-279.

Haines et al., "Argininosuccinate synthase: at the center of arginine metabolism"; Int J Biochem Mol Biol; 2011; vol. 2, No. 1, pp. 8-23.

Hall et al., "Anti-Inflammatory Activity of (Polyphenolic)-Sulfonates and Their Sodium Salts in Rodents"; AMetal Based Drugs; 1998; vol. 5, No. 2, pp. 67-75.

Haskó et al., "Inosine Inhibits Inflammatory Cytokine Production by a Posttranscriptional Mechanism and Protects Against Endotoxin-Induced Shock"; The Journal of Immunology; 2000, vol. 164; pp. 1-8.

Haskó et al., "Immunomodulatory and neuroprotective effects of inosine"; Atrends in Pharmacological Sciences; 2004; vol. 25, No. 3, pp. 152-157.

Holmström et al., "Nrf2 impacts cellular bioenergetics by controlling substrate availability for mitochondrial respiration"; Biology Open; 2013, pp. 761-770.

Horváth et al., "Transient receptor potential ankyrin 1 (TRPA1) receptor is involved in chronic arthritis: in vivo study using TRPA1-deficient mice"; Arthritis Research & Therapy; 2016; vol. 18, No. 6, pp. 1-14.

Horváth et al., "Methodological refinements of Aldara-induced psoriasiform dermatitis model in mice"; Scientific Reports; 2018; pp. 1-8.

Ihse et al., "Cellular internalization of alphasynuclein aggregates by cell surface heparan sulfate depends on aggregate conformation and cell type"; Scientific Reports; 2017; pp. 1-10.

Jarrett et al., "Mitochondrial DNA damage and its potential role in retinal degeneration"; Progress in Retinal and Eye Research; 2008; vol. 27, pp. 596-607.

Jeengar et al., "Uridine Ameliorates Dextran Sulfate-Sodium (DSS)-Induced Colitis in Mice"; Scientific Reports; 2017; pp. 1-10.

Kallendrusch et al., "The G protein-coupled receptor 55 ligand l-α-lysophosphatidylinositol exerts microglia-dependent neuroprotection after excitotoxic lesion"; Glia ; 2013; vol. 61, No. 11, pp. 1822-1831.

Karpińska et al., "Mechanisms of L-alpha-lysophosphatidylinositol-induced relaxation in human pulmonary arteries"; Life Sciences; 2018; vol. 192, pp. 38-45.

Kovac et al., "Nrf2 regulates ROS production by mitochondria and NADPH oxidase"; Biochimica et Biophysica Acta; 2015; vol. 1850, pp. 794-801.

(56) References Cited

OTHER PUBLICATIONS

Lee et al., "Hypoxanthine is a checkpoint stress metabolite in colonic epithelial energy modulation and barrier function"; J. Biol. Chem.; 2018; vol. 293, No. 16, pp. 6039-6051.
Fits et al., "Imiquimod-Induced Psoriasis-Like Skin Inflammation in Mice Is Mediated via the IL-23/IL-17 Axis"; The Journal of Immunology; 2009; vol. 182, No. 9, pp. 5836-5845.
Liu et al., "Preparation of metal complexes of double calix [4] arene derivatives for biomolecular detection"; Suzhou Institute of Biomedical Engineering and Technology, Chinese Academy of Science, People's Republic of China; 2018; 1 page.
Maïza, et al. "The role of heparan sulfates in protein aggregation and their potential impact on neurodegeneration."; FEBS letters; 2018; vol. 592, No. 23, pp. 3806-3818.
Marat et al., "Phosphatidylinositol 3-phosphates—at the interface between cell signaling and membrane traffic"; The Embo Journal; 2016; vol. 35, No. 6, pp. 561-579.
Naini et al., "Heparan Sulfate as a Therapeutic Target in Tauopathies: Insights From Zebrafish"; Frontiers in Cell and Developmental Biology; 2018; vol. 6, No. 163, pp. 1-17.
O'Neill et al., "A guide to immunometabolism for immunologists"; Nat Rev Immunol; 2016; vol. 16, No. 9, pp. 1-28.
Peiró et al., "Inflammation, glucose, and vascular cell damage: the role of the pentose phosphate pathway"; Cardiovascular Diabetology; 2016; vol. 15, No. 82, pp. 1-15.
Pinhal, et al., "Heparin and a cyclic octaphenol-octasulfonic acid (GL-522-Y-1) bind with high affinity to a 47-kDa protein from vascular endothelial cell surface and stimulate the synthesis and structural changes of heparan sulfate proteoglycan."; Thrombosis research; 2001; vol. 103, No. 1, pp. 35-45.
Presgraves et al., "Involvement of dopamine D2/D3 receptors and BDNF in the neuroprotective effects of S32504 and pramipexole against 1-methyl-4-phenylpyridinium in terminally differentiated SH-SY5Y cells"; AExperimental Neurology; 2004; vol. 190, pp. 157-170.
Przedborski et al., "MPTP as a Mitochondrial Neurotoxic Model of Parkinson's Disease"; Journal of Bioenergetics and Biomembranes; 2004; vol. 36, No. 4, pp. 375-379.
Rodik et al., "Calixarenes in Bio-Medical Researches"; Current Medicinal Chemistry 2009; vol. 16, pp. 1630-1655.
Rozova et al., "Uridine as a protector against hypoxia-induced lung injury"; Scientific Reports; 2019; pp. 1-7.
Nimse et al., "Biological applications of functionalized calixarenes"; Chem Soc Rev; 2013; vol. 42, pp. 366-386.
Scherz-Shouval et al., "Regulation of autophagy by ROS: physiology and pathology"; Trends in Biochemical Sciences; 2011; vol. 36, No. 1, pp. 30-38.
Schulte et al., "Alterations in Lipid and Inositol Metabolisms in Two Dopaminergic Disorders"; PLOS One; 2015, vol. 11, No. 1; pp. 1-12.
Shah et al., "Adipose Inflammation, Insulin Resistance, and Cardiovascular Disease"; JPEN J Parenter Enteral Nutr.; 2008; vol. 32, No. 6, pp. 638-644.
Snow et al., "Sulfated glycosaminoglycans: a common constituent of all amyloids?"; Laboratory investigation; a journal of technical methods and pathology; 1987; vol. 56, No. 1, pp. 120-123.
Song et al., "Aberrant Neuregulin1 Signaling in Amyotrophic Lateral Sclerosis"; J Neuropathol Exp Neurol.; 2012; vol. 71, No. 2, pp. 104-115.
Steinbrecher et al., "Role of Lipoprotein Peroxidation in the Pathogenesis of Atherosclerosis"; Clin. Cardiol; 1991; vol. 14, pp. 865-867.
Theocharis et al., "Extracellular matrix structure"; Advanced Drug Delivery Reviews; 2016; vol. 97, pp. 4-27.
Tyrrell et al., "Therapeutic uses of heparin beyond its traditional role as an anticoagulant"; TiPS.; 1995; vol. 16, pp. 198-204.
Van Der Veen et al., "The critical role of phosphatidylcholine and phosphatidylethanolamine metabolism in health and disease"; Biochimica et Biophysica Acta; 2017; vol. 1859, pp. 1558-1572.
Vimal et al., "L-Asparaginase: a feasible therapeutic molecule for multiple diseases"; 3 Biotech; 2018; vol. 8; pp. 1-3.
Wan et al., "Elucidating a molecular mechanism that the deterioration of porcine meat quality responds to increased cortisol based on transcriptome sequencing"; Scientific Reports; 2016; pp. 1-14.
Weinberg et al., "Targeting mitochondria metabolism for cancer therapy"; Nat Chem Biol; 2015; vol. 11, No. 1, pp. 1-18.
Xu et al., "Demystifying Heparan Sulfate-Protein Interactions"; Annu Rev Biochem; 2014; vol. 83; pp. 129-157.
Fu et al., "A novel calixsalen macrocycle: metal sensing behavior for Zn2+ and intracellular imaging application"; Tetrahedron Letters; 2012; vol. 53; pp. 804-807.
Yousaf et al., "Applications of calixarenes in cancer chemotherapy: facts and perspectives"; Drug Design, Development and Therapy; 2015; pp. 2831-2838.
Zhang et al., "BAP1 links metabolic regulation of ferroptosis to tumor suppression"; Nat Cell Biol; 2018; vol. 20. No. 10; pp. 1181-1192.
Zhu et al., "Synthesis of Chiral Calixarene-Like Salen Ligand and Application in Catalytic Asymmetric Friedel-Crafts Reaction of Aromatic Amines with Glyoxylate"; SYNLETT; 2006; No. 8; pp. 1221-1224.
Ziolkowski et al., "Heparan sulfate and heparanase play key roles in mouse β cell survival and autoimmune diabetes"; The Journal of clinical investigation; 2012; vol. 122, No. 1; pp. 132-141.
Janesch, et al. "Age-related changes in the levels and kinetics of pulmonary cytokine and chemokine responses to *Streptococcus pneumoniae* in mouse pneumonia models"; Cytokine; 2018; vol. 111; pp. 389-397.
Extended European Search Report issued on Aug. 13, 2019 in corresponding European Patent Application No. 19181021.7; 8 pages.
International Preliminary Report on Patentability issued on Dec. 21, 2021 in corresponding International Patent Application No. PCT/EP2020/066991; 8 pages.
International Search Report issued on Jul. 31, 2020 in corresponding International Patent Application No. PCT/EP2020/066991; 6 pages.
International Search Report issued on Sep. 17, 2020 in corresponding International Patent Application No. PCT/EP2020/066991; 6 pages.
Written Opinion issued on Jul. 31, 2020 in corresponding International Patent Application No. PCT/EP2020/066991; 7 pages.
Written Opinion issued on Sep. 17, 2020 in corresponding International Patent Application No. PCT/EP2020/066991; 7 pages.
Robinson et al., "edgeR: a Bioconductor package for differential expression analysis of digital gene expression data"; Bioinformatics; 2010; vol. 26, No. 1; pp. 139-140.
Laventie et al., "p-Sulfonato-calix[n]arenes Inhibit Staphylococcal Bicomponent Leukotoxins by Supermolecular Interactions", Biochemical Journal, The Authors Journal, Biochemical Society, Jan. 3, 2013, vol. 450, No. 3, pp. 559-571.
Stephens et al., "Structural Requirements for Anti-Oxidant Activity of calix[n]arenes and Their Associated Anti-Bacterial Activity", ChemComm Communication, The Royal Society of Chemistry, 2015, vol. 51, No. 5, pp. 851-854.
Office Action issued on Aug. 15, 2023, in corresponding Chinese Application No. 202080050508.6, 14 pages.
Examination Report issued on Jul. 19, 2023, in corresponding Indian Application No. 202127057346, 9 pages.
Español et al., "Calixarenes: Generalities and Their Role in Improving the Solubility, Biocompatibility, Stability, Bioavailability, Detection, and Transport of Biomolecules", Biomolecules, 2019, vol. 9, No. 90, 15 pages.
Wenzel, "Calixarenes and calix[4]resorcinarenes as chiral NMR solvating agents", J Incl Phenom Macrocycl Chem, 2014, vol. 78, 14 pages.

* cited by examiner

Fig. 2: SCA-744
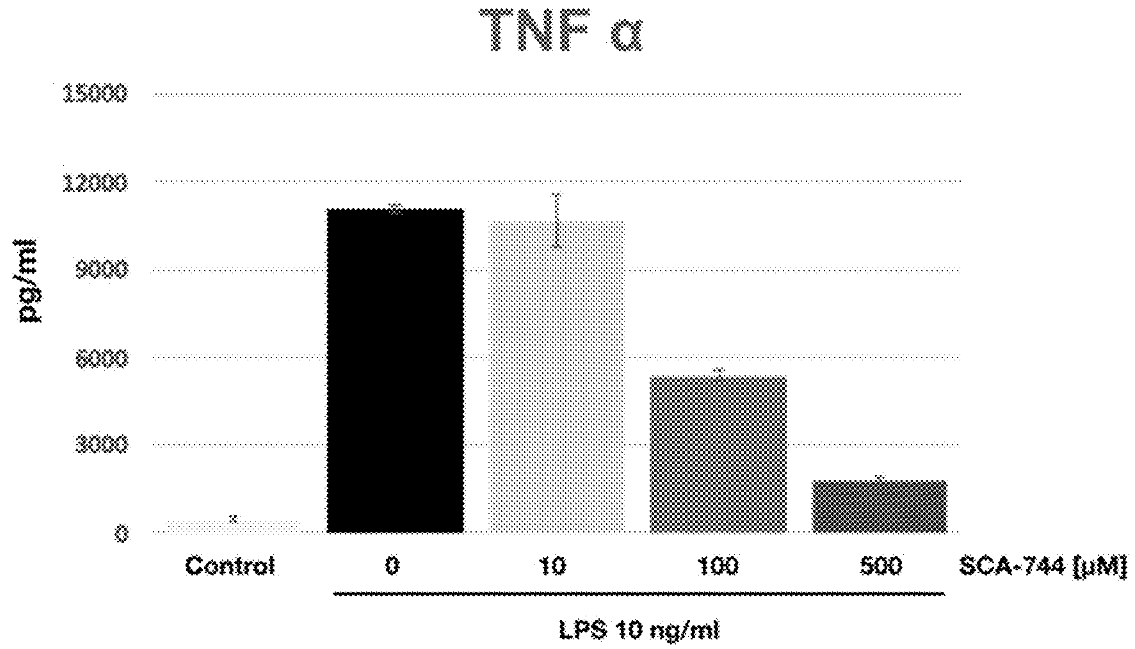
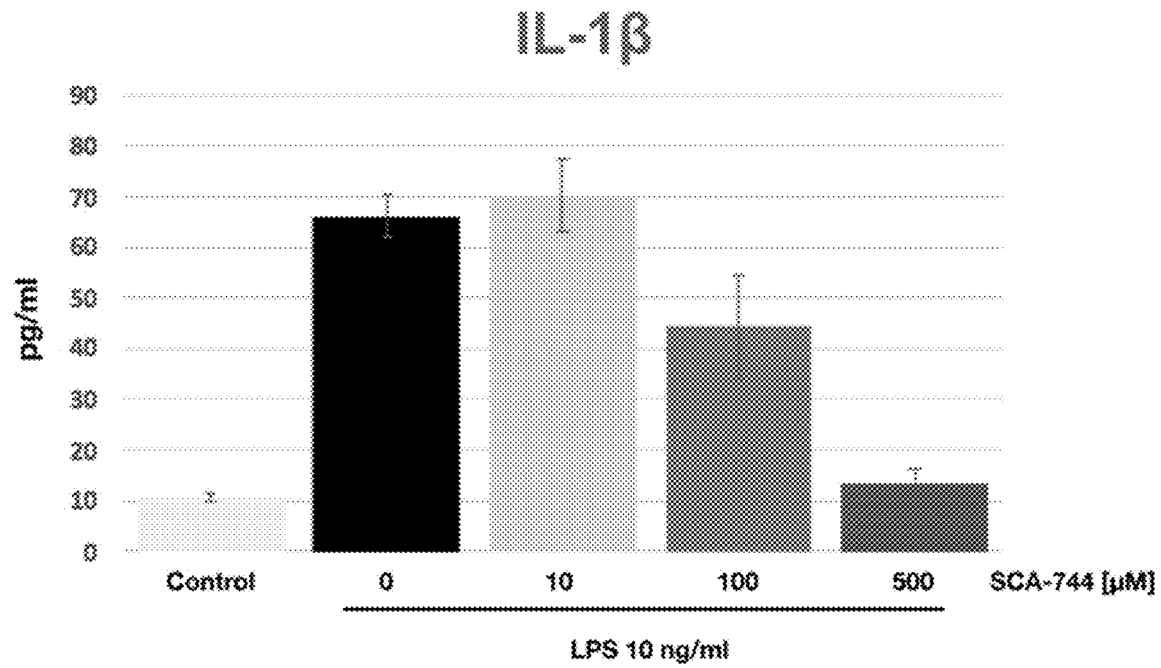

Fig. 2 (continued): SCA-744
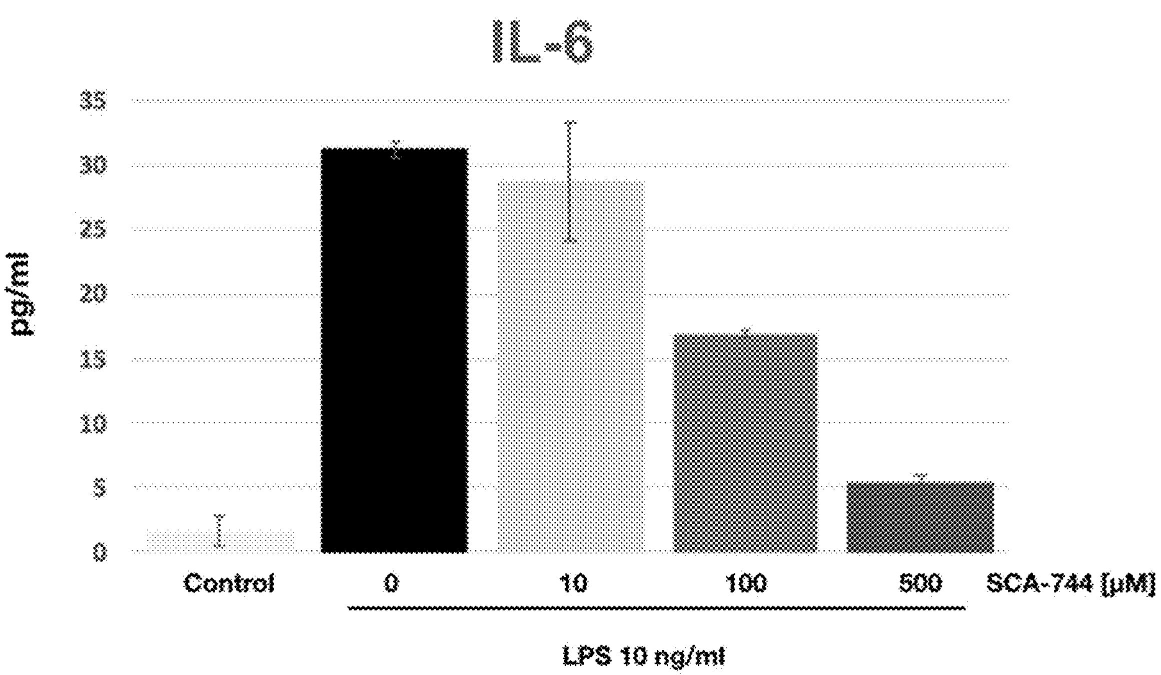

Fig. 3: SCA-754
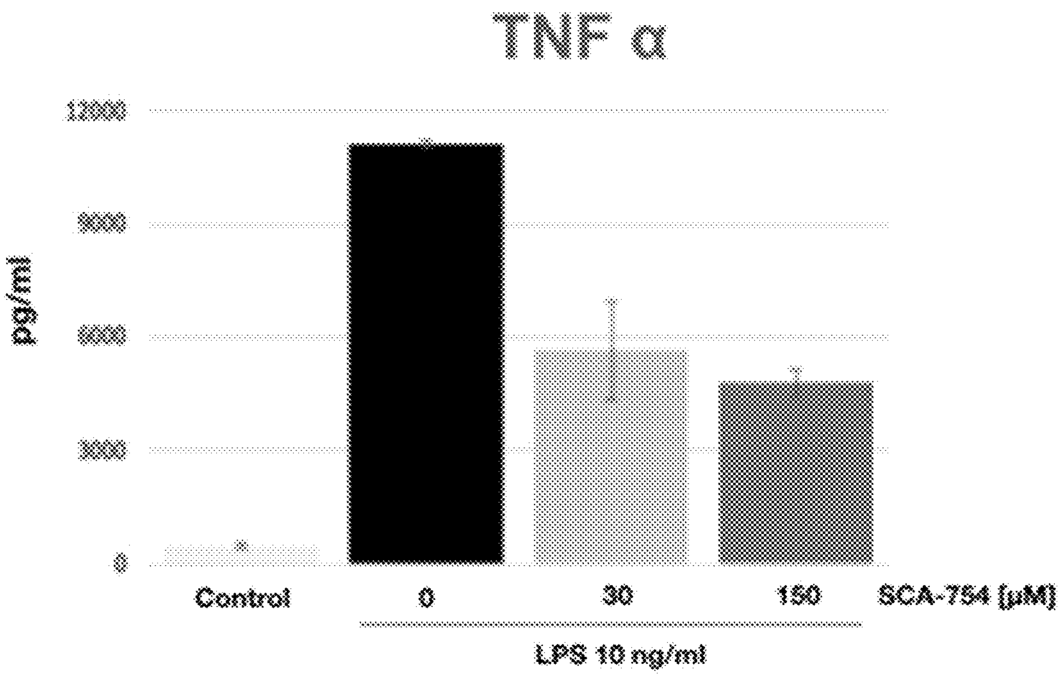
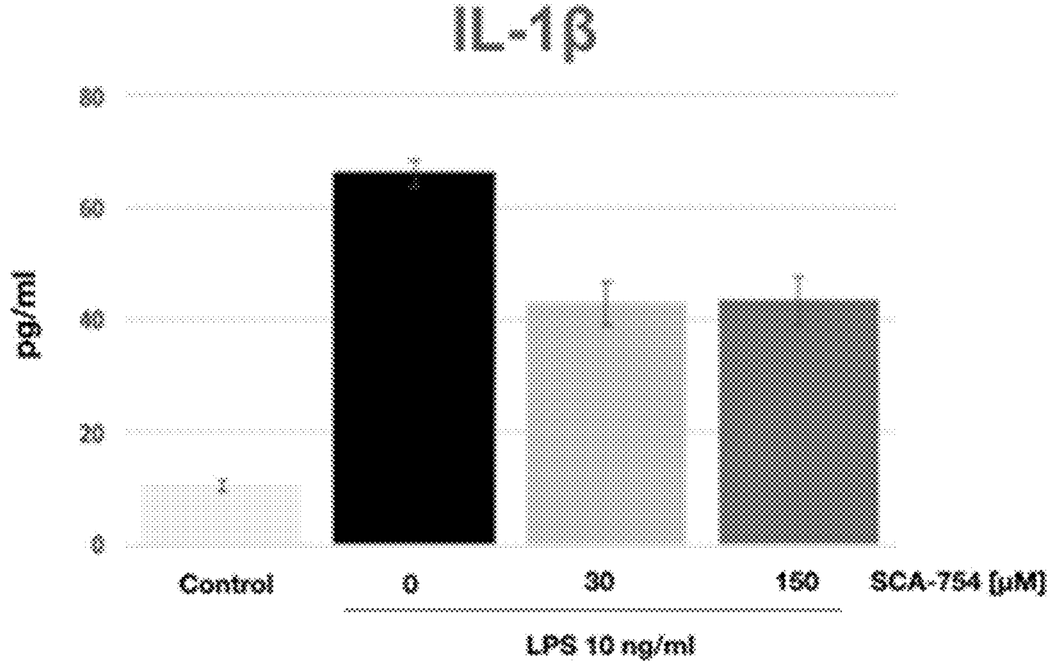

B
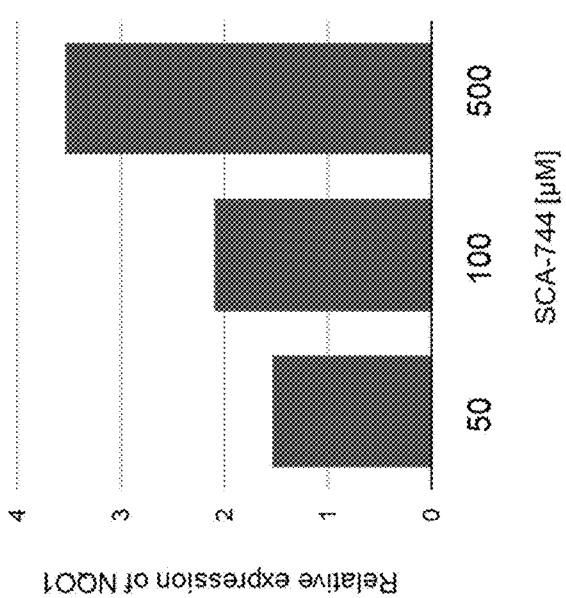
A
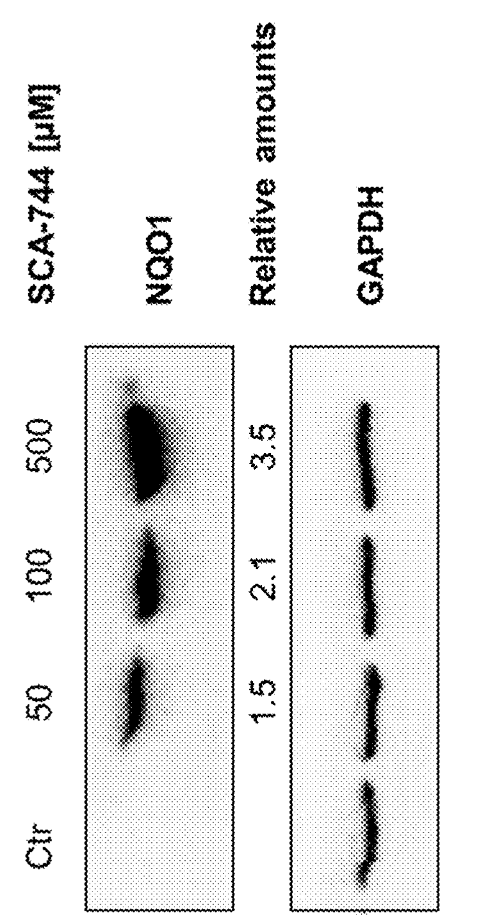
Fig. 4

HS
Heparan Sulfate
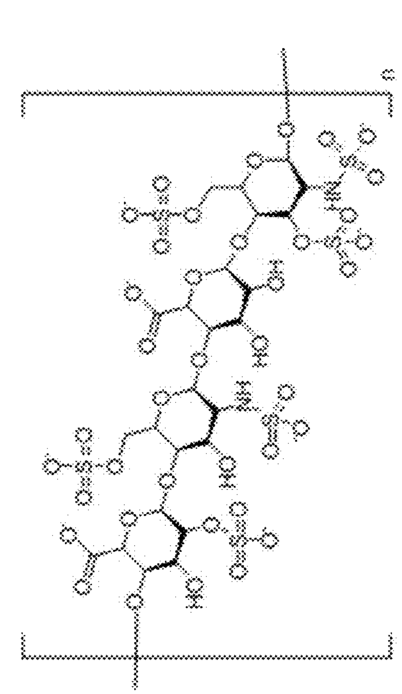
SCA-744
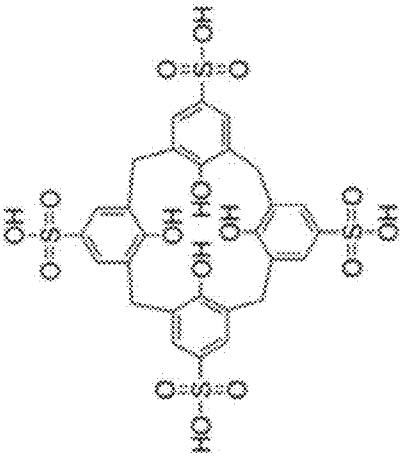
Fig. 8

Table 1.

Up – regulated genes

I (inflammation), L (lipids), O (oxidative), A (ageing)

| Gene | Gene ID | I | L | O/A | logFC | PValue | Alias | Description |
|---|---|---|---|---|---|---|---|---|
| CHAC1 | 79094 | | | ■ | 1,8600 | 5,94E-09 | Glutathione-specific γ-glutamylcyclotransferase 1 | The encoded protein has been shown to promote neuronal differentiation by deglycination of the Notch receptor |
| LDLR | 3949 | ■ | ■ | | 1,3922 | 3,43E-08 | LDL receptor | Low-density lipoprotein particle receptor activity |
| SLC7A11 | 23657 | | | ■ | 1,1386 | 0.0039 | Solute Carrier Family 6 Member, Norepinephrine | Regulator of norepinephrine homeostasis |
| ID3 | 3399 | ■ | | | 1,1002 | 5,27E-10 | Inhibitor of differentiation 3 | Implicated in regulating a variety of cellular processes, including cellular growth, senescence, differentiation, apoptosis, angiogenesis, and neoplastic transformation |
| INSIG1 | 3638 | | ■ | | 1,0730 | 4,19E-09 | Insulin-induced gene 1 protein | Mediates feedback control of cholesterol synthesis by controlling SCAP and HMGCR |
| NQO1 | 1728 | ■ | | ■ | 1,0600 | 3,23E-07 | NAD (P) H dehydrogenase 1 | Anti-oxidative activity involved in detoxification pathways |
| EGR1 | 1958 | | | ■ | 0,9903 | 6,07E-07 | Early Growth Response 1 | Age-associated up-regulation of EGR1 promotes granulosa cell apoptosis during follicle atresia in mice through the NF-κB pathway |
| ID1 | 3389 | ■ | | | 0,8958 | 3,55E-06 | Inhibitor of DNA Binding 1, HLH protein | Transcriptional regulator. The encoded protein is an inhibitor of DNA binding transcription factors. |
| SLC6A2 | 6530 | ■ | | | 0,8578 | 0,00016 | Norepinephrine Transporter, | Regulator of norepinephrine homeostasis |
| SGK1 | 6446 | | | ■ | 0,8107 | 2,00E-07 | S/T protein kinase, serum glucocorticoid-regulated kinase 1 | Involvement in the regulation of processes such as cell survival, neuronal excitability, and renal sodium excretion |
| SLC6A9 | 6536 | | | ■ | 0,7969 | 0,00129 | Solute Carrier Family 6 Norepinephrine Transporter | Regulator of norepinephrine homeostasis |
| DHCR24 | 1718 | ■ | ■ | ■ | 0,7336 | 4,75E-05 | SELADIN1, 3beta-hydroxysterol-Delta24 reductase | Cholesterol biosynthesis. Protects cells from oxidative stress, also protects against amyloid-beta peptide-induced apoptosis |
| IGFBP3 | 3486 | | ■ | | 0,5827 | 0,00048 | IGF-Binding Protein 3 | Fibronectin binding and insulin-like growth factor I binding |

Fig. 10: Table 1

I (inflammation), L (lipids), O (oxidative), A (ageing)

| Gene | Gene ID | I | L | A/O | logFC | PValue | Alias | Description |
|---|---|---|---|---|---|---|---|---|
| CABP7 | 164633 | | ■ | | -2,0924 | 1,64E-13 | Calcium-binding protein 7 | Negatively regulates Golgi-to-plasma membrane trafficking by interacting with PI4KB and inhibiting its activity |
| IKZF1 | 10320 | ■ | | | -2,0220 | 3,49E-09 | IKAROS Family Zinc Finger 1 | Among its related pathways are NF- κB Signaling and Dendritic Cells Developmental Lineage Pathway |
| GDF10 | 2662 | ■ | ■ | | -1,8408 | 1,23E-17 | Growth differentiation factor 10 / bone morphogenetic protein-3B (like TGF β) | Growth factor involved in osteogenesis and adipogenesis. Plays an inhibitory role in the process of osteoblast differentiation |
| IL6 | 3569 | ■ | | | -1,8300 | 0,0026 | Interleukin 6 | Pro-inflammatory cytokine |
| SPOCK3 | 50859 | ■ | | | -1,6232 | 0,0030 | Sparc/Osteonectin | FARC/osteonectin, cwcv and kazal like domains proteoglycan 3 Calcium ion binding and metalloendopeptidase inhibitor activity |
| MMP1 | 4312 | ■ | | | -1,4399 | 1,88E-05 | Matrix Metallopeptidase 1 | Matrix metallopeptidase 1 - ECM degradation |
| IL-1β | 3553 | ■ | | | -1,4309 | 3,09E-10 | Interleukin 1β | Pro-inflammatory cytokine |
| KCNMA1 | 3778 | ■ | ■ | | -1,3975 | 1,31E-08 | Calcium-activated K channel subunit α-1 | GABA receptor |
| CCL7 | 6354 | ■ | | | -1,2829 | 6,90E-06 | C-C Motif Chemokine Ligand 7 | Heparin binding and CCR1 chemokine receptor binding. |
| AQP1 | 358 | ■ | | | -1,2676 | 3,86E-07 | Aquaporin-1 | Aquaporin – related to Aβ |
| ITIH5 | 80760 | ■ | | | -1,2209 | 3,35E-07 | Inter-alpha-trypsin inhibitor heavy chain H | Inter α-Trypsin inhibitor - ECM |
| ABI3BP | 25890 | ■ | ■ | | -1,2161 | 3,97E-08 | Target of Nesh-SH3, Tarsh, Nesh-binding protein | ECM protein |
| CARTPT | 9607 | | ■ | | -1,2105 | 2,16E-10 | Cocaine- and amphetamine-regulated transcript protein | Play a role in appetite, energy balance, maintenance of body weight, reward and addiction, and the stress response |
| SCML4 | 256380 | | ■ | | -1,1986 | 2,38E-05 | Scm Polycomb Group Protein Like 4 | Act by forming multiprotein complexes, which are required to maintain the transcriptionally repressive state of homeotic genes throughout development |
| BMP5 | 653 | ■ | | | -1,182 | 0,0002 | Bone morphogenetic protein 5 | Cytokine activity *and* transforming growth factor beta receptor binding. It encodes a secreted ligand of the TGF-beta superfamily of proteins |
| INSM2 | 84684 | | ■ | | -0,9909 | 1,14E-07 | INSM Transcriptional Repressor 2 | May function as a growth suppressor or tumour suppressor in liver cells and in certain neurons |
| ADCY8 | 114 | | ■ | | -0,9595 | 2,43E-05 | Adenylate Cyclase 8 | Among its related pathways are Signaling by Hedgehog and Circadian entrainment. |

Fig. 10 (continued): Table 2

Up - regulated metabolites

I: anti-inflammatory, L: lipid homeostasis, O: anti-oxidative

| Metabolite | I | L | O | logFC | Pvalue | Alias | InChiKeys | Class | Ref. |
|---|---|---|---|---|---|---|---|---|---|
| Lysophosphatidylinositol | ■ | ■ | | 3,32 | 2,00E-09 | LPI, L-alpha-lysophosphatidylinositol | FBDBKJJQMHPGMP-FNFFQOHASA-N | Saturated Lysophospholipids | 1~2 |
| 1-stearoyl-sn-glycero-3-phospho-1D-myo-inositol | ■ | ■ | | 2,18 | 4,00E-09 | 1-stearoylglycerophosphoinositol | MXAFDFDAIFZFET-QIEOIKHQSA-N | Saturated Lysophospholipids | 3 |
| Hypoxanthine | | | ■ | 2,15 | 1,82E-05 | 6-Hydroxypurine, 9H-Purin-6-ol, Sarkin | FDGQSTZJBFJUBT-UHFFFAOYSA-N | Purinones | 4 |
| 1-oleoyl-sn-glycero-3-phospho-D-myo-inositol | ■ | ■ | | 2,11 | 1,37E-07 | 1-oleoyl-GPI, 1-oleoyl-GPI (18:1) | UGDOFRYHDCDVHD-GFMLYYSJSA-N | Phosphatidyl-inositols | 5 |
| 1,3,6,7-Tetrahydroxy-8-(3-hydroxy-3-methylbutyl)-2-(3-methyl-2-buten-1-yl)-9H-xanthen-9-one | ■ | | | 1,90 | 4,10E-09 | beta.-Alanine, Garcinone-C | HLOCLVMUASBDDP-UHFFFAOYSA-N | Flavonoids | 6 |
| Inosine | ■ | | ■ | 1,46 | 1,71E-04 | Ribonosine, Atorel | UGQMRVRMYYASKQ-KQYNXXCUSA-N | Purine nucleosides | 7 |
| L-arginino-succinate | | | ■ | 1,17 | 1,19E-06 | N-(L-arginino)-succinate | KDZOASGQNOPSCU-ZBHICJROSA-M | Succinates | 8 |
| 1-hexadecanoyl-2-[(Z)-octadec-9-enoyl]-sn-glycerol 3-(2-aminoethylphosphonate) | | ■ | | 1,15 | 1,01E-04 | C13878, CHEBI:34085, Q27115800 | ITQDKOBSRNKQCX-ZCXUNETKSA-N | Phosphatidyl-ethanolamines | 9 |
| D-erythro-D-gluco-octose Alpha-1-phosphate | | ■ | | 1,13 | 1,99E-04 | Octose 1-phosphate | QXEOPFWGTBQGMN-GVCIEGHISA-L | Sugar phosphates | 10 |
| (2R)-1-{[Hydroxy{[(1S,5R)-2,3,4,6-tetrahydroxy-5-(phosphonooxy)cyclohexyl]oxy}phosphoryl]oxy}-3-(palmitoyloxy)-2-propanyl (10Z,13Z,16Z,19Z)-10,13,16,19-docosatetraenoate | | ■ | ■ | 1,06 | 4,64E-05 | PIP(16:0/22:5n6), PIP(16:0/22:5w6)Phosphatidylinositol | JGFYAFZFSQXQIQ-QIVMTMOMSA-N | Phosphatidyl-inositols | 11 |
| Uridine | ■ | | | 1,03 | 1,30E-03 | Uracil riboside, 1-beta-D-Ribofuranosyluracil | DRTQHJPVMGBUCF-XVFCMESISA-N | Pyrimidine nucleosides | 12-14 |

FDR<0.05, LogFold > 1

Fig. 10 (continued): Table 3

Down - regulated metabolites (selected)

I. Glucose metabolism

G: glucose metabolism, I: anti-inflammatory, O: anti-oxidative

| Metabolites | G | logFC | Pvalue | Alias | InChiKeys | class | References |
|---|---|---|---|---|---|---|---|
| 1,6-Di-O-phosphonohex-2-ulofuranose | ■ | -4,76 | 1,40E-09 | fructose-1,6-diphosphate | RNBGYGVWRKECFJ-UHFFFAOYSA-N | fructose-diphosphates | G I O (15,16,17) |
| 4,5,6,7-Tetrahydroxy-2-oxo-8-(phosphonooxy)octanoic acid | ■ | -3,84 | 1,80E-06 | 4,5,6,7-Tetrahydroxy-2-oxo-8-(phosphonooxy)octanoic acid | VBUYCZFBVCCYFD-FLRLBIABSA-N | sugar acids | |
| Dihydroxyacetone phosphate | ■ | -3,41 | 4,40E-10 | DHAP, Glycerone phosphate | GNGACRATGGDKBX-UHFFFAOYSA-N | sugar phosphates | |
| 1-(Propyldisulfanyl)-1-(propylsulfinyl)propane | ■ | -2,74 | 3,50E-03 | Kdo-4-phosphate, 3-Deoxy-2-octulosonate-4-phosphate | UTNZDUXOWSLJKE-O8RKOA8JSA-N | sugar acids | |
| 2-carboxy-3-keto-D-arabinitol-1,5-bisphosphate | ■ | -2,40 | 3,20E-09 | 2-carboxy-3-keto-D-arabinitol-1,5-bisphosphate | DUTCDHZZJUGPFV-UHFFFAOYSA-I | sugar phosphates | |
| D-(-)-3-Phosphoglyceric acid | ■ | -2,12 | 3,10E-08 | 3PG, Glyceric acid-3-phosphate | OSJPPGNTCRNQQC-REOHCLBHSA-N | sugar acids | |
| Gluconic acid | ■ | -1,79 | 1,80E-05 | D-gluconic acid, dextronic acid, maltonic acid | RGHNJXZEOKUKBD-SQOUGZDYSA-N | sugar acids | |
| 2156QF7O8M (D-Erythrose 4-phosphate) | ■ | -1,74 | 3,00E-08 | erythrose 4-phosphate, threose 4-phosphate | NGHMDNPXVRFFGS-IUYQGCFVSA-N | sugar phosphates | |
| Arbutin 6-phosphate | ■ | -1,64 | 1,40E-05 | 4-hydroxyphenyl 6-O-phosphono-beta-D-glucopyranoside | FBHYCDOVYMVLEN-RMPHRYRLSA-N | glycerophosphates | |
| Tris(hydroxymethyl)aminomethane | ■ | -1,51 | 9,50E-02 | Trometamol, TROMETHAMINE | LENZDBCJOHFCAS-UHFFFAOYSA-N | propylene glycols | |
| 2-Keto-glutaramic acid | ■ | -1,40 | 7,60E-05 | alpha-Ketoglutaramate, 2-Oxoglutaramic acid, 2-oxoglutaramate | COJBGNAUUSNXHX-UHFFFAOYSA-N | ketoglutaric acids | |
| β-Nicotinamide adenine dinucleotide reduced (NADH) | ■ | -1,36 | 9,8E-07 | NADH, DPNH, beta-NADH, beta-DPNH, Dihydrocozymase | BOPGDPNILDQYTO-NNYOXOHSSA-L | adenine nucleotides | |
| Phosphoenolpyruvic acid | ■ | -1,18 | 9,30E-08 | 2-Propenoic acid, 2-(phosphonooxy), 2-(phosphonooxy)prop-2-enoic acid | DTBNBXWJWCWCIK-UHFFFAOYSA-N | hydroxy acids | |
| Deoxyadenosine 5'-triphosphate (dATP) | ■ | -1,12 | 2,5E-05 | 2'-deoxyadenosine triphosphate, dATP cpd, deoxy-ATP | SUYVUBYJARFZHO-UHFFFAOYSA-N | deoxyadenine nucleotides | |
| Sucrose | ■ | -1,12 | 2,60E-04 | saccharose, sugar, cane sugar | CZMRCDWAGMRECN-UGDNZRGBSA-N | disaccharides | |

FDR<0.05, LogFold < -1

Fig. 10 (continued): Table 4

Fig. 11
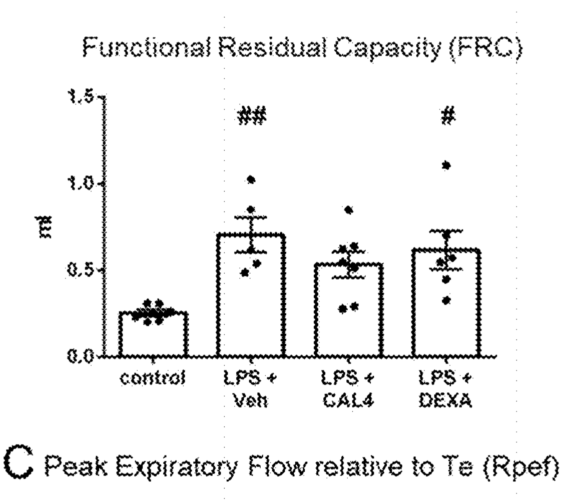
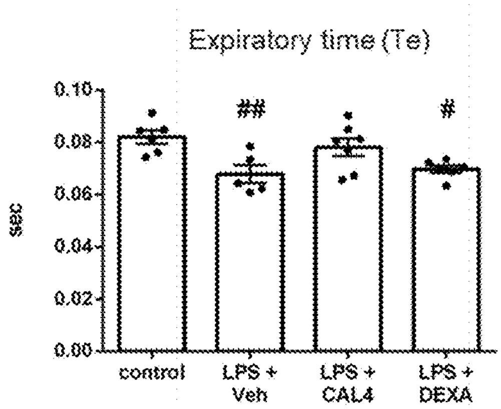
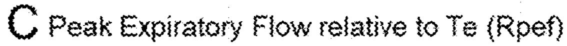
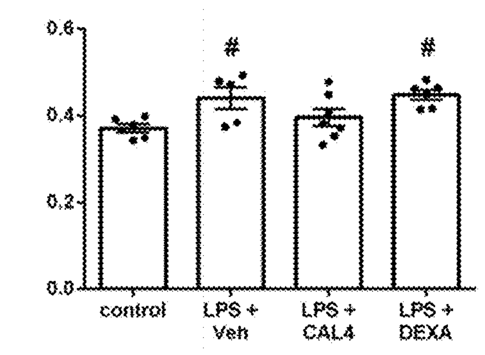
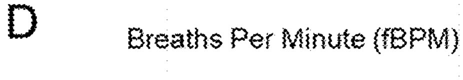
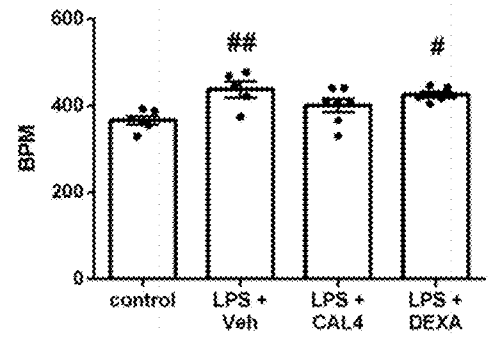
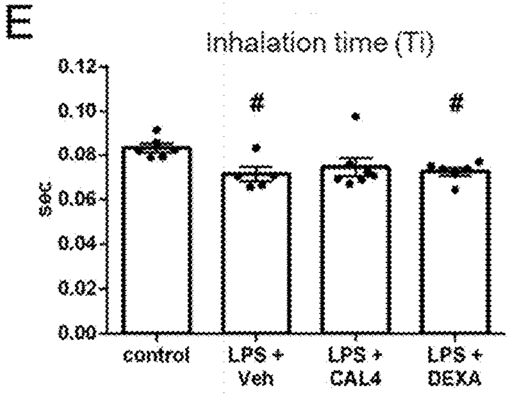

Fig. 14
A
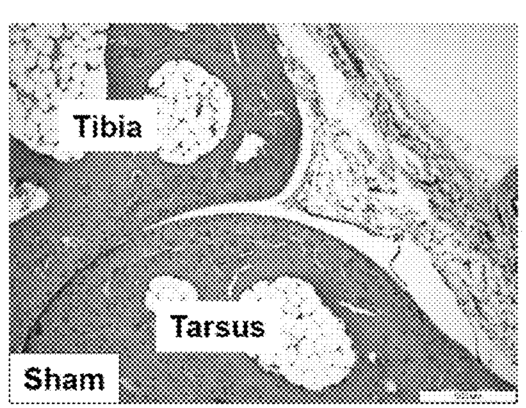
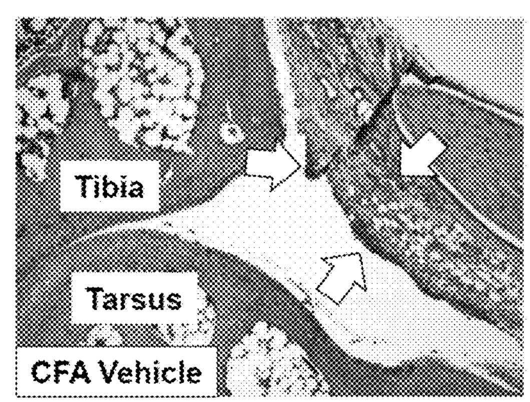
B
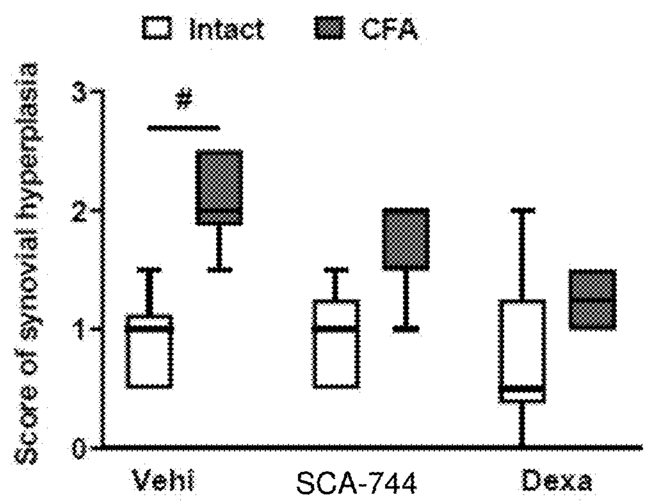

1 2 3 4 5 6 7 8

SCA-744 [µM]

SCA-754 [µM]

Fig. 20
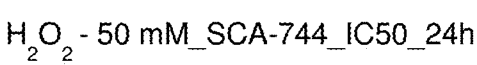
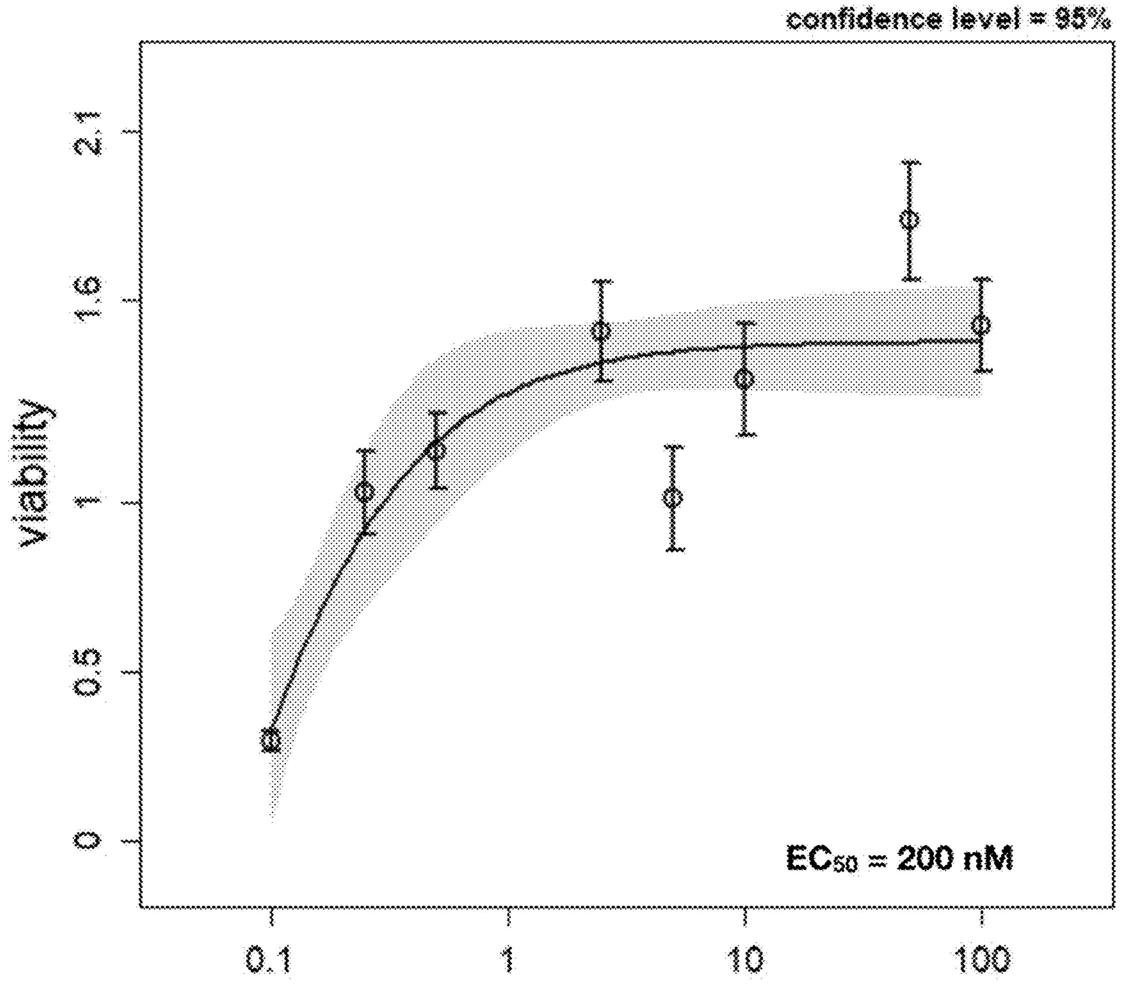

CALIXARENE COMPOUNDS AND USES THEREOF

FIELD

The present invention relates to novel compounds of general Formula (I)

(I)

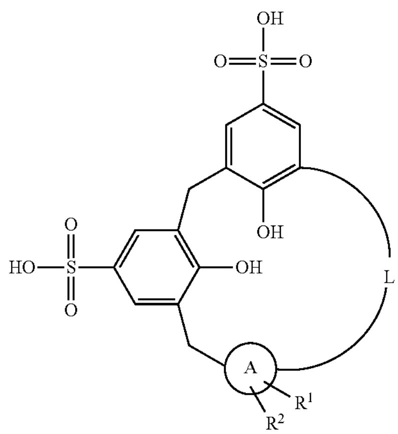

wherein the elements A, L, $R^1$ and $R^2$ have the meanings given in the description and claims, process for preparing these compounds and their use as medicaments, or other use.

BACKGROUND

Inflammatory processes are characterized by a diverse aetiology, and there are several well-established therapeutic strategies, steroid (corticosteroid, or glucocorto therapy being one of the most effective and widely used approach. These have been used with great success in several disease areas (e.g. treatment of inflammatory and auto-immune diseases, such as rheumatoid arthritis, asthma, colitis ulcerosa, Chron's disease, etc). Most diseases currently addressed by steroid therapy have no cure, and therefore long-term, chronic treatment is typically required. Despite the tremendous clinical success with glucocorticoid therapy, there is an unmet medical need for alternative intervention strategies, mainly due to the side-effects that appear with different severity and hamper long-term treatment. The chronic use of corticoidsteroids at optimal efficacy doses includes hyperglycemia, muscle wasting, hypertension, osteoporosis and neurological symptoms.

The mode of action of glucocorticoids is receptor activation that leads to nuclear translocation and modulation of gene transcription, resulting in stimulation or repression of the expression of target genes. The anti-inflammatory action of glucocorticoids is based on the repression of major pro-inflammatory gene products, such as TNFα and IL-6 via the NF-κB transcription factor, through a mechanism called trans-repression. Glucocorticoids also affect the expression of genes involved in adverse effects. Drug discovery campaigns based on glucocorticoid receptor agonists with separation of helpful and harmful modulation of gene expression have been so far unsuccessful.

Satish Balasaheb Nimse and Taisun Kim (Chem. Soc. Rev. 2013 (42):366-386) describe biological applications of functionalized calixarenes, referring to antiviral, antibacterial, antifungal, antitubercular and anticancer activities.

Yousaf et al. (Drug Des Devel Ther. 2015 (9):2831-8) disclose the anticancer potential of the calixarenes and their drug loading properties.

U.S. Pat. No. 5,489,612 discloses calixarene derivatives, their synthesis and their use as chloride channel blockers. More precisely, U.S. Pat. No. 5,489,612 discloses the use of several compounds in the treatment of respiratory disorders, skeletal muscle disorders and cardiovascular disorders.

WO00/07585 discloses the use of calixarenes in the treatment of fibrotic diseases.

WO2017093363 discloses a sodium salt of 4-sulfocalix[4]arene for use in the treatment of neurodegenerative disease.

WO9403165A1 discloses anti-thrombotic treatment with derivatized calix[n]arene compounds.

Hall et al. (Metal-Based Drugs 1998, 5(2):67-75) discloses f polyphenolic-sulfonated compounds with an effect of protecting against LPS-induced shock, the release of regulatory cytokines (TNFα and IL-1), binding to receptors on target inflammatory cells, and the effect of blocking elastase and cyclooxygenase activities and cell adhesion.

Pinhal et al. (Thrombosis Research 2001, 103(1):35-45) describes a cyclic octaphenol-octasulfonic acid and its methylated and acetylated derivatives and their effect on synthesis of heparan sulfate proteoglycan secreted by endothelial cells.

Tyrrell et al. (Trends in Pharmacological Scien, Elsevier, Haywarth, G B, 1995, 16(6):198-204) discloses therapeutic uses of heparin beyond its role as anticoagulant.

Rodik et al. (Current Medicinal Chemistry 2009, 16:1630-1655) discloses derivatized calix[n]arene compounds which are enzyme mimetics, mimetics of receptors, enzymes, antibodies and enzyme inhibitors, membranoactive calixarenes, those with bioactive properties, their use in DNA transfection, and in magnetic resonance imaging.

There is a need for new anti-inflammatory compounds and for new approaches to identifying such compounds. It is a further aim of the present invention to provide for new compounds which have an effect mimicking a glucocorticoid or heparan sulfate in vitro and in vivo and have suitable pharmacological and/or pharmacokinetic properties to enable them to be used as medicaments.

SUMMARY

It is the objective of the present invention to provide new compounds with anti-inflammatory properties, and anti-inflammatory preparations. The objective is solved by the subject of the present claims and as further described herein.

It has surprisingly been found, that compounds of general Formula (I), wherein the wherein the elements A, L, $R^1$ and $R^2$ have the meanings below, act as specific anti-inflammatory compounds. It has further been surprisingly found that such compounds can be used in anti-inflammatory, anti-oxidative, anti-ageing, or lipid metabolism modulation therapy or prophylaxis. Unexpectedly, the mode of action of a series of compounds, among them 4-sulfocalix[4]arene which was previously described for the treatment of neurodegenerative disease, allowed its use in new medical, cosmetic or nutritional applications.

Various objects, features, aspects, and advantages of the present invention will become more apparent from the following detailed description of embodiments of the invention.

The present invention relates to preparations comprising a compound of general Formula (I):

(I)

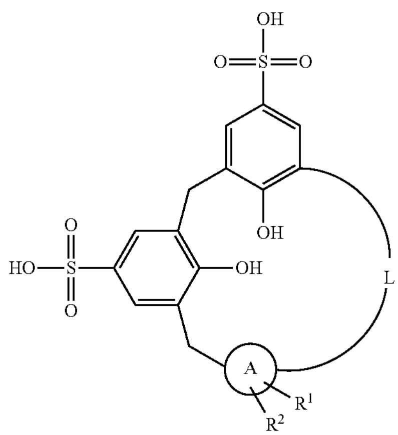

wherein

A is selected from is aryl, 5-12 membered heteroaryl, $C_{3-10}$cycloalkyl, 3-8 membered heterocycloalkyl, and L is a bond or a linker selected from optionally substituted $C_{1-6}$-alkyl and $—(CH_2)_n—O—(CH_2)_m—$, or a compound of Formula (II), (II)

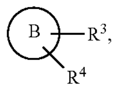

wherein

B is selected from is aryl, 5-12 membered heteroaryl, $C_{3-10}$cycloalkyl, 3-8 membered heterocycloalkyl, and $R^1$ and $R^3$ are independently from each other selected from the group consisting of hydrogen, halogen, $—OR^a$, $—NR^aR^a$, $R^2$ and $R^4$ are independently from each other selected from the group consisting of hydrogen, halogen, $—SO_3R^a$, $—OR^a$, and $—COOR^a$, and each $R^a$ is hydrogen or $C_{1-3}$alkyl, n and m denote independently from each other 0, 1, or 2;

optionally in the form of a pharmaceutically acceptable salt, enantiomer, racemate, and mixtures thereof.

The compounds described herein may be provided in the form of its pharmaceutically acceptable salt, enantiomer, racemate, and mixtures thereof. Therefore, the term "compound" as further described herein or "compound of the invention" shall refer to any of the forms, as determined by the structural formula, the pharmaceutically acceptable salt, enantiomer, racemate, and mixtures thereof.

Surprisingly, such compounds have anti-inflammatory, anti-oxidative, anti-ageing, or lipid metabolism modulation properties.

It has surprisingly been found that compounds of general Formula (I), wherein the wherein the elements A, L, $R^1$ and $R^2$ have the meanings further described herein, with the proviso that the compound is not 5,11,17,23-sulfonato-25,26,27,28-tetrahydroxycalix[4]arene (4-sulfocalix[4]arene, herein also referred to as SCA-744), could be provided as novel compounds (or pharmaceutically acceptable salts thereof) with the properties further described herein.

One embodiment of the invention relates to compounds as described herein, wherein L is a compound of Formula (II).

One embodiment of the invention relates to compounds as described herein, wherein L is a linker consisting of $(—CH2-)_n$, wherein n=1, 2, 3, 4, 5; or (—CF2-), wherein n=1, 2, 3, 4, 5; or $(—CH_2—O—CH_2—)_n$, wherein n=1, 2, 3, 4.

According to a specific aspect, heteroaryl is an N- or O-heterocycle, optionally a 5 or 6-membered N- or O-heterocycle.

According to a specific aspect, halogen is any one of F, Cl, or Br.

One embodiment of the invention relates to compounds as described herein, wherein A and B independently from one another denote phenyl.

One embodiment of the invention relates to compounds as described herein, wherein $R^a$ denotes H.

One embodiment of the invention relates to compounds as described herein wherein each $CH_2$ group is deuterated ($CD_2$).

One embodiment of the invention relates to compounds as described herein, wherein L is a compound of Formula (II), and A and B are independently from each other selected from a 5-6-membered N-heterocycle, or a 6-membered benzene-ring, and each of $R^2$ and $R^4$ is —COOH.

One embodiment of the invention relates to compounds which are 3-sulfocalix[3]arenes with varying (—CH2-) linker segments, for example, compounds as described herein, wherein L is a linker consisting of $(—CH2-)_n$, wherein n=1, 2, 3, 4, 5; A denotes benzene, each of $R^1$ and $R^3$ is $—OR^a$; and each of $R^2$ and $R^4$ is $—SO_3R^a$, in particular wherein $R^a$ is hydrogen.

One embodiment relates to compounds, which are characterized by one or more of the following features:

a) A is phenyl (which is optionally substituted);

b) B is phenyl (which is optionally substituted), pyrazine, pyridine, or pyrol;

c) $R^1$ and/or $R^3$ is —H or —OH;

d) $R^2$ and/or $R^4$ is $—SO_3H$.

A calixarene is generally defined as a macrocycle or cyclic oligomer based on a hydroxyalkylation product of a phenol and an aldehyde. Calixarenes are characterised by a three-dimensional basket, cup or bucket shape. A calix[4]arene has 4 units in the ring and a calix[3]arene has 3 units in the ring. The calixarene ring is also herein referred to as "backbone".

The ring may consist of repeating units, which are identical or not, and optionally linker elements, e.g., wherein the linker is L as further described herein, in particular a linear linker. A linker L which is any other than the compound of Formula (II) is herein also referred to as "linear linker" or "linear L". In specific embodiments L is a linear linker such as a (—CH2-) linker segment, for example, wherein L is a linear linker consisting of $(—CH2-)_n$, wherein n=1, 2, 3, 4, 5, in particular wherein L is CH2 ("methylene bridge").

In specific embodiments, the calixarene ring comprises or consists of four identical repeating units linked by a linear L, in particular wherein L is CH2.

In specific embodiments, the calixarene ring comprises or consists of three identical repeating units and a fourth unit, linked by a linear L, in particular wherein L is CH2; and wherein the fourth unit differs from the repeating units and is composed of the Formula (II).

In calix[4]arenes the internal volume is around 10 cubic angstroms. Calixarenes are characterised by a wide upper rim and a narrow lower rim and a central annulus. With phenol as a starting material the 4 hydroxyl groups are intraannular on the lower rim.

Specific embodiments refer to compounds as described herein (or enantiomers or pharmaceutically acceptable salts thereof), comprising a calixarene backbone consisting of two identical elements which are each phenyl with sulfonic acid groups attached (as depicted in Formula (I)), and two further elements which are each five- and/or six-membered ring elements as further described herein, thereby obtaining a calixarene backbone consisting of four ring elements. Alternatively, the calixarene backbone may consist of three ring elements which are each five- and/or six-membered ring systems, wherein at least two of them are identical elements which are each phenyl with sulfonic acid groups attached (as depicted in Formula (I)), that are linked by a specific linear linker, as further described herein.

Specific embodiments refer to asymmetric calixarenes, which are composed of non-identical elements, such as for example substituted phenolic repeating units and at least one substituted phenolic unit that differs from the repeating units. According to a specific embodiment, the asymmetric calixarene compound comprises or is composed of two, or three p-sulfonated phenolic units connected by methylene bridges, and one or two p-substituted phenolic units, which are each independently different from the p-sulfonated phenolic units. Asymmetric calixarenes are macrocyclic compounds composed of elements linked to each other to for a cyclic structure, by a linkage (such as a methylene bridge or other linker), and specifically characterized by at least one element that differs from any one or more of the other elements.

Specific embodiments refer to 3-sulfocalix[3]arenes obtained by 2+1 fragment condensation (for example comprising a calixarene backbone consisting of three methylene bridged ring elements and a linear linker); or 4-sulfocalix[4]arenes obtained by 3+1 fragment condensation (for example comprising a calixarene backbone consisting of four methylene bridged ring elements).

Specific embodiments refer to 3-sulfocalix[3]arenes, in particular 3-sulfocalix[3]arenes obtained by 2+1 fragment condensation.

Specific embodiments refer to 4-sulfocalix[4]arenes, in particular 4-sulfocalix[4]arenes obtained by 2+2 or 3+1 fragment condensation.

Specific embodiments refer to novel uses of a 4-sulfocalix[4]arene of Formula (III), pharmaceutically acceptable salts thereof e.g. a sodium salt, enantiomers or derivatives of 4-sulfocalix[4]arene.

Formula (III)

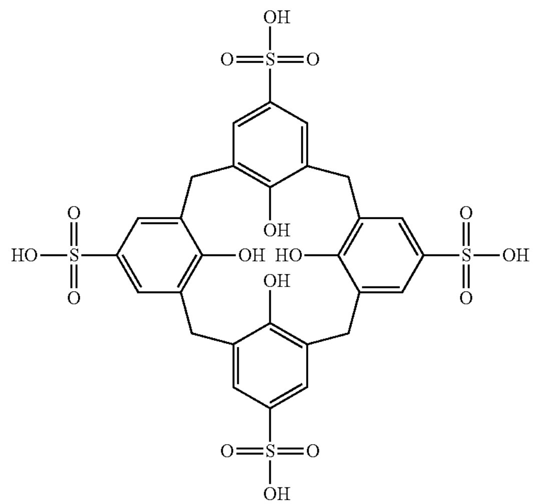

Specific embodiments refer to compounds selected from the table below (or pharmaceutically acceptable salts of any of such compounds). Formula (IV) and Formula (V) shows the naming conventions used Formula (IV)

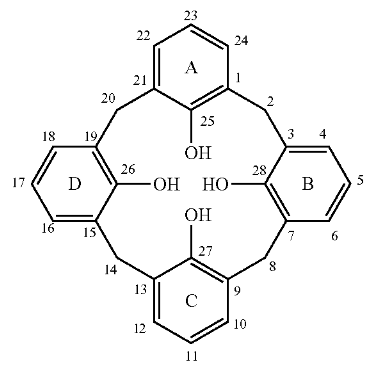

Formula (V)

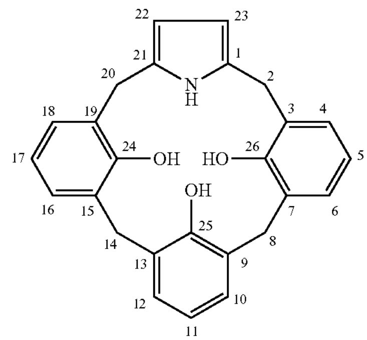

TABLE
| Preferred compounds | | |
| --- | --- | --- |
| Compound | Name | Formula |
| SCA-744 | 4-sulfocalix[4]arene | 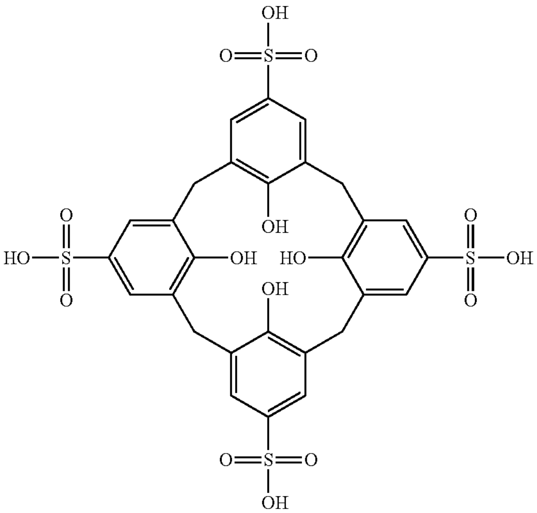 [SMILES: O=S(=O)(O)c1cc2c(O)c(c1)Cc1cc(S(=O)(=O)O)cc(c1O)Cc1cc(S(=O)(=O)O)cc(c1O)Cc1cc(S(=O)(=O)O)cc(c1O)C2] |
| SCA-745 | 3-sulfocalix[4]-benzene-arene | 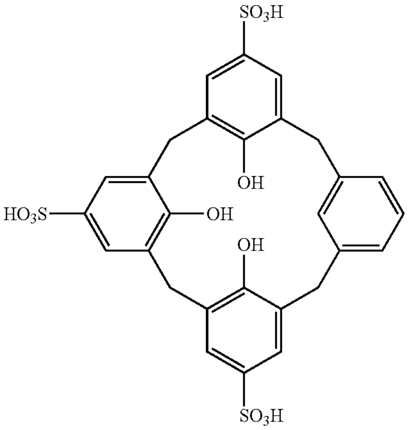 [SMILES: O=S(=O)(O)c1cc2c(O)c(c1)Cc1cc(S(=O)(=O)O)cc(c1O)Cc1cc(S(=O)(=O)O)cc(c1O)Cc1cccc(c1)C2] |
| SCA-746 | 3-sulfocalix[4]-pyridine-2,6-arene | 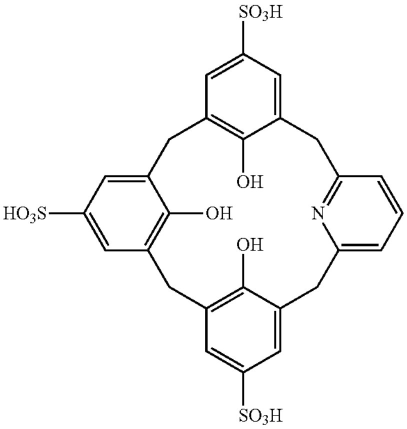 [SMILES: O=S(=O)(O)c1cc2c(O)c(c1)Cc1cc(S(=O)(=O)O)cc(c1O)Cc1cc(S(=O)(=O)O)cc(c1O)Cc1cccc(n1)C2] |

TABLE-continued
| Preferred compounds | | |
|---|---|---|
| Compound | Name | Formula |
| SCA-747 | 3-sulfocalix[4]-pyrazine-2,6-arene | 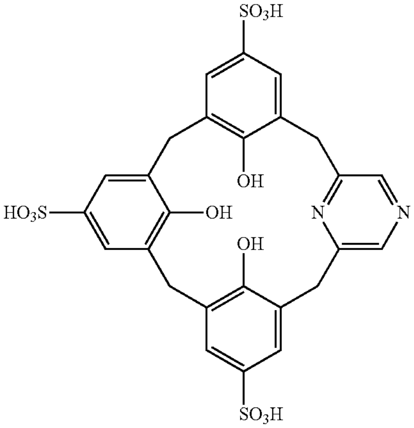 [SMILES: O=S(=O)(O)c1cc2c(O)c(c1)Cc1cc(S(=O)(=O)O)cc(c1O)Cc1cc(S(=O)(=O)O)cc(c1O)Cc1cncc(n1)C2] |
| SCA-748 | 3-sulfocalix[4]-pyrrol-3,4-arene | 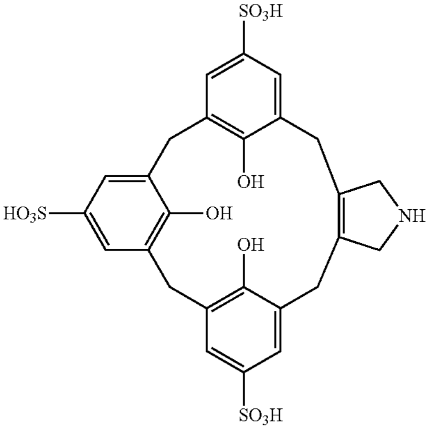 [SMILES: O=S(=O)(O)c1cc2c(O)c(c1)Cc1cc(S(=O)(=O)O)cc(c1O)Cc1cc(S(=O)(=O)O)cc(c1O)CC1=C(CNC1)C2] |
| SCA-749 | 3-sulfocalix[4]-pyridine-3,5-arene | 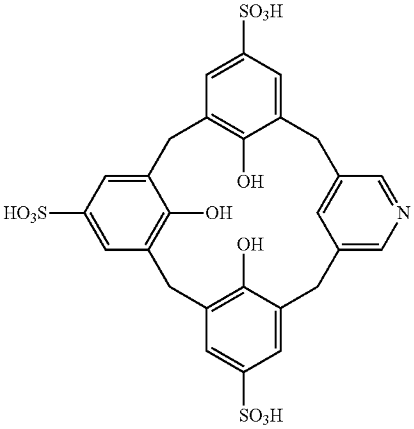 [SMILES: O=S(=O)(O)c1cc2c(O)c(c1)Cc1cc(S(=O)(=O)O)cc(c1O)Cc1cc(S(=O)(=O)O)cc(c1O)Cc1cncc(c1)C2] |

TABLE-continued
| Preferred compounds | | |
|---|---|---|
| Compound | Name | Formula |
| SCA-750 | 3-sulfocalix[3]-alkyloxy-arene (n = 1-6, m = 1-6) | 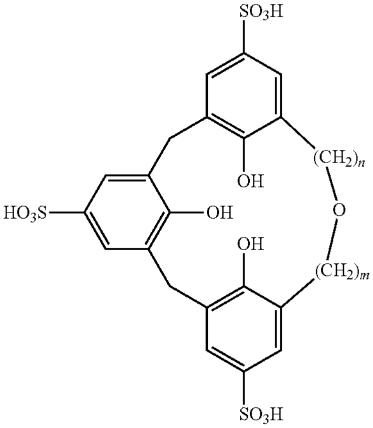 |
| SCA-751 | 3-sulfocalix[3]-alkyl-arene; (n = 1-6) | 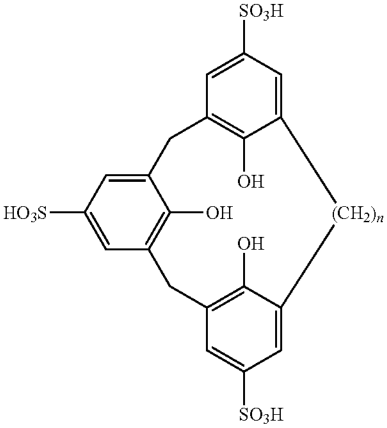 |
| SCA-753 | Tetrasodium 25,26,27,28-tetrahydroxycalix(4)arene-5,11,17,23-tetrasulfonate or Tetrasodium calix[4]arenetetra-p-sulfonate | |
| SCA-754 | Trisodium 25,26,27,28-tetrahydroxycalix(4)arene-23-methyl-5,11,17-trisulfonate | 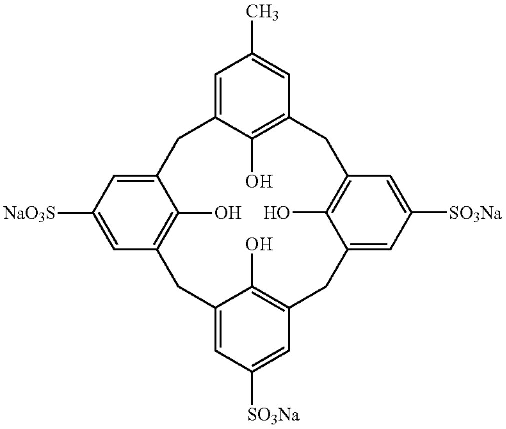 |

TABLE-continued
| Preferred compounds | | |
|---|---|---|
| Compound | Name | Formula |
| SCA-755 | Trisodium 25-methoxy-26,27,28-trihydroxycalix(4)arene-2,3-methyl-5,11,17-trisulfonate | 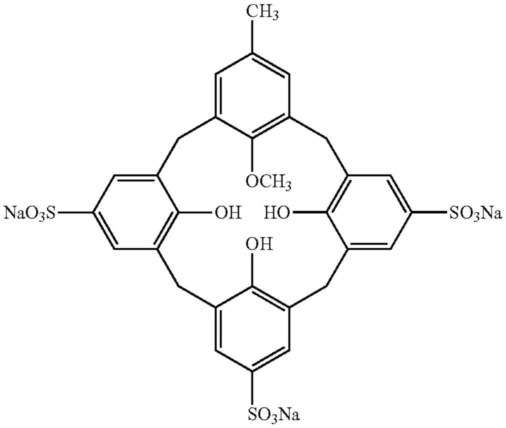 |
| SCA-756 | Tetrasodium 25-methoxy-26,27,28-trihydroxycalix(4)arene-5,11,17,23-tetrasulfonate | 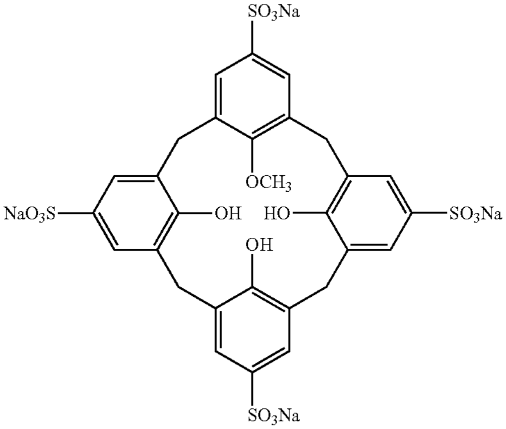 |
| SCA-757 | Tetrasodium 25,26,27,28-tetrahydroxycalix(4)arene-23-carboxyl-5,11,17-trisulfonate | 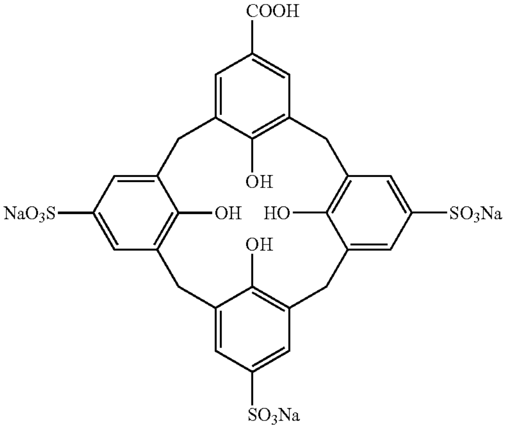 |

TABLE-continued

| Preferred compounds | | |
| --- | --- | --- |
| Compound | Name | Formula |
| SCA-758 | Trisodium 24,25,26-trihydroxycalix[1]pyrrole[3]arene-5,11,17-trisulfonate | 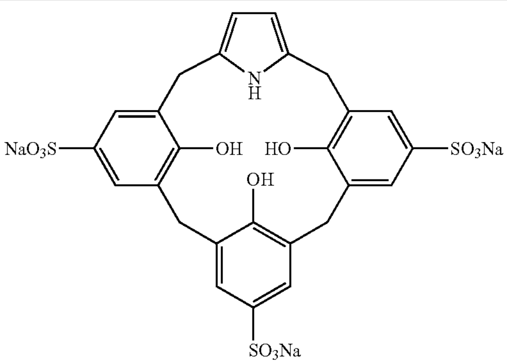 6 |

The compounds described herein are understood to comprise a calixarene ring.

Role in Disease

The compounds described herein (or pharmaceutically acceptable salts thereof) have potential as new medicines in treatment (therapy or prophylaxis) of anti-inflammatory diseases, anti-oxidative diseases, anti-ageing diseases, neurodegenerative diseases or diseases of lipid metabolism. This includes diseases currently treated with glucocorticoids (examples such as rheumatoid arthritis, inflammatory bowel diseases, osteoarthritis, asthma, auto-immune diseases). The compounds or their pharmaceutically acceptable salts have potential as replacement of or adjunctive therapy to existing glucocorticoid treatment. In particular, SCA-744 and SCA-745 have been shown to affect anti-inflammatory pathways overlapping with those involved in the action of glucocorticoids (cortisol), but not certain metabolic pathways involved in the side-effects of glucocorticoids.

Further, SCA-744 has been shown to suppress pro-inflammatory gene products, such as IL-1β, TNFα and IL-6, similarly to cortisol, even in a non-septic model. Most of the metabolic pathways affected by cortisol and the compound are shared. However, several metabolic pathways affected by cortisol and involved in its side-effects are not modulated by the compound (e.g. sugar metabolism and neurotransmitter deactivation pathways). In addition, several beneficial effects, such as a potent anti-oxidant and cytoprotective responses are evoked by the compound, not induced by cortisol. SCA-744 is therefore a potential novel anti-inflammatory product candidate with additional activities in anti-oxidative stress response, favorable changes in lipid metabolism and activating anti-aging genes.

Heparan Sulfate Mimicking

One potential mechanism of SCA-744 is through mimicking heparan sulfate (HS) and binding to HS-interacting molecules. Heparan sulfate mimetics include any molecule which can perform at least one biological function of heparan sulfate. Previous data indicates that there are highly specific structural requirements for heparan sulfate mimetic to maintain cell viability and homeostasis (Ziolkowski et al.; Journal of Clinical Investigation 2012, 122(1), pp. 132-141). Compounds which are active HS mimetics could be identified which may be used for clinical uses beyond the current clinical application of heparin, a heparan sulfate mimetic.

Heparan sulfate is a glycosaminoglycan covalently bound to proteins and forming heparan sulfate proteoglycanes (HSPG) on most cell surfaces. It is an important component of the extracellular matrix (ECM), where HS binds diverse molecules, including growth factors, cytokines and chemokines, enzymes and enzyme inhibitors, and may promote or inhibit their activity. HS have been also found to aid the formation of receptor complexes. Heparan sulfate binding proteins (HSBP) are proteins, which under normal physiological conditions interact with the heparan sulfate chain of extracellular proteoglycans. The HSBPs include plasma proteins, extracellular matrix components, cell surface proteins, and members of the major growth factor and signaling protein families including Wnt, hedgehog, osteopontin, fibroblast growth factor and vascular endothelial growth factor families (Billings and Pacifici, Connect Tissue Res. 2015, 56(4), pp. 272-280).

The ECM is a multi-dimensional network of macromolecules and polymers composed of collagens, proteoglycans/glycosaminoglycans (GAG), elastin, fibronectin, laminins and several other glycoproteins with sensory and mechanical properties. The ECM components bind to each other, creating micro-environments, as well as binding to cell adhesion receptors to form a complex network into which cells reside in all tissues and organs in a multidimensional system of cells and macromolecules. This environment is fundamental for cell behaviour and tissue homeostasis and plays a vital role in maintaining and controlling cell structure and function such as survival, growth, activation, migration and differentiation. The ECM can directly bind different types of cell surface receptors or co-receptors, thus mediating cell anchorage and regulating several pathways involved in intracellular signalling and mechanotransduction as well. Proteoglycans are essential structural and functional biomacromolecules in the ECM. Disregulation of ECM composition and structure is associated with the development and progression of several pathologic conditions, several of the mechanisms associated with the role of HS and HSPG in the ECM (Theocharis et al. Advanced Drug Delivery Reviews 2016, 97:4-27).

HS in Inflammation

HS has a well-studied role in inflammation (Collins and Troeberg; Journal of Leukocyte Biology 2018, 105(1), pp. 81-92). On one hand, it binds to various chemokines, thereby concentrating them on cell surfaces and forming a gradient to attract leukocytes towards inflammation site. On the other hand, binding of cytokines to ECM HS has been suggested as a mechanism for concentrating cytokines close to their site of action, protecting them from proteolytic degradation and forming a reservoir for certain cytokines. Besides the role of HS in inflammation through its interaction with chemokines and cytokines, soluble fragments of HS were shown to directly signal through the innate pattern recognition receptor, TLR4. An additional proposed mechanism for the role of ECM HS in inflammation and diseases is through the activity of heparanase. Heparanase is a b-D-endoglucuronidase that cleaves HS, facilitating degradation of ECM and the release of HS-bound biomolecules including e.g. certain cytokines.

HS is also involved in inflammation through its interaction with the HSBP, osteopontin (OPN). OPN is a secreted, sialic acid-rich, chemokine-like protein and a member of the SIBLING (small integrin-binding ligand N-linked glycoproteins) family. Previous work done in our group showed the binding site of HS to OPN by solution NMR. This work showed that the heparin-binding site was mapped to the central integrin-binding domain of OPN comprising the RGD motif. Osteopontin was shown to mediate several functions; through its interaction with integrins and its action as a Th1 cytokine, it is involved in chronic inflammation. Additionally, it is also a regulator of biomineralization.

As a consequence, HS mimics have large potential in regulating inflammatory processes through altering interaction between HS/HSPG and its binding proteins.

A specific anti-inflammatory effect or activity of a compound is proven, if the compound can decrease the production of one of IL-1B, IL-6 and TNFα in human THP1 macrophages following LPS stimulation, as determined by a standard assay: THP-1 human monocytic cell lines are treated with 100 nM of Phorbol 12-myristate 13-acetate (PMA) for 48 h to induce mature macrophage-like state. Cells are then stimulated with 100 ng/ml of LPS in the absence and presence of 500 μM of compound. After 6 hours, supernatants of treated and untreated cells are collected, and cytokine levels determined using the Human Inflammatory panel LEGENDplex Human Pro-inflammatory Chemokine Panel (Cat. No. 740118). A positive result is considered if the compound is capable of reduce or block the production of IL-1β, IL-6, and TNFα in human THP1 macrophages after LPS stimulation.

HS in Neurodegenerative Diseases

Protein aggregation drives many neurodegenerative diseases. Although the proteins that aggregate vary with the diseases, they show structural similarities, including beta-sheet rich fold, forming amyloid fibrils. These fibrils trigger further incorporation of monomeric proteins into the fibrils by auto-catalysis (known as "seeding") and propagation of diseases. HS was demonstrated to play a multifaceted role in the pathogenesis of neurodegenerative diseases including, but not limited to taupathies (Alzheimer's disease (AD), progressive supranuclear palsy (PSP) and Pick's disease) (Naini and Soussi-Yanicostas. Front Cell Dev Biol. 2018; 6:163), Parkinson disease, Lewy Body dementia, amyotrophic lateral sclerosis (ALS) and prion diseases (Maiza et al, FEBS Letters 2018; 592:3806-3818). An abnormal HSPG accumulation is often observed at early stages of the neurodegenerative diseases, like Down-syndrome associated dementia and Alzheimer's disease and all investigated extracellular amyloids were shown to contain HS (e.g. both amyloid-beta (Aβ) plaques and neurofibrillary tangles (NFTs) in Alzheimer's disease) (Snow et al. Lab Invest. 1987; 56:120-3.). The interaction likely happens through negatively charged groups in HS with positively charged amino acids in the amyloid protein leading to fibril formation and stabilization of the aggregates.

In taupathies heparin was also shown to enhance the phosphorylation of tau by different protein kinases, leading to tau hyperphosphorylation (potentially through conformational changes induced, which expose previously masked tau phosphorylation sites). Importantly cell surface HS also act as receptors for amyloid ß (Aß) and tau aggregates and increase cell internalization. In summary, HS potentially plays a role in the initiation and propagation of taupathies and may also play a role in limiting regenerative potential in dementia-susceptible regions, therefore targeting HS and HSPG by HS analogs and blocking its function in taupathies have potential in preventing and treating or reversing the diseases.

In Parkinson disease pathogenesis it was shown that internalization of α-synuclein (in the form of amyloid fibrils) depends on HSPGs and HS has an important role in the seeding process in oligodendrocytic cells (Ihse et al. Scientific Reports; 2017, 7:9008; doi: 10.1038/s41598-017-08720-5). Therefore, interfering with HSPG interaction with a-synuclein by HS analogs have potential beneficial activity in the disease.

Although the exact mechanisms involved in the development of ALS are not fully elucidated, HSPGs were shown to be involved in concentrating secreted type I NRG1 to certain regions (due to a specific HS binding site on NRG1) and may contribute to abnormal signaling (Song et al. Journal of Neuropathol Exp Neurol. 2012; 71:104-115).

HS in Lipid Metabolism

Interactions with HS and HSPGs have been shown to regulate the distribution and action of hedgehog (Hh) proteins on target cells and tissues. The Hh signalling is essential for development, proliferation and stem cell maintenance. The Hh proteins are secreted ligands, which enable long-range communication between cells of developing and adult tissues. Lipid metabolism has a profound influence on both hedgehog signal transduction and the properties of the ligands themselves, leading to changes in the strength of Hh signalling and cellular functions. The link between lipid metabolism and Hh signalling is related to LDL receptor (LDLR) and INSIG1 expression (Ali et al. Arthritis Rheumatol. 2016 January; 68(1): 127-137). The HSPGs that have been associated with Hh signalling usually have protein cores composed of either syndecan-3 or glypicans. These macromolecules are attached to cell surface membranes, usually by a transmembrane domain or a GPI-anchor. Hh interacts with HSPGs through a highly conserved Cardin-Weintraub sequence found in its N-terminus, creating an electrostatic interaction between the negatively charged sulfates of the HSPGs and Hh. HSPGs have been found to interact with other extracellular matrix factors as well, that mediate interactions with Hh, such as Shf, as well as lipid-modified Hh carried in large punctate structures (Farzan et al. American Journal of Physiology-Gastrointestinal and Liver Physiology 2008, 294(4), pp. G844-G849). Through regulating Hh signalling, HS can play a role in altering lipid metabolism as well. HS mimics therefore have a potential to decrease lipid blood levels through altering Hh regulated proteins involved in cholesterol metabolism.

Additionally, HS has been attributed multiple roles in the development of atherosclerosis through interacting with lipoprotein lipase and with growth factors such as fibroblast growth factor (FGF-2) and platelet-derived growth factors (PDGFs).

A specific lipid metabolism modulating effect or activity of a compound is proven, if can increase the expression of LDLR protein in mammalian cells, as determined by a standard assay:

A specific lipid metabolism modulating effect or activity of a compound is proven, if a compound can increase the expression of LDLR protein in mammalian cells extracts after treatments with 50, 100 and 500 [μM] of the tested compound. The expression levels of LDLR is determined by: Confocal laser-scanning microscopy and Western blot analysis. Whole cell images and fluorescence intensity was estimated by the fluorescence signal of the pair LDL-R antibody (C7: sc-18823, Santa Cruz Biotechnologies) and AlexaFuor Plus 488 (A3273, Invitrogen). A positive result is considered if the compound is capable to induce LDLR expression in mammalian cells extracts and increase of the LDRR signal by confocal microscopy imaging.

HS in Ageing

It has been shown that there is an age-related change in the structure of HS (Feyzi et al., Journal of Biological Chemistry 1998, 273(22), pp. 13395-13398) which alters interaction with HSBPs. These changes may be involved in the complex pathogenesis of aging.

Anti-Oxidative and Aging Related Mechanism

There are three major enzymes involved in the oxidative stress response; CHAC1 (Gene ID: 79094); Glutathione-specific γ-glutamylcyclotransferase 1), implicated in oxidative stress and apoptosis, 2., NQO1 (Gene ID: 1728); NAD(P)H dehydrogenase [quinone] 1), involved in detoxification pathways and 3., SLC7A11 (Gene ID: 23657); Cysteine/Glutamate transporter; xCT, CCBR1), producing reduced form of extracellular CySS (result of cystein oxidation), independent of the Glutathione (GSH) system.

The NQO1 protects cells against oxidative stress and toxic quinones. It is one of the two major quinone reductases in mammalian systems. It is highly inducible and plays multiple roles in cellular adaptation to stress. NQO1 is found in the cytosol, Golgi complex, nucleus, mitochondria, cellular membrane and endoplasmic reticulum. It is well known that mitochondria are central to the regulation of apoptosis. Loss of mitochondrial membrane potential is catastrophic for cells and also leads to the release of cytochrome C into the cytosol (Weinberg & Chandel, Nature Chemical Biology 2015, 11(1), pp. 9-15).

NRF2 can mediate the strong induction of NQO1. NRF2 is a basic region-leucine zipper (bZip) transcription factor, which forms heterodimers in the nucleus that recognises the enhancer sequence termed as antioxidant response element (ARE). Several studies have demonstrated that NRF2 contributes to the anti-inflammatory process through ARE and a cross talk with the NF-kβ pathway (Ahmed et al. Molecular Basis of Disease 2017, 1863(2), pp. 585-597). The NRF2 activation induces HO-1 gene by increasing mRNA and protein expression, inhibiting the NF-kβ signalling pathway and suppressing pro-inflammatory cytokines. Additionally, inflammation is associated with increased local and systemic accumulation of pathological levels of reactive oxygen species (ROS) that may impair redox signalling, increasing the oxidative stress. This situation impacts the mitochondria generating uncontrolled activation of NADPH oxidase representing the main contributors to heightened ROS production in inflammatory cells. Mitochondrial ROS cause damage and release of mitochondrial DNA (mtDNA), thus creating a vicious cycle of events leading to further ROS production and activation of the inflammasome, ultimately resulting in organ debilitation (Kovac et al. Biochimica et Biophysica Acta. BBA 2015, 1850(4), pp. 794-801). The NRF2 affects intermediary metabolism, increases the availability of substrates, reduces equivalents for the mitochondrial respiratory chain, as well as maintains integrity of mtDNA (Holmstrom, K. M., Baird, L., Zhang, Y., Hargreaves, I., Chalasani, A., Land, J. M., et al. (2013). *Biology Open,* 2(8), 761-770.) Drugs and drug candidates enhancing NRF2 and NQO1 expression exert anti-oxidative effect and protect cells from oxidative stress.

CHAC1: Glutathione-specific gamma-glutamylcyclotransferase 1, plays a role in the unfolded protein response, in regulation of glutathione levels and oxidative balance and promotes neuronal differentiation.

Cysteine/Glutamate transporter, leading to reduced extracellular CySS (oxidised form of cysteine), is independent of the Glutathione (GSH) system. Down regulation promotes ferroptosis and ageing (Zhang et al. Nature Cell Biology 2018, pp. 1-19).

Additionally, DHCR24 (Gene ID: 1718), 3beta-hydroxysterol-Delta24 reductase) also known as SELADIN1 (Selective Alzheimer Disease Indicator 1), protects cells from oxidative stress by reducing caspase 3 activity during apoptosis induced by oxidative stress and amyloid-beta. It also catalyses the last step of cholesterol synthesis and therefore is involved in lipid metabolism as well.

Genes for the LDLR (Gene ID: 3949), INSIG1 (Gene ID: 3638) and DHCR24/Seladin-1 (Gene ID: 1718) were found to be modulated by a compound described herein, in particular SCA-744.

A specific anti-oxidative effect or activity of a compound is proven, if induces the expression of NQO1 in mammalian cells to a higher level than over vehicle treated cells, preferably by ~3 fold when the compound is used at 500 μM, as determined by a standard assay: Semi-quantitative western blot analysis. HeLa cells are treated with vehicle, 50, 100 and 500 μM of the compound for 48 h and lysed in Triton X-100 extraction buffer (50 mM HEPES [pH 7.4], 140 mM NaCl, 1% Triton X-100, 1 mM EDTA, 0.3 mM DTT and Complete Protease Inhibitor Cocktail). 25 μg of whole cell extract are separated on a 10% SDS-PAGE, after transfer to a PVDF membrane (Bio-Rad), proteins detected by use of standard immunoblotting procedures. The membrane is incubated with (1:200) dilution of NQO1 (A-5: sc-271116, Santa Cruz Biotechnologies) primary antibody followed by 1:3000 of goat anti-mouse (IgG-HRP: sc-2005). For the loading control GAPDH Antibody is used (0411: sc-47724). NQO1 protein signal intensity is estimated relative to GAPDH showing an increase of NQO1 at least 3-fold over the signal for vehicle treated cells when the compound is used at 500 μM. For the analysis and quantification of the protein levels, Gel Analyzer from ImageJ (National Institute of Health, USA: http://imagej.nih.gov/ij) is used.

Anti-Ageing Processes

Chronic inflammation, oxidative stress and unfavourable lipid metabolism changes are important elements of aging. The mechanisms described above all contribute to the process and drugs and drug candidates altering the combination of those processes may have a potential as anti-aging drugs.

NRF2 (Gene ID: 4780) one of the best-characterised anti-ageing genes is an example demonstrating the relationship between inflammation and oxidative stress and aging. It is a transcription factor, which regulates the expression of electrophilic response elements, as well as antioxidants, in response to increased levels of reactive oxygen species, either external or produced during metabolism or inflammation. Activators, e.g., sulforaphane (dietary compound) and more potent synthetic analogues are in clinical development. For example, rapamycin increases life-span of all living organisms tested; it inhibits mTOR and is shown to increase transcription of the NRF2. Activation typically occurs through its binding partner KEAP1 in the cytoplasm. The NRF2 activation involves increased half-life and translocation to the nucleus, where it binds to promoters of its target genes.

A specific anti-aging effect or activity of a compound is proven, if induces the expression of the following genes NQO1, LDLR, simultaneously and the inhibition of the pro-inflammatory chemokines; IL-1β, IL-6, TNFα, as determined by a standard assay: Semi-quantitative western blot analysis. For the analysis and quantification of the protein levels, Gel Analyzer from ImageJ (National Institute of Health, USA: http://imagej.nih.gov/ij) is used.

For the detection of NQO1 and LDLR, HeLa cells are treated with vehicle, 50, 100 and 500 μM of the compound for 48 h and lysed in Triton X-100 extraction buffer (50 mM HEPES [pH 7.4], 140 mM NaCl, 1% Triton X-100, 1 mM EDTA, 0.3 mM DTT and Complete Protease Inhibitor Cocktail). 25 μg of whole cell extract is separated on a 10% SDS-PAGE, after transfer to a PVDF membrane (Bio-Rad), proteins detected by use of standard immunoblotting procedures. The membrane is incubated with (1:200) dilution of NQO1 (A-5: sc-271116, Santa Cruz Biotechnologies) or LDLR antibody (C7: sc-18823, Santa Cruz Biotechnologies) primary antibodies followed by 1:3000 of goat anti-mouse (IgG-HRP: sc-2005). For the loading control, GAPDH Antibody (0411: sc-47724). NQO1 protein signal intensity is estimated relative to GAPDH should show an increase of at least 3-fold over control. Simultaneously, the compound must have anti-inflammatory activity by decreasing the production of; IL-1β, IL-6 and TNFα in human THP1 macrophages. THP-1 human monocytic cell line is treated with 100 nM of Phorbol 12-myristate 13-acetate (PMA) for 48 h to induce mature macrophage-like state. Cells are then stimulated with 100 ng/ml of LPS in the absence and presence of 500 μM of SCA-744. After 6 hours, supernatants of treated and untreated cells were collected, and cytokine levels were determined using the Human Inflammatory panel LEGENDplex Human Pro-inflammatory Chemokine Panel (Cat. No. 740118).

Medical Use

The invention contemplates treatment (treatment for e.g. prophylaxis or therapy) of a human or non-human animal subject in a series of indications which can be treated by a specific mimic of any one or more of a corticosteroid, heparan sulfate, or heparin. Specifically, a compound is selected which acts as a mimic of any one or more of a corticosteroid, heparan sulfate, or heparin.

The term "treatment" as used herein with respect to treating subjects refers to medical management of a subject with the intent to cure, ameliorate, stabilize, reduce the incidence or to prevent a disease, pathological condition, or disorder, which individually or together are understood as "disease condition". The term includes active treatment, directed specifically toward the improvement of a disease condition, prophylaxis directed specifically toward the prevention of a disease condition, and also includes causal treatment directed toward removal of the cause of the associated disease condition. In addition, this term includes palliative treatment designed for the relief of symptoms rather than the curing of the disease condition, and further curing a disease condition directed to minimizing or partially or completely inhibiting the development of the associated disease condition, and supportive treatment employed to supplement another specific therapy directed toward the improvement of the associated disease condition.

Specifically, a compound is used which a) reduces expression of one or more proinflammatory cytokines, preferably selected from the group consisting of IL-1β, IL-6, TNFα; or of one or more proinflammatory genes selected from the group consisting of IKZF1, GDF10, SPOCK3, MMP1, IL-1B, KCNMA1, CCL7, AQP1, ITIH5, ABI3BP and BMP5;
b) increases expression of one or more anti-oxidative genes, preferably selected from the group consisting of CHAC1, SLC7A11, NQO1, EGR1, SGK1, SLC6A9 and DHCR24, preferably NQO1;
c) increases expression of any one or more of LDLR, ID3, NQO1, SLCGA2, or DHCR24; or
d) modulates the expression of enzymes involved in cholesterol metabolism, preferably LDLR or DHCR24.

Specifically, the treatment described herein comprises administering to the subject an effective amount of the compound or a pharmaceutically acceptable salt thereof, sufficient to a) reduce expression of one or more proinflammatory cytokines, preferably selected from the group consisting of IL-1β, IL-6, TNFα; or of one or more proinflammatory genes selected from the group consisting of IKZF1, GDF10, SPOCK3, MMP1, IL-1B, KCNMA1, CCL7, AQP1, ITIH5, ABI3BP and BMP5;
b) increase expression of one or more anti-oxidative genes, preferably selected from the group consisting of CHAC1, SLC7A11, NQO1, EGR1, SGK1, SLC6A9 and DHCR24, preferably NQO1;
c) increase expression of any one or more of genes involved in lipid metabolism, preferably any one or more of LDLR, ID3, NQO1, SLCGA2, or DHCR24; or
d) modulate the expression of enzymes involved in cholesterol metabolism, preferably LDLR or DHCR24.

Specifically, the invention provides use of the compounds for treating diseases and medical conditions which compounds have proven anti-inflammatory, anti-oxidative, anti-ageing, or lipid metabolism modulation properties. The use of such compounds (or pharmaceutically acceptable salts thereof) or respective preparations allows treating a subject e.g. a patient diagnosed with or at risk of developing an inflammatory disease or disorder, a disease or disorder associated with oxidative stress or increased production of oxygen radical generation, an ageing disease or disorder, or a lipid metabolism disease or disorder.

Specifically, the inflammatory disease is acute or chronic inflammatory disease.

According to a specific aspect, the inflammatory disease is pneumonia, in particular pneumonia caused by toxic inhalation or an infectious pathogen, such as viral pneumonia, bacterial pneumonia, parasitic pneumonia. Specifically, the inflammatory disease is pneumonia, such as acute pneumonia, in particular to treat perivascular oedema, or immune cells infiltration in pneumonia.

According to a specific aspect, the inflammatory disease is acute respiratory distress syndrome, such as caused by a virus, or chronic obstructive pulmonary disorder.

According to a specific aspect, the inflammatory disease is a disease condition, inflammation or an inflammatory symptom condition occurring with autoimmune disease or allergy, such as joint inflammation, inflammatory bowel disease, or any inflammatory disease condition associated with rheumatoid arthritis, osteoarthritis, asthma, or psoriasis.

Specifically, the inflammatory disease is joint inflammation or inflammatory bowel disease.

Specifically, the inflammation is not sepsis-related, and in particular not sepsis, bacterial sepsis, LPS-induced shock, septic shock or multi-organ failure.

Exemplary diseases and conditions include those, a) wherein the inflammatory disease is acute or chronic inflammatory disease, any of the inflammatory disease conditions occurring with autoimmune disease or allergy; pneumonia, pneumonia caused by toxic inhalation or an infectious pathogen, such as viral pneumonia, bacterial pneumonia, parasitic pneumonia; acute respiratory distress syndrome, joint inflammation, inflammatory bowel disease, or any inflammatory disease condition associated with rheumatoid arthritis, osteoarthritis, asthma, allergy, chronic obstructive pulmonary disorder or psoriasis;

b) wherein the anti-oxidative stress disease is ischeamia reperfusion injury; or c) wherein the ageing disease is progeria syndrome; and d) wherein the lipid metabolism disease is hyperlipideamia or atherosclerosis.

Alternative inflammatory diseases include Chron's disease, Colitis ulcerosa, Sjögren syndrome, vasculitis, dermato (poly) myositis, Graves disease, multiple sclerosis, sarcoidosis, systemic lupus erythematosus, myasthenia gravis, immune thrombocytopenia, anterior uveitis, Duchenne muscular dystrophy, Becker muscular dystrophy, and eczema.

Alternative anti-oxidative stress diseases include heart attack, stroke, hepatic/intestinal ischemia and atherosclerosis.

Alternative ageing diseases include Hutchinson-Gilford syndrome and Werner syndrome.

Alternative indications include Alport syndrome, autosomal dominant polycystic kidney disease, IgA nephropathy, type 1 diabetic CKD, focal segmental glomerulosclerosis, Friedreich's ataxia.

The term "subject" as used herein refers to any animal, which herein preferably includes any mammal and particularly a human being, for whom diagnosis, screening, monitoring or treatment is contemplated. A subject may be at risk of a certain disease condition, e.g. a patient afflicted with a disease condition or for which a disease condition is to be determined or risk of a disease condition is to be determined. The term "patient" as used herein always includes healthy subjects.

The term "at risk of" a certain disease conditions, refers to a subject that potentially develops such a disease condition, e.g. by a certain predisposition, or already suffers from such a disease condition at various stages, including the congenital or acquired state, including transient disease, particularly associated with other causative disease conditions or else conditions or complications following as a consequence of such immunoglobulin deficiency. The risk determination is particularly important in a subject, where a disease has not yet been diagnosed. This risk determination therefore includes early diagnosis to enable prophylactic therapy. Risk assessment may be performed by single, preferably by multiple risk parameters such as genetic background, stress level, ingestion of certain drugs etc. Specifically, the preparation of the invention is used in patients with a high risk, e.g. a high probability of developing disease.

Specifically, a preparation described herein is provided for medical use and a respective treatment, which comprises oral, topical, mucosal or parenteral administration of an effective amount of said preparation to exhibit said anti-inflammatory, anti-oxidative, anti-ageing, or lipid metabolism modulation activities.

Specifically, a preparation described herein is provided for medical use and a respective treatment, wherein the treatment regimen comprises substitution or combined administration of any of a corticosteroid, an anti-TNFα inhibitor, an IL-17 inhibitor, an IL-23/IL-12 inhibitor, a PDE4 inhibitor, Fumaric Acid, a JAK kinase inhibitor methotrexate, lefunomide, hydroxcloroquinie, sulfasalazine, cyclosporin or a dissociative steroid compound.

According to a specific embodiment, the preparation is a pharmaceutical composition formulated for oral, topical, mucosal or parenteral administration.

The term "formulation" as used herein refers to a preparation ready-to-use for treating a subject in a specific way. Specifically, the pharmaceutical composition comprises the compound further described herein, or a pharmaceutically acceptable salt thereof, and a pharmaceutically acceptable diluent, carrier or excipient.

According to a specific aspect, pharmaceutical formulations are provided comprising the compound described herein or a pharmaceutically acceptable salt thereof or respective preparations, in pharmaceutically acceptable vehicles for oral, topical, mucosal or parenteral administration. Also, the present disclosure includes such compounds, or salts thereof, which have been lyophilized and which may be reconstituted to form pharmaceutically acceptable formulations for administration, e.g., by intravenous, intramuscular, or subcutaneous injection. Administration may also be intradermal or transdermal.

Specific embodiments refer to formulations which are orally administered or through inhalation as a solid, or may be administered intramuscularly or intravenously as a solution, suspension or emulsion. Alternatively, the formulations may also be administered by inhalation, intravenously or intramuscularly as a liposomal suspension.

To administer the compound described herein or a pharmaceutically acceptable salt thereof or respective preparations by any route other than parenteral administration, it may be necessary to coat the active agent with, or co-administer the active agent with, a material to prevent its inactivation. For example, an appropriate carrier may be used, for example, liposomes, or a diluent.

Pharmaceutically acceptable diluents include saline and aqueous buffer solutions.

A compound described herein or a pharmaceutically acceptable salt thereof or respective preparations can be orally administered, for example, with an inert diluent or an assimilable or edible carrier. For example, a preparation may be enclosed in a hard or soft-shell gelatin capsule, compressed into tablets, or incorporated directly into the subject's diet. For oral therapeutic administration, the compound described herein or a pharmaceutically acceptable salt thereof may be incorporated with excipients and used in the form of ingestible tablets, buccal tablets, troches, capsules, elixirs, suspensions, syrups, wafers, and the like. The percentage of the compound or a pharmaceutically acceptable salt thereof in the compositions and preparations may, of course, be varied. The amount of compound described herein or a pharmaceutically acceptable salt thereof in such therapeutically useful compositions is such that a suitable dosage will be obtained.

The term "mucosal" with respect to administration or application or else mucosal use of a preparation for treating a subject or a respective formulation, refers to administration via the mucosal route, including systemic or local administration, wherein an active ingredient is taken up by contact with mucosal surfaces. This includes oral, peroral, nasal, vaginal, rectal administration and formulations, e.g. liquid, syrup, lozenge, tablet, spray, powder, instant powder, granules, capsules, cream, gel, drops, suspension, emulsion or food product.

Peroral formulations may include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions may also be coated by conventional methods, typically with pH or time-dependent coatings, such that the subject agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Other compositions useful for attaining systemic delivery of a compound described herein or a pharmaceutically acceptable salt thereof or respective preparations include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose, or glidants, lubricants, sweeteners, colorants, antioxidants and flavoring agents.

A compound described herein or a pharmaceutically acceptable salt thereof or respective preparations can also be administered topically to a subject, e.g., by the direct laying on or spreading of a composition containing same on the epidermal or epithelial tissue of the subject, or transdermally via a "patch". Such compositions include, for example, lotions, creams, solutions, gels and solids. These topical compositions may comprise an effective amount, usually at least about 0.1 wt %, or even from about 1 wt % to about 5 wt %, of compound described herein or a pharmaceutically acceptable salt thereof. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Pharmaceutical compositions suitable for injectable use include sterile aqueous solutions (in particular where the compounds or pharmaceutically acceptable salts are water soluble) or dispersions and sterile powders for the extemporaneous preparation of sterile injectable solutions or dispersion. In particular, the composition is specifically sterile and fluid to the extent that easy syringability exists; it is stable under the conditions of manufacture and storage and preserved against the contaminating action of microorganisms such as bacteria and fungi.

Suitable pharmaceutically acceptable vehicles include, without limitation, any non-immunogenic pharmaceutical adjuvants suitable for oral, parenteral, nasal, mucosal, transdermal, intravascular (IV), intraarterial (IA), intramuscular (IM), and subcutaneous (SC) administration routes, such as phosphate buffer saline (PBS).

According to a specific aspect, a compound of the Formula (I) or a pharmaceutically acceptable salt thereof, may be used as food or feed product, dietary supplement or cosmetic preparation, e.g., nutraceuticals or cosmeceuticals.

Specific embodiments refer to a food, feed or cosmetic composition comprising the compound of the Formula (I), or a pharmaceutically acceptable salt thereof.

The term "food" or "food product" as described herein refers to any compound, preparation, mixture, or composition suitable for, or intended for intake by an animal (including human beings and non-human animals). This includes any compound that is a nutritional, nutraceutical or food supplement, dietary food, complete or incomplete balanced diet or supplement or medical food which is understood as nutritional or functional supplement to a food product, possibly used as a diet. Specific functional food products are selected from the group comprising cereal bars, yogurt and the like dairy products, bakery products, fruit juices and drinks in general. Typically, functional food products aid in the prevention or prophylaxis and/or treatment of disease conditions associated with pathogens, including toxins or the treatment of physiological imbalances of the body. The term shall also comprise feed or feed products, possibly used as a diet for feeding non-human animals. Food may be of organic or synthetic sources, formulated in natural or natural-like compositions including dairy products or synthetic compositions based on artificial mixtures of substances, which have been suitably purified before mixing. The food product according to the invention typically is provided in food grade quality. The grade quality is the quality characteristics of food that is acceptable to animals. This includes external factors as appearance (size, shape, colour, gloss, and consistency), texture and flavour. Quality standards also provide for an acceptable maximum amount of contaminating substances. Besides ingredient quality, there are also sanitation requirements to inactivate or deplete pathogens. It is important to ensure that the food processing environment is as clean as possible in order to produce the safest possible food for the consumer.

The term "nutraceutical" as used herein is meant to refer to any nutrients, dietary supplements and products to be included in specific diets or processed foods such as, for example, vegetable/animal oils, vitamins, cholesterol, creatine, amino acids, mineral salts, beta-carotene, flavonoids, vegetable or yeast extracts, hyaluronic acid, inositol, herbs, and all the other suitable ingredients.

The term "cosmeceutical" as used herein is meant to refer to any cosmetic products having drug-like benefits to the body such as, for example, vitamins, alfa- and beta-hydroxyl acids, lipoic acid, dimethyl amino ethanol, glycolic acid, salicylic acid, hyaluronic acid.

Specifically, a suitable preparation may be provided as a liquid, syrup, lozenge, tablet, chewing gum, spray, powder, instant powder, granules, capsules, cream, gel, drops, suspension, emulsion or food product, for example, including specific excipients or auxiliary means for providing the respective formulation.

According to a specific aspect, a suitable cosmetic formulation preparation is provided for topical application, comprising the compound described herein or a pharmaceutically acceptable salt thereof or respective preparations and a cosmetically acceptable vehicle. Specific cosmetic formulations have hydrating and preservative properties and are able to treat keratin substrates, signs of aging, skin damages due to exposition to environment agents, and are thus improving the appearance of the skin.

Treating keratin substrates is meant to aim at preserving or restoring the healthy functioning of the skin and/or hair and/or nails or any treatment that provides means to preserve or improve their appearance and/or structure. Examples of such treatments include: skin strengthening, wrinkle reduction, moisturizing, protection from any kind of aggression, in particular, protection from sun radiations and aging indicators.

Treating signs of aging is meant to refer to all the changes regarding the appearance of the skin due to aging and photo-aging. Examples of these changes include wrinkles and thin lines, floss skin, thin skin, loss of skin elasticity and/or tone, opaque skin. It also includes internal skin modifications that do not directly affect external appearance changes. An example of these internal modifications is the degradation that occurs internally to the skin due to repeated exposure to UV radiation.

Treating for improvement of the appearance of the skin is meant to refer to all phenomena that may result in a visual improvement of the skin appearance. Examples of these phenomena lead to a skin with the more beautiful, firm and smooth skin.

BRIEF DESCRIPTION OF THE FIGURES

FIG. 2 shows effect of LPS stimulation of THP-1 macrophages on IL-1ß, TNF-α, IL-6 and IL-10 production. Dose-dependent inhibition of LPS-induced TNF-α, IL-ß and IL-6 by SCA-744. Following cells were treated with [10 ng/ml] LPS in the absence and presence 10, 100 and 500 μM of SCA-744. Cytokine levels were determined by LEGENDplex™ Human Inflammation Panel assay from BioLegend. The bar heights represent the concentration means compared to LPS alone of 3 independent experiments carried out in triplicates.

FIG. 4 shows that SCA-744 significantly increases the expression of the anti-oxidative enzyme, NQO1 in HeLa cells.

FIG. 8 depicts the chemical structure of SCA-744 and heparan sulfate (HS).

FIG. 10: Tables 1, 2, 3, and 4

Table 1 shows the genes that are differentially up-regulated in SCA-744 treated human cells and related to cellular inflammatory and oxidative response, as well as to lipid metabolism.

Table 2 shows the genes that are differentially down-regulated in SCA-744 treated human cells and related to cellular inflammatory and oxidative response, as well as to lipid metabolism.

Table 3 shows all annotated metabolites with a p-value<0.05 and a log Fold-change (log FC)>1 that are differentially up-regulated in SCA-744 treated human cells and related to cellular anti-inflammatory and anti-oxidative response, as well as lipid metabolism. The metabolites are ordered by the log FC.

Table 4 shows selected metabolites regarding glucose metabolism with a p-value<0.05 and log FC<−1 that are differentially down-regulated in SCA-744 treated human cells. The metabolites are ordered by the log FC.

FIG. 11 shows parameters of respiratory lung functions impaired by exposure to endotoxin (LPS) and significantly improved by treatment with SCA-744 based on plethysmography measurement. A: Functional Residual Capacity (FRC), B: Expiratory time (Te), C: Peak Expiratory Flow rel to Te (Rpef), D: Respiratory frequency (fBPM), E: Inhalation time (Ti). Statistical analyses applied were the One-way ANOVA, followed by Dunnett's multiple comparisons test. #p<0.05, ##p<0.005 vs control (untreated), n=5-7/group.

Figure 12:
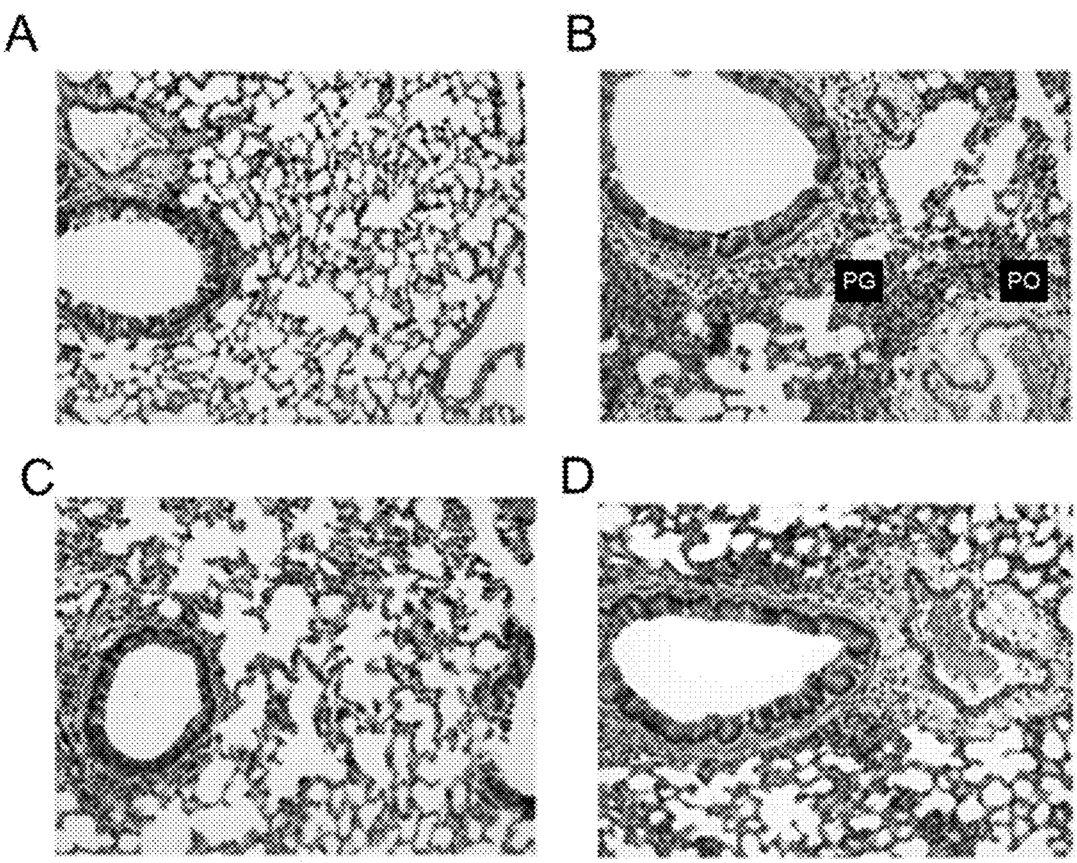

FIG. 12 shows microscopic pictures of hematoxylin and eosin stained mouse lung tissues. A: Control (untreated); B: LPS+vehicle; C: LPS+SCA-744; D: LPS+DEXA. PO: perivascular oedema, PL: perivascular/peribronchial leukocytes.

Figure 13:
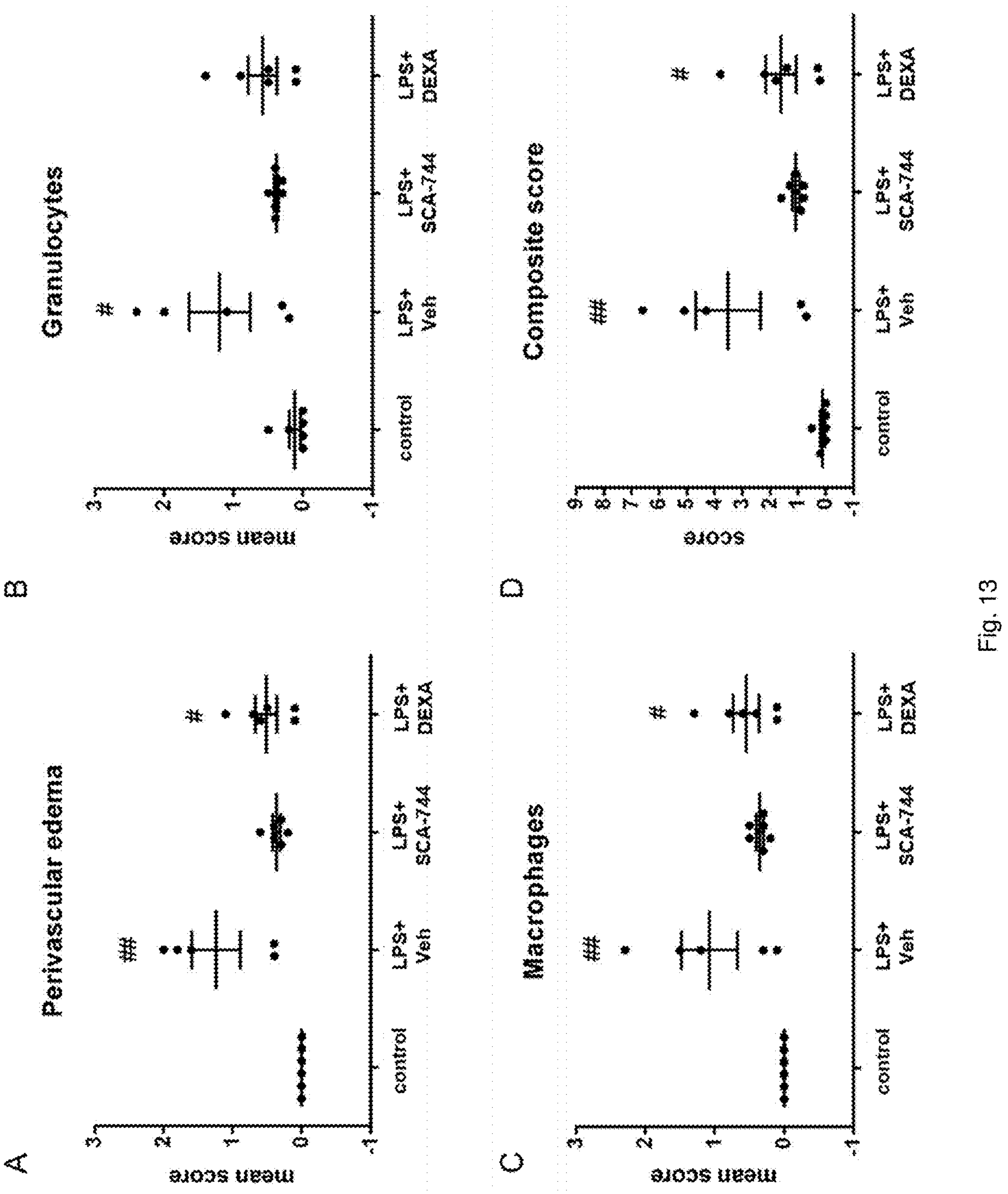

FIG. 13 shows the semiquantitative evaluation of microscopic slides on a scale from 0 to 3. 0: no change relative to untreated control; 1, 2 and 3 correspond to increasing severity of pathology. A: Perivascular oedema score; B: Granulocytes score; C: Macrophages score; D: Composite score (all three parameters combined). Statistical analyses applied were Kruskal-Wallis, followed by Dunn's multiple comparisons test. #p<0.05, ##p<0.005 compared to control (untreated) group, n=5-7/group.

FIG. 14 shows A: microscopic pictures of hematoxylin and eosin stained mouse ankle joint tissues from the negative control (sham/vehicle) and positive control (CFA-treated) groups. Arrows indicated synovial hyperplasia and B: graph with data on Synovial hyperplasia scores, where 0 is no change relative to negative control and 3 represents severe pathology seen in the positive control group. Statistical analyses applied were the Kruskal-Wallis test+Dunn's multiple comparison test. #p<0.05, ##p<0.01 compared to respective intact paw, n=5-6 mice/group.

Figure 15:
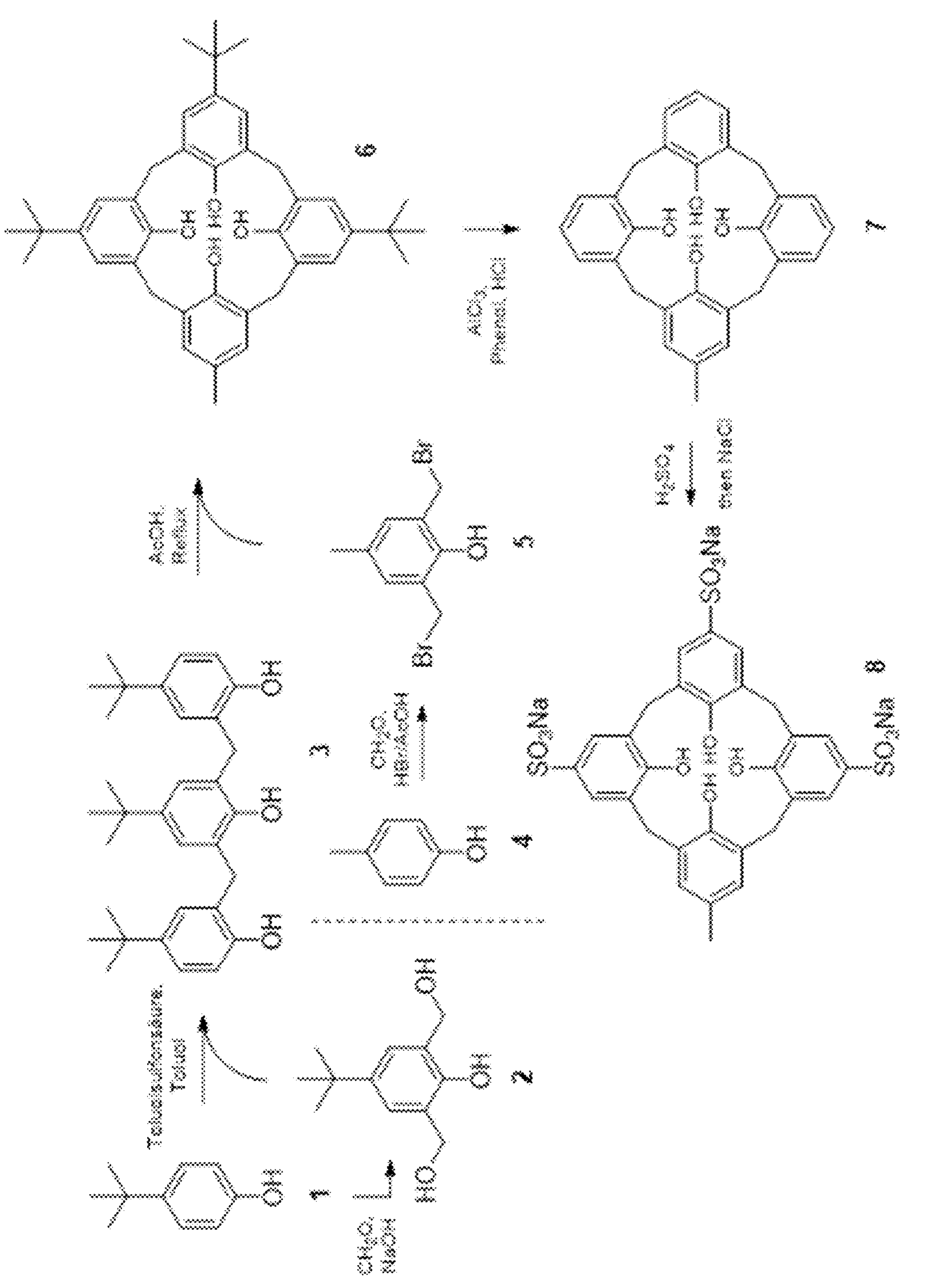

FIG. 15 Synthetic scheme for sulfocalixarene variant synthesis

Figure 16:
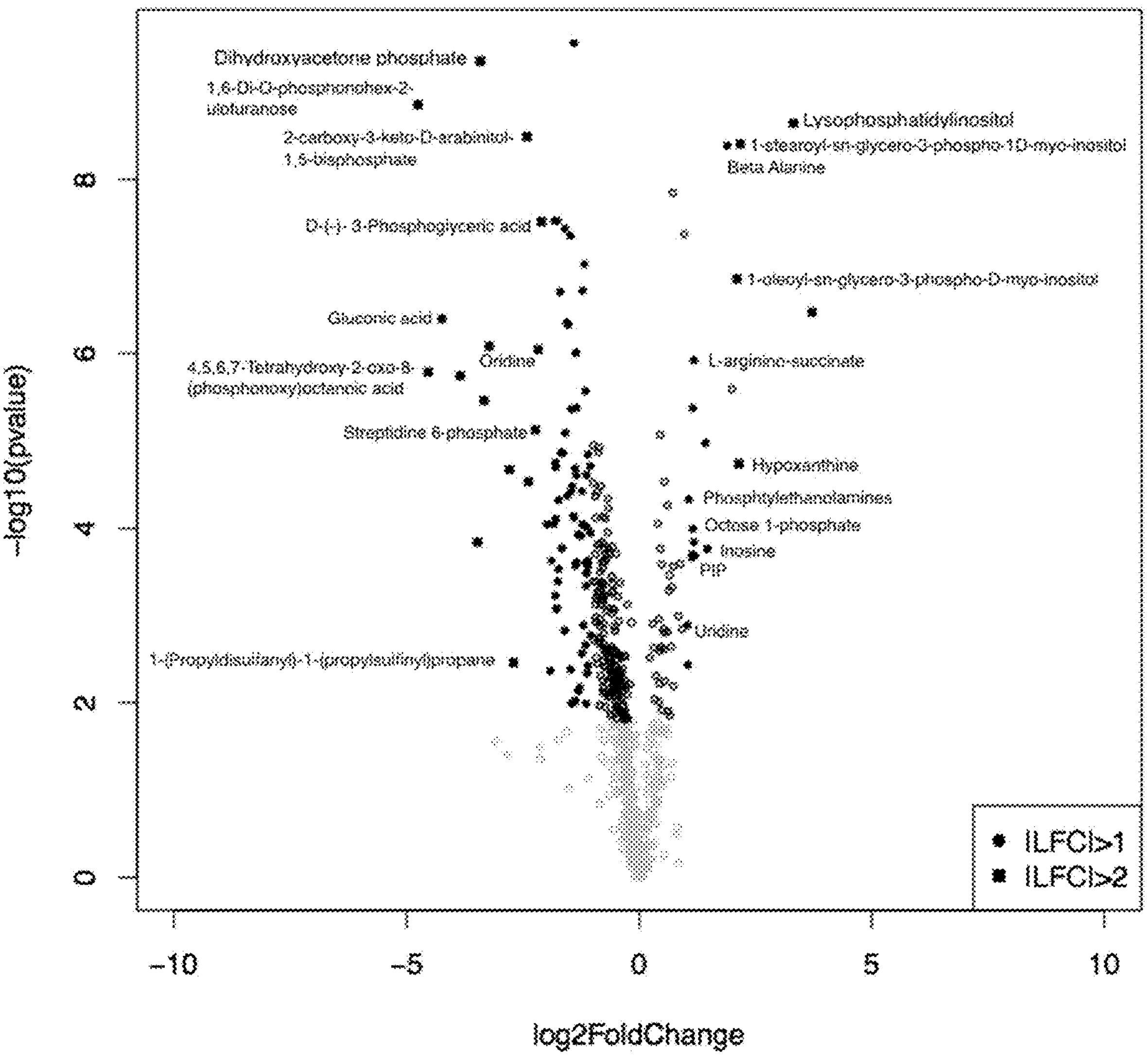

FIG. 16. Identification of key metabolites associated with cellular response to SCA-744. Up-regulated and (selected) down-regulated metabolites affected by SCA-744 with an absolute log fold>1 are labelled at the Volcano plot.

Figure 17:
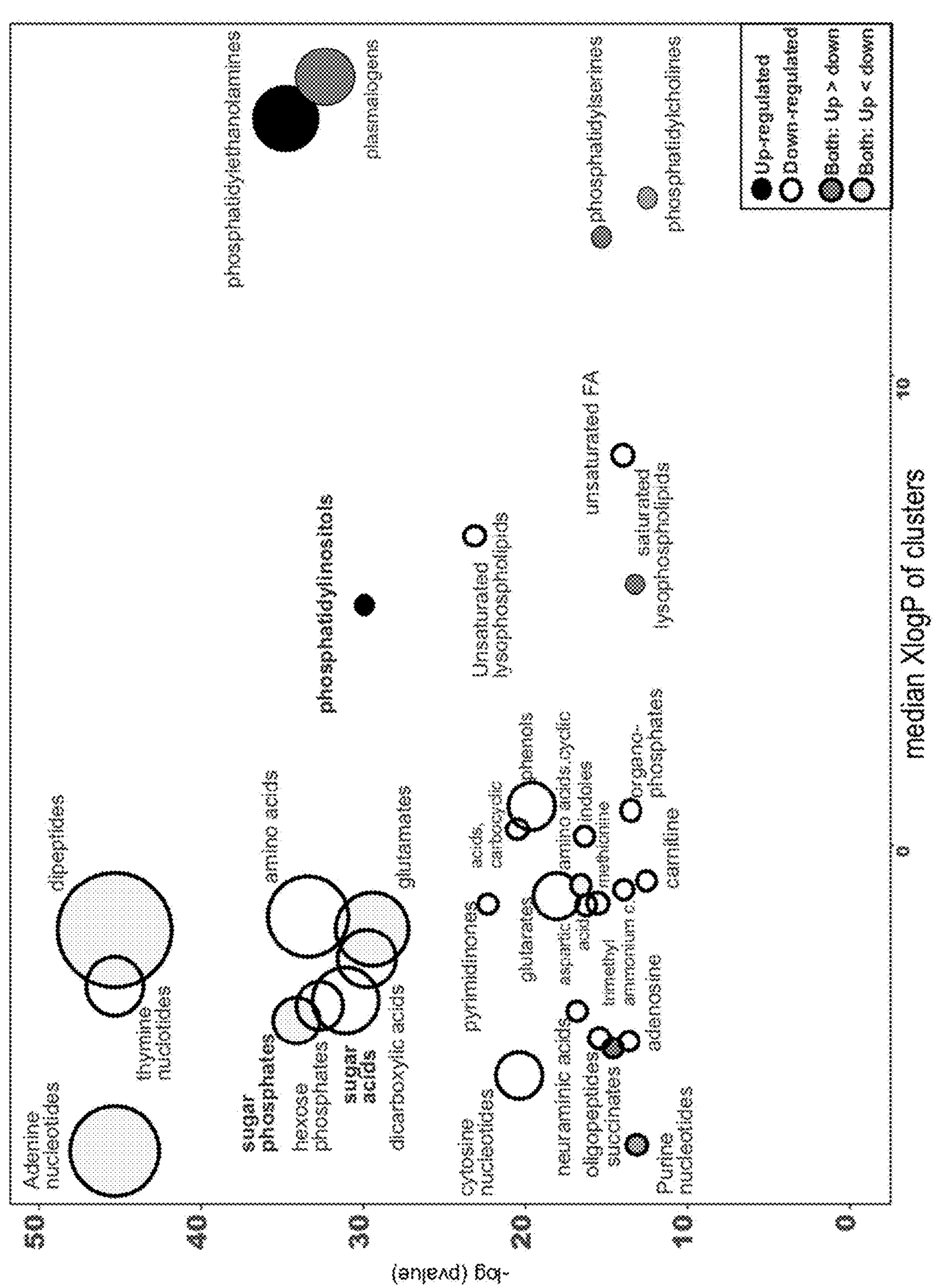

FIG. 17. Up and down-regulated metabolites enrichment plot. 261 annotated metabolites (FDR<0.05) were analysed by chemical group classification using chemical similarity enrichment analysis. Each node reflects a significantly altered cluster of metabolites. Only enrichment clusters are shown that are significantly different at p<0.05. Enrichment p-values are given by the Kolmogorov-Smirnov-test. The plot y-axis shows the most significantly altered clusters on the top. The x-axis is ordered by the cluster order on Tanimoto similarity tree. The node colour scale shows the proportion of increased (black) or decreased (white) compounds in SCA-744 compared to control human cells. Grey nodes have both increased and decreased metabolites.

Figure 18:
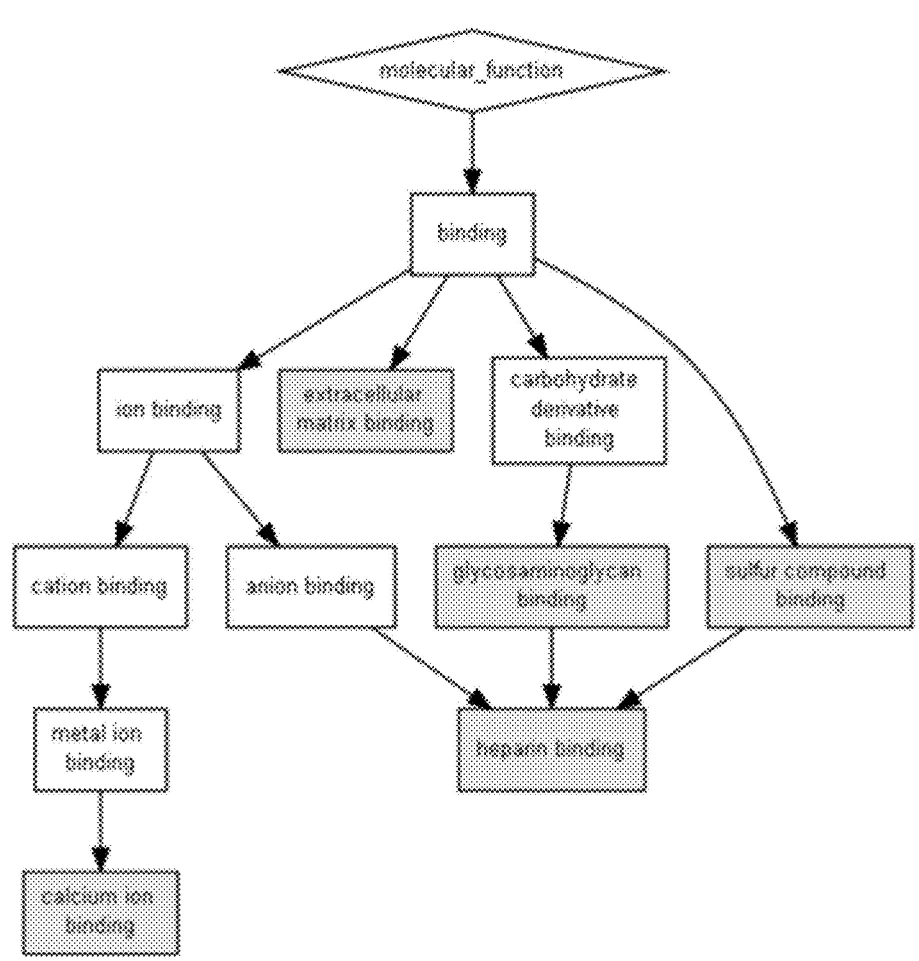

FIG. 18. Gene-ontology analysis related to molecular function. Differentially expressed genes (DEGs) were identified by applying the statistical tests of DESeq and edgeR packages. Gene-ontology was generated using Gorilla, gene ontology enrichment analysis, and visualization tool.

FIG. 19.: In-vitro assessment of SCA-744 (A) and SCA-754 (B) cytotoxicity. Experiments were performed using HEK 293 neuroblastoma cell lines. The effect of SCA-744 and SCA-754 on cell viability was assessed using a standard ATP, CellTiter-Glo® Luminescent Cell Viability Assay following 72 hours treatment. SCA-744 (C) and SCA-754 (D) protects against oxidative stress from MPP+ induced damage in mammalian cells.

FIG. 20. SCA-744 protects against oxidative stress from $H_2O_2$ induced damage in mammalian cells.

DETAILED DESCRIPTION

As used herein, the following definitions apply, unless stated otherwise:

The term “alkyl”, when used alone or in combination with other groups or atoms, refers to a saturated straight or branched chain consisting solely of a number of hydrogen-substituted carbon atoms, and includes e.g., methyl, ethyl, propyl, isopropyl, n-butyl, 1-methylpropyl, isobutyl, tert-butyl, 2,2-dimethylbutyl, 2,2-dimethylpropyl, n-pentyl, 2-methylpentyl, 3-methylpentyl, 4-methylpentyl, n-hexyl and the like.

The term “aryl” refers to an aromatic mono- or bicyclic group containing from 5 or 6 to 14 carbon atoms, preferably 6 to 10 carbon atoms, that may be optionally fused with a fully or partially saturated or unsaturated carbocyclic ring and may optionally be substituted with one or more, identical or different substituents, suitably one to three substituents. Examples of aryl groups include phenyl, naphthyl, indanyl, and the like.

The term “cycloalkyl”, when used alone or in combination with other groups or atoms, refers to monocyclic hydrocarbon rings, bicyclic hydrocarbon rings or spirohydrocarbon rings, which each may be either saturated or unsaturated (cycloalkenyl). The term unsaturated means that in the ring system in question there is at least one double bond, but no aromatic system is formed. In bicyclic hydrocarbon rings two rings are linked such that they have at least two carbon atoms in common. In spirohydrocarbon rings one carbon atom (spiroatom) is shared by two rings. If a cycloalkyl is substituted, the substitution may be mono- or polysubstitution in each case, at all the hydrogen-carrying carbon atoms, independently of one another. Cycloalkyl itself may be linked to the molecule as substituent via any suitable position of the ring system.

The term “heteroaryl” refers to an aromatic mono- or bicyclic group containing from 5 or 6 to 14 carbon atoms, preferably 5 or 6 to 12 carbon atoms, of which one to five is replaced with a heteroatom selected from N, S and O, that may optionally be reduced to a non-aromatic heterocycle and may optionally be substituted with one or more, identical or different substituents. Examples of heteroaryl groups include pyrrolyl, dihydropyrrolyl, pyrrolidinyl, oxopyrrolidinyl, indolyl, isoindolyl, indolizinyl, imidazolyl, pyrazolyl, benzimidazolyl, imidazo(1,2-a)pyridinyl, indazolyl, purinyl, pyrrolo(2,3-c)pyridinyl, pyrrolo(3,2-c)pyridinyl, pyrrolo(2,3-b)pyridinyl, pyrazolo(1,5-a)pyridinyl, 1,2,3-triazolyl, 1,2,4-triazolyl, tetrazolyl, oxazolyl, 1,2 oxazolyl, isoxazolyl, 1,3,4-oxadiazolyl, 1,2,5-oxadiazolyl, 1,2,4-oxadiazolyl, 1,2,3-oxadiazolyl, thiazolyl, isothiazolyl, 1,3,4-thiadiazolyl, 1,2,5-thiadiazolyl, 1,2,4-thiadiazolyl, 1,2,3-thiadiazolyl, furanyl, dihydrofuranyl, tetrahydrofuranyl, benzofuranyl, isobenzofuranyl, thiophenyl, dihydrothiophenyl, tetrahydrothiophenyl, benzothiophenyl, benzoisothiophenyl, pyridyl, piperidinyl, quinolinyl, isoquinolinyl, tetrahydroisoqinolinyl, quinolizinyl, pyrazinyl, pyridazinyl, pyrimidinyl, pyranyl, tetrahydropyranyl, 1,2,3-triazinyl, 1,2,4-triazinyl, 1,3,5-triazinyl, chromenyl, morpholinyl, diazepinyl, benzodiazepinyl, and the like.

By the term “heterocycloalkyl” are meant groups which are derived from cycloalkyl as hereinbefore defined if in the hydrocarbon rings one or more of the groups $—CH_2—$ are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone $—SO_2—$; nitrogen→N-oxide). It is immediately apparent from the indirect definition/derivation from cycloalkyl that heterocycloalkyl is made up of the subgroups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

The term “heterocyclic group” as used herein refers to a heterocycloalkyl group which optionally may be fused to an aromatic aryl or heteroaryl group.

Typical examples of individual sub-groups are listed below: Monocyclic heterorings (saturated and unsaturated): oxolane, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, oxane, tetrahydrothiopyranyl, 1,4-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, etc; Bicyclic heterorings (saturated and unsaturated): 8-azabicyclo[3.2.1]octyl, 8-azabicyclo[5.1.0]octyl, 2-oxa-5-azabicyclo[2.2.1]heptyl, 8-oxa-3-aza-bicyclo [3.2.1]octyl, 3,8-diaza-bicyclo[3.2.1]octyl, 2,5-diaza-bicyclo-[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, hexahydro-furo[3,2-b]furyl, etc; Spiro-heterorings (saturated and unsaturated): 1,4-dioxa-spiro[4.5] decyl; 1-oxa-3,8-diaza-spiro[4.5]decyl; 2-oxaspiro[3.3] heptyl, 5-azaspiro[2.4]heptyl, 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl, etc.

By the term "suitable substituent" is meant a substituent that on the one hand is fitting on account of its valency and on the other hand leads to a system with chemical stability.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Any formula or structure given herein, including compounds of a defined formula, is also intended to represent unlabeled forms as well as isotopically-labeled forms of the compounds. Isotopically-labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125J.

The term "pharmaceutically acceptable" also referred to as "pharmacologically acceptable" means compatible with the treatment of animals, in particular, humans. The term pharmacologically acceptable salt includes both pharmacologically acceptable acid addition salts and pharmacologically acceptable basic addition salts.

The term "pharmacologically acceptable acid addition salt" as used herein means any non-toxic organic or inorganic salt of any base compound of the disclosure, or any of its intermediates. Basic compounds of the disclosure that may form an acid addition salt include, for example, compounds that contain a basic nitrogen atom. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono-, di- or the triacid salts can be formed, and such salts may exist in either a hydrated, solvated or substantially anhydrous form. In general, the acid addition salts of the compounds of the disclosure are more soluble in water and various hydrophilic organic solvents, and generally demonstrate higher melting points in comparison to their free base forms. The selection of the appropriate salt will be known to one skilled in the art. Other non-pharmacologically acceptable acid addition salts, e.g. oxalates, may be used, for example, in the isolation of the compounds of the disclosure, for laboratory use, or for subsequent conversion to a pharmacologically acceptable acid addition salt.

The term "pharmacologically acceptable basic salt" as used herein means any non-toxic organic or inorganic basic addition salt of any acid compound of the invention, or any of its intermediates, which are suitable for or compatible with the treatment of animals, in particular humans. Acidic compounds of the invention that may form a basic addition salt include, for example compounds that contain carboxylic acid, sulfonic acid, sulfinic acid, sulfonamide, N-unsubstituted tetrazole, phosphoric acid ester, or sulfuric acid ester. Illustrative inorganic bases which form suitable salts include lithium, sodium, potassium, calcium, magnesium, or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmacologically acceptable basic addition salts, may be used, for example, in the isolation of the compounds of the invention, for laboratory use, or for subsequent conversion to a pharmacologically acceptable basic addition salt. The formation of a desired compound salt is achieved using standard techniques. For example, the neutral compound is treated with a base in a suitable solvent and the formed salt is isolated by filtration, extraction or any other suitable method.

The term "therapeutically effective amount", "effective amount" or "sufficient amount" of a compound of the present invention is a quantity sufficient to, when administered to the subject, including a mammal, for example a human, effect beneficial or desired results, including clinical results, and, as such, an effective amount or synonym thereof depends upon the context in which it is being applied.

Such an effective dose specifically refers to that amount of the compound sufficient to result in healing, prevention or amelioration of conditions related to disorders described herein. The effective dose will vary depending on the health and physical condition of the individual to be treated, the taxonomic group of the individual to be treated, the formulation of the composition, the assessment of the medical situations and other relevant factors.

According to a specific aspect, the pharmaceutical composition described herein contains an effective amount of the compound (or its pharmaceutically acceptable salt) as defined herein. The preparation described herein may be provided for single or multiple dosage use, specifically wherein the compound (or its pharmaceutically acceptable salt) is administered at a dose which can be from about 0.01 mg to about 5.0 g, preferably from about 0.05 mg to 2 g, more preferably from about 0.5 mg to 1 g, even more preferably from about 1 mg to 500 mg. According to a specific aspect, the compound (or its pharmaceutically acceptable salt) can be administered to a patient in an amount of about 0.01 mg to about 5 g, preferably of about 0.05 mg to 2 g, more preferably from about 0.5 mg to 1 g, even more preferably from about 1 mg to about 500 mg per kg body weight.

The term "single-dose" as used herein is understood in the following way. A single-dose or amount for single-use is the amount intended for administration that is meant for use in a single subject, such as a patient, either human or animal for a single case/procedure/administration. Packages comprising the single-dose are typically labelled as such by the manufacturer. The single-dose amount is specifically understood as a daily dose for an individual, like a child or adult, to provide an effective amount.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal or intranasal injections. Administration of the compound the compound (or its pharmaceutically acceptable salt) or the pharmaceutical composition described herein can be carried out in a variety of conventional ways, such as oral ingestion, inhalation, topical application or cutaneous, subcutaneous, intraperitoneal, parenteral or intravenous injection. Intravenous and peroral administration to the patient is preferred.

Preferred embodiments refer to an effective amount in the range of 0.01 mg to 5.0 g/kg body weight, preferably, wherein administration is done intravenously or orally.

The pharmaceutical composition described herein preferably contains one or more pharmaceutically acceptable auxiliaries and is in a pharmaceutical form which allows the active pharmaceutical compound to be administered with high bioavailability. Suitable auxiliaries may be, for example, based on cyclodextrins. Suitable formulations might for example incorporate synthetic polymeric nanoparticles formed of a polymer selected from the group consisting of acrylates, methacrylates, cyanoacrylates, acrylamides, polylactates, polyglycolates, polyanhydrates, polyorthoesters, gelatin, albumin, polystyrenes, polyvinyls, polyacrolein, polyglutaraldehyde and derivatives, copolymers and mixtures thereof.

The Examples which follow are set forth to aid in the understanding of the invention but are not intended to, and should not be construed to limit the scope of the invention in any way. The Examples do not include detailed descriptions of conventional methods. Such methods are well known to those of ordinary skill in the art.

EXAMPLES

Example 1. SCA-744 Induces Global Changes in Gene Expression of Human Cells, Especially Those Involved in the Inflammatory and Anti-Oxidative Responses, as Well as in Lipid Metabolism To determine the cellular response to SCA-744 (Cat. No. 55523-250 MG Sigma-Aldrich), the global changes in gene expression upon treatment of human in vitro cultured cells, SH-SY5Y (neuroblastoma cell line: SH-SY5Y-ATCC-CRL-2266) were analysed by RNAseq analysis. SH-SY5Y were cells differentiated with retinoic acid and Phorbol-12-Myristate-13-Acetate (Presgraves et al. Experimental Neurology 2004, 190(1), pp. 157-170). Cell cultures were treated for 24 hours with 500 μM of SCA-744 or vehicle (DPBS). Total RNA was isolated to prepare libraries using the Lexogen SENSE mRNA kit and sequenced using a HiSeq2500 (Illumina) running in 50 bp single-read modes using sequencing chemistry v4. Differentially expressed genes (DEGs) were identified by applying the statistical tests of DESeq (Anders & Huber, Genome biology 2010, 11(10), p. R106), and edgeR (Robinson et al. Bioinformatics 2009, 26(1), pp. 139-140.) packages. The comparison was made with *Homo sapiens* identifiers.

Notably, several genes involved in inflammation, anti-oxidative, anti-ageing response and lipid metabolism were differentially regulated in the SCA-744 (Table 1, Table 2, FIG. 10).

In further extended analyses of SCA-744 induced gene expression changes, gene sets were imported in Cytoscape and then used for gene ontology, disease areas and pathway analysis with ClueGO plug-in (Bindea et al. Bioinformatics 2009, 25(8), pp. 1091-1093). In addition, a novel computational approach for pathway comparisons was applied to compare the experimentally determined profile of SCA-744 with those reported for the anti-inflammatory compounds, cortisol (hydrocortisone, Sigma-Aldrich, Inc., St. Louis, MO, USA). This approach exploits protein primary structure information and small molecule cheminformatics to identify likely protein targets for drugs and reveals (hidden) drug-drug similarities.

Figure 1:
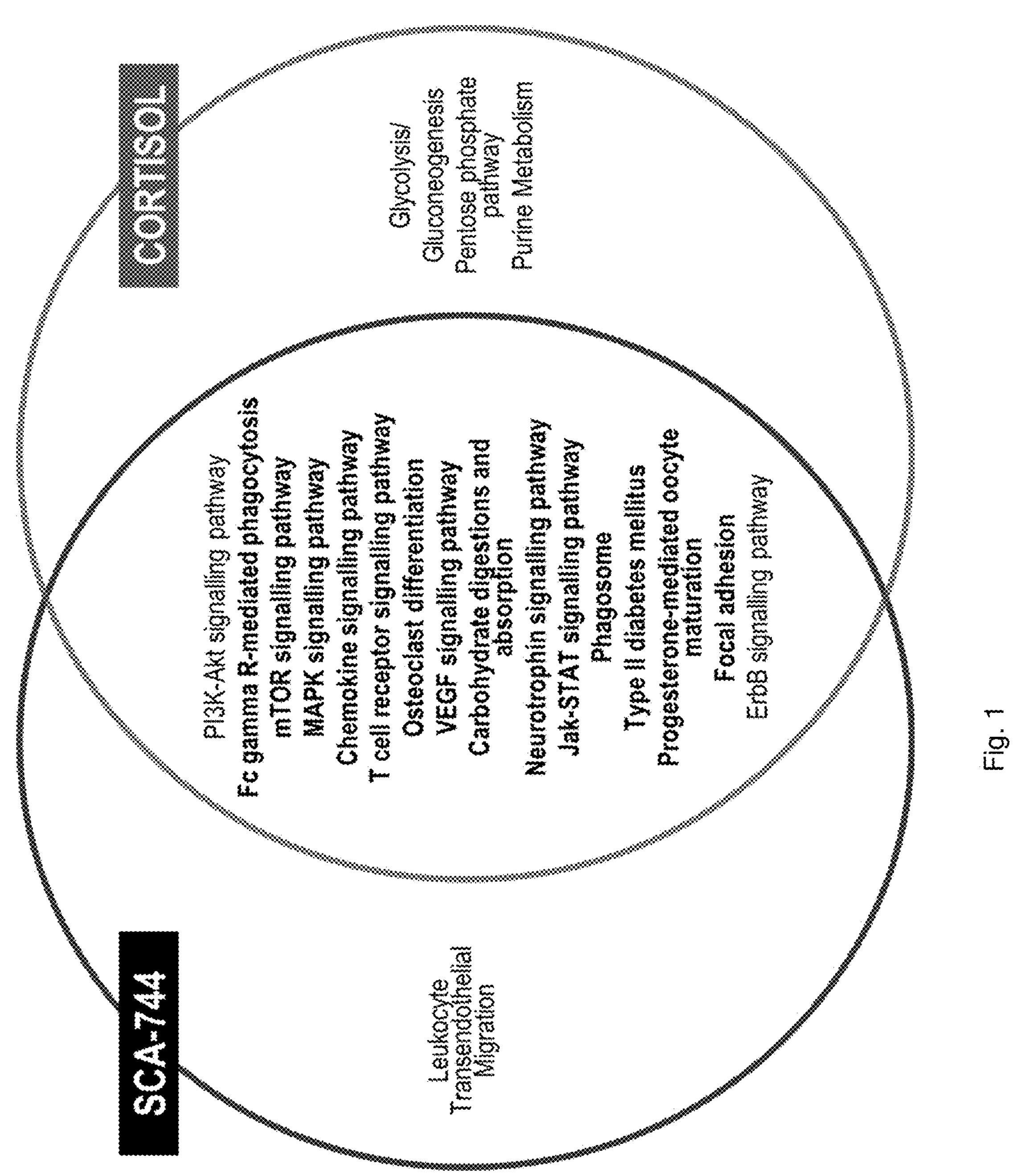
FIG. 1 shows a comparison of cellular pathways modulated by Cortisol and SCA-744 determined based on reported (cortisol) or experimentally verified (SCA-744) gene expression changes. bold: identified experimentally by RNA-Seq analysis.

When the pathways predicted to be affected by SCA-744 (most of them also identified experimentally by the RNASeq analysis) were compared to those reported to be modulated by cortisol (Wan et al. Scientific Reports 2016, pp. 1-14.), a significant overlap was depicted (FIG. 1). However, several metabolic pathways affected by cortisol and involved in its side effects are not modulated by SCA-744, for example, the sugar metabolism and neurotransmitter deactivation pathways.

No other prior art anti-inflammatory drugs have been described with this profile. Based on these findings, SCA-744 and the compounds described herein have the potential of a novel anti-inflammatory compound.

Example 2. SCA-744 Reduces the Production of Pro-Inflammatory Cytokines In Vitro and In Vivo Based on the mRNA expression analysis, the SCA-744 down regulates key genes involved in pro-inflammatory response (Table 1, FIG. 10). To verify these data, a well-characterized and widely used in vitro model of pro-inflammatory signalling, the LPS-stimulated THP-1 human monocytic cell line was employed (Bosshart & Heinzelmann, Annals of Translational Medicine 2016, 4(21), pp. 438-438). Cells were treated with 100 nM of Phorbol 12-myristate 13-acetate (PMA) for 48 h to induce mature macrophage-like state. Cells were then stimulated with 100 ng/ml of Lipopolysaccharides (LPS) in the absence and presence of 500 μM of SCA-744. After 6 hours, supernatants of treated and untreated cells were collected and the levels of three major pro-inflammatory cytokines TNF-α, IL-6 and IL-1ß were determined using the Human Inflammatory panel of LEGENDPLEX Multi-Analyte Flow assay. In the culture supernatant of SCA-744-treated THP-1 cells, significantly decreased pro-inflammatory cytokine levels were measured compared to those of the untreated cells (FIG. 2).

These data—resulting from direct cytokine measurement (at the level of protein expression)—confirm that cells respond to SCA-744 by reduced inflammatory signalling as it was predicted by the changes in gene expression at the mRNA level (RNASeq) detected in a different human cell type (neuroblastoma). Therefore, it can be concluded that the anti-inflammatory effect of SCA-744 is general, and not restricted to immune cells.

Figure 3:
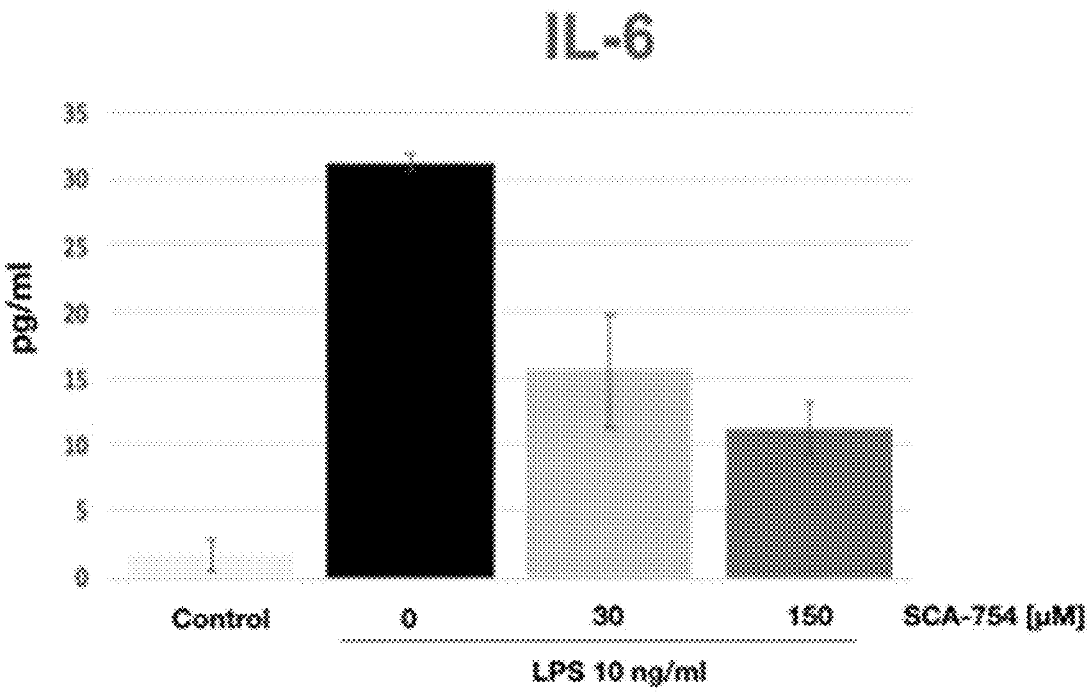
FIG. 3 shows effect of LPS stimulation of THP-1 macrophages on IL-1ß, TNF-α, IL-6 and IL-10 production. Dose-dependent inhibition of LPS-induced TNF-α, IL-ß and IL-6 by SCA-754. Following cells were treated with [10 ng/ml] LPS in the absence and presence 30 and 150 μM of SCA-754. Cytokine levels were determined by LEGENDplex™ Human Inflammation Panel assay from BioLegend. The bar heights represent the concentration means compared to LPS alone of 3 independent experiments carried out in triplicates.

In a second set of experiments, the anti-inflammatory effect of SCA-744 was tested in vivo, in an animal model of ageing. It is well established that the ageing process is associated with low-grade inflammation. Mice older than 18 months show many characteristics of aged humans and are considered as a relevant model of human ageing. The concentrations of over 20 cytokines and chemokines were determined in lung lysates of young and aged animals and found that most of them were present in significantly higher levels in aged animals, compared to their young counterparts (Janesch et al. Cytokine 2018, 111, pp. 389-397). After treatment of aged mice (5 mice/group) with SCA-744 for 2 weeks (at 2 or 3 days intervals at 30 mg/kg dose, i.p.), lungs of the mice were harvested and lysates were prepared. Cytokine levels were determined by LEGENDplex™ Mouse Inflammation Panel assay from BioLegend. Significantly decreased amounts of the pro-inflammatory cytokines IL-6 and TNF-α, as well as the inflammation marker lipocalin (LCN2) were detected (FIG. 3). Importantly, the anti-inflammatory cytokine IL-10 was not affected by SCA-744.

Based on these data, SCA-744 down-regulates the cellular pro-inflammatory cytokine signalling and exerts an anti-inflammatory effect.

Example 3. SCA-744 Induces Anti-Oxidative Cellular Responses in Cultured Human Cells The mRNA expression analysis (RNASeq) indicated the significant up-regulation of three major anti-oxidative genes involved in different oxidative stress response pathways: 1., CHAC1 (Glutathione-specific γ-glutamylcyclotransferase 1), implicated in oxidative stress and apoptosis, 2., NQO1 (NAD(P)H dehydrogenase [quinone] 1), involved in detoxification pathways and 3., SLC7A11 (Cysteine/Glutamate transporter; xCT, CCBR1), producing reduced form of extracellular CySS (result of cysteine oxidation), independent of the Glutathione (GSH) system.

To verify experimentally the anti-oxidative effect of SCA-744, the induction of one of these three genes, NQO1, a major anti-oxidative enzyme was investigated. HeLa (human cervical epithelial cells, ATCC CCL-2) were treated with SCA-744 (50, 100 and 500 μM) for 48 hours and harvested to prepare cell lysate for immunoblot analysis using anti-human NQO1 antibody (A-5: sc-271116, Santa Cruz Biotechnologies). The signal intensity obtained with SCA-744 treated cells confirmed a very significant up-regulation of NQO1 in a SCA-744 concentration dependent manner (FIG. 4). In fact, no NQO1 was detected in control cells under the applied experimental conditions, while a prominent signal was induced even at 50 μM, the lowest concentration of SCA-744 tested, that increased by increasing SCA-744 concentrations (approximately 3.5 fold higher signal at 500 μM). The validity of the experiment was confirmed by a loading control (a protein not expected to be altered by SCA-744; GAPDH).

It is widely accepted that the electron transport chain (ETC) of mitochondria generates the majority (80-90%) of cellular reactive oxygen species (ROS) Jarrett, S. G. et al. Progress in Retinal and Eye Research 2008, 27(6), pp. 596-607. Increasing evidence indicates that mitochondrial dysfunction mediated oxidative stress plays a major role in several disease pathologies. Therefore, physiological activation of anti-oxidant enzymes that respond to increased oxidative stress is thought to be cytoprotective.

Figure 5:
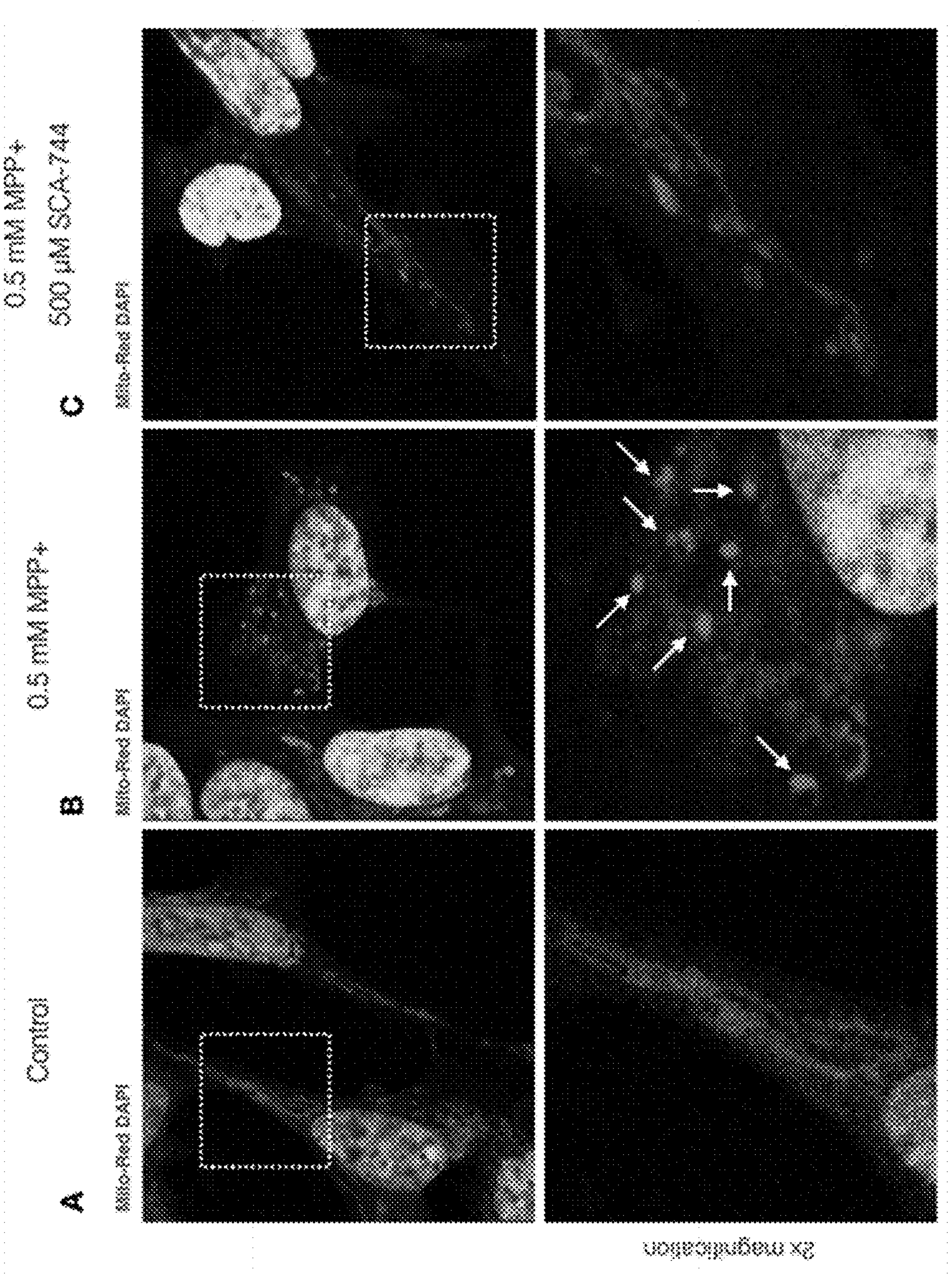
FIG. 5 shows that SCA-744 protects against cell death and restores mitochondria integrity from MPP+ induced damage. Arrows shows dysfunctional mitochondria in the lower middle square panel magnification.

To test whether SCA-744 would be able to rescue cells from oxidative damage induced by mitochondrial dysfunction, SH-SY5Y neuroblastoma cells were treated with 1-methyl-4-phenylpyridinium (MPP+) (0.5 mM, 48 hours) to induce mitochondria fragmentation. MPP+ exhibits its toxicity mainly by promoting the formation of radical reactive free oxygen species in the mitochondria of neuronal cells that leads to further, generalized cellular damage (Przedborski et al. Journal of bioenergetics and biomembranes 2004, 36(4), pp. 375-379). To visualize mitochondria, cells were incubated with MitoTracker Red CMXRos, a mildly thiol-reactive chloromethyl moiety for mitochondria labelling (MitoTracker Red CMXRos #9082 Cell Signaling), fixed and mounted. Mitochondrial morphology was imaged with a laser scanning confocal microscope LSM710 Zeiss. In the presence of SCA-744 (500 μM), cells maintained the integrity of mitochondria suggesting that the formation of ROS were greatly diminished or prevented (FIG. 5).

Based on these data from two independent in vitro experimental model, SCA-744 increases the anti-oxidative capacity of cells, and act as anti-oxidant.

Example 4. SCA-744 Modulates Lipid Metabolism

As illustrated in the Table 1 (FIG. 10), the SCA-744 affects the expression of several genes involved in lipid metabolism, such as the Low-density Lipoprotein Receptor, a major determinant of cholesterol levels in plasma. LDLR. Interestingly, the expression of several of these genes are reported to be regulated by the Wnt and Hedgehog signalling pathways (Bandari et al. Current Protein and Peptide Science 2015, 16(1), pp. 66-76; Ali et al. Arthritis & Rheumatology 2015, 68(1), pp. 127-137.). To assess directly the effect of SCA-744 on the level of LDL-R expression, HeLa cells were treated with SCA-744 at 50 or 500 μM concentrations for 24 or 48 hours. Cells were harvested, cell lysate prepared and then analysed by immunoblotting using an anti-human LDL-R antibody (C7: sc-18823, Santa Cruz Biotechnologies).

Figure 6:
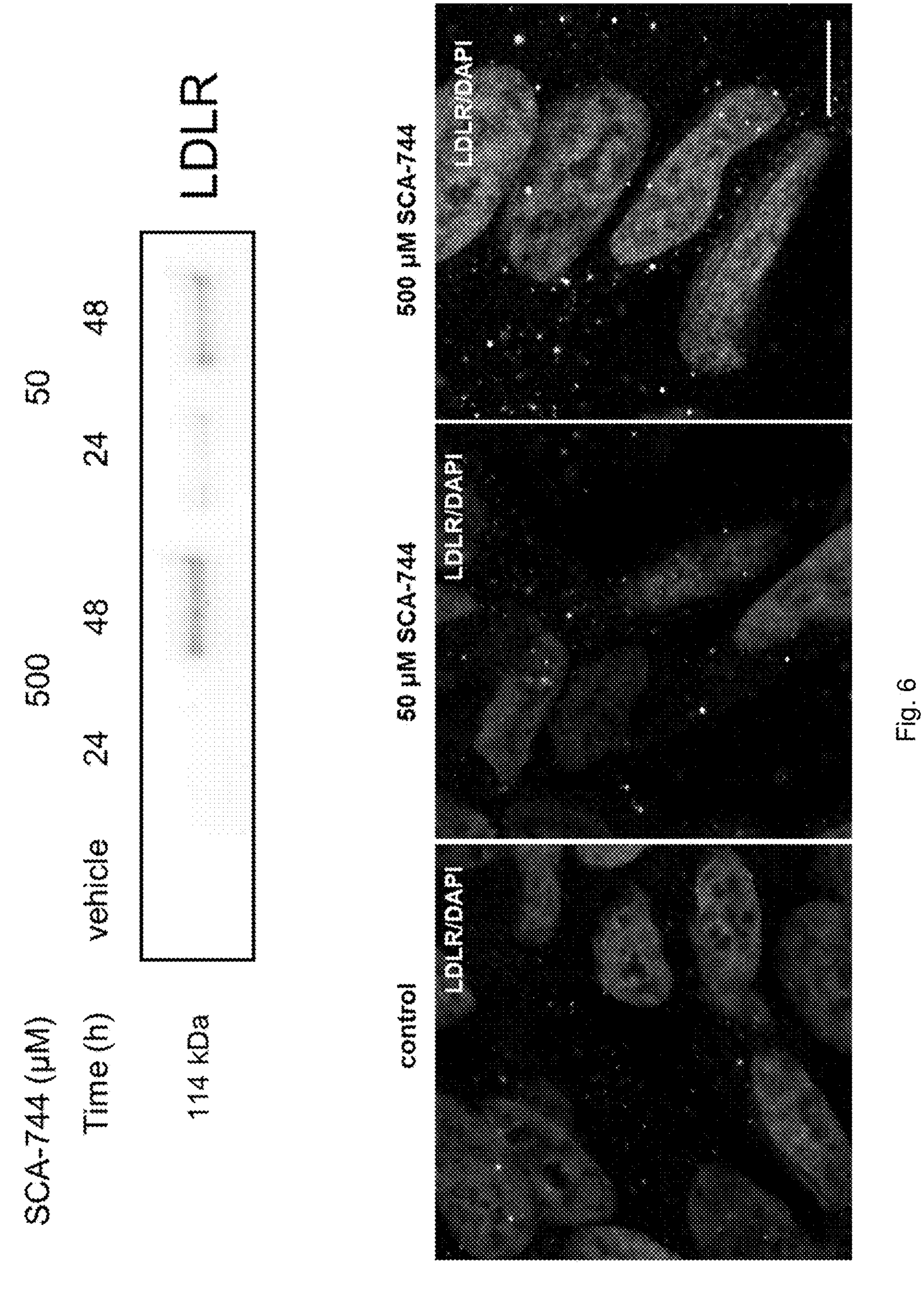
FIG. 6 shows that SCA-744 induces the expression of LDLR in HeLa cells by immunoblotting (A) and immunofluorescent microscopy (B).

In control cells (no treatment), no LDL-R signal was observed, while at both concentrations of SCA-744, the LDL-R was detected in the cell lysates with a tendency for higher levels at the higher SCA-744 concentration and longer exposure (48 vs. 24 hours) (FIG. 6A).

In another set of experiments, HeLa cells were treated the same way (50 and 500 μM of SCA-744 for 48 hours). Cells were fixed with 4% paraformaldehyde solution for 10 min at RT and permeabilized with 0.1% Triton X-100 for 15 min at RT and analysed by immunofluorescence microscopy using the same anti-human LDLR antibody employed for the immunoblotting. This detection method was more sensitive, and indicated the presence of LDL-R even in control cells. Based on semi-quantitative analysis (comparing the number of fluorescent dots in several different fields), SCA-744 significantly increased the level of LDL-R in a concentration dependent manner (FIG. 6B).

These data confirmed the RNASeq-based increased gene expression of LDL-R at the protein level. Based on these, it can be concluded that cells exposed to SCA-744 respond with increased production of the LDL-R. LDL-R is intimately connected to lipid metabolism, and several other genes involved in cholesterol synthesis were differentially expressed in the presence of SCA-744 at the mRNA level (Table 1, FIG. 10).

Example 5. SCA-744 Binds to Heparan-Sulfate Binding Protein, Osteopontin and Antagonizes with HS Based on the chemical similarity of SCA-744 to heparan sulfate (HS)—both being negatively charged sulfated carbohydrates (depicted in FIG. 8)—and the modulatory effect of SCA-744 on lipid metabolism genes regulated by the Hedgehog signalling or involved in pro-inflammatory signalling (Table 1, FIG. 10, Example 2 and 4) both involving heparan sulfate-binding proteins (Xu & Esko, Annual Review of Biochemistry 2014, 83(1), pp. 129-157), the hypothesis was put forward that SCA-744 exerts its pleiotropic effects on cellular metabolism by HS-mimicry.

Figure 7:
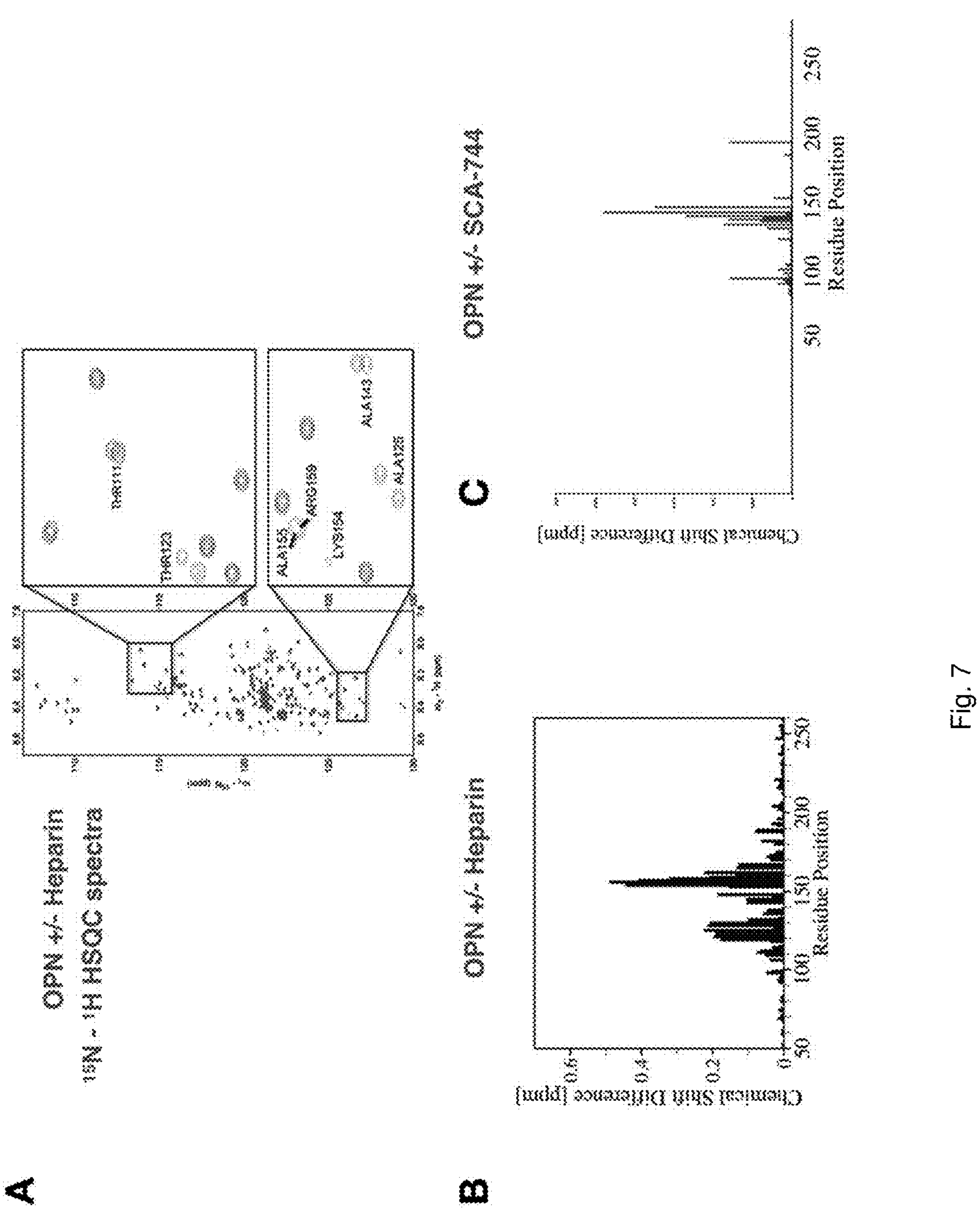
FIG. 7 shows that SCA-744 binds to a heparan sulfate binding protein, osteopontin (A) involving similar protein regions that interact with heparin (B, C).

In order to verify the predicted heparan sulfate mimicking activity of SCA-744, its physical interaction was probed with a prototypical HS-binding protein Osteopontin (OPN), a component of the extracellular matrix (ECM). To this end, NMR spectroscopy was used to directly probe the interaction and map the location of the interaction site along the protein backbone. The experimental strategy was as follows: First, $^{15}$N-labelled OPN was prepared following well-established molecular biology technology techniques. Individual residue positions are directly monitored via the so-called $^{15}$N-$^{1}$H Heteronuclear Single-Quantum Coherence (HSQC) spectroscopy, where individual cross peaks in the two-dimensional (2D) frequency spectrum corresponds to individual residue positions (amino acids) of the protein. Ligand binding changes the chemical environment of residues located in the binding site and leads to a change in the HSQC spectrum. Since the signal assignment is available, the residue positions which are affected by ligand binding can easily be identified by comparing HSQC spectra of the apo (ligand-free) and ligand-bound state of the protein (FIG. 7A). Inspection of the ligand-free and ligand-bound HSQC spectra provided unambigious proof for SCA-744 binding to OPN. It is very convenient to analyze the chemical shift changes (induced by ligand binding) as a function of residue positions (FIG. 7B,C). Residues that display the largest chemical shift changes are typically part of the binding interface. It can clearly be seen that both HS and SCA-744 display overlapping binding sites (the same residue segments are affected by the binding process). Therefore, it can be concluded that SCA-744 and HS share the same ligand interaction sites and therefore are in competition for binding.

Figure 9:
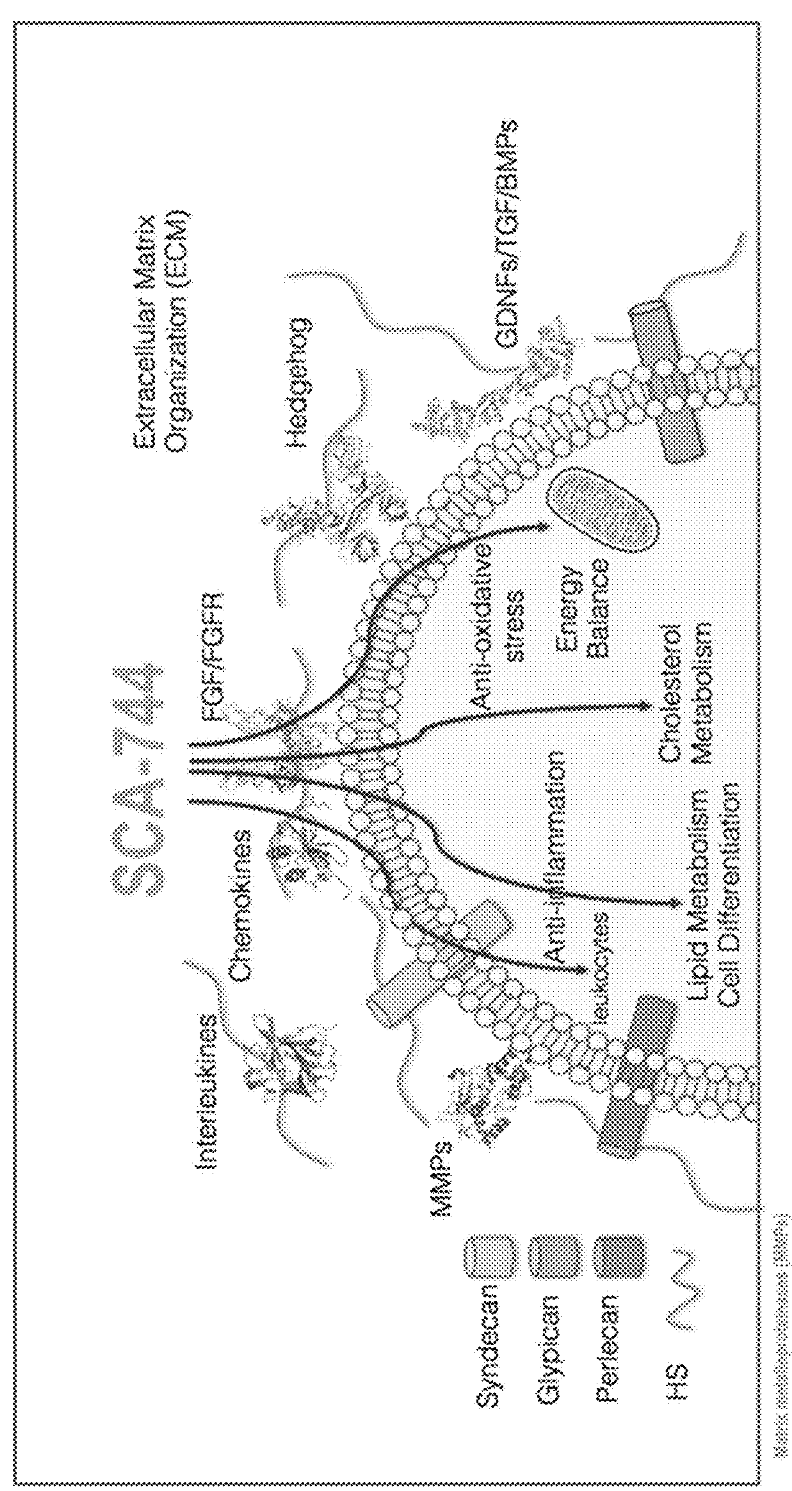
FIG. 9 depicts the mode of action of SCA-744 as a pathway modifier acting from the extracellular space via heparan sulfate interacting molecules.

Based on these data and the pattern of gene expression, SCA-744 was found to mimic heparan sulfate based on chemical similarity and acts as a pathway modifier from the extracellular space via heparan sulfate interacting molecules (FIG. 9). According to this model, SCA-744, targets multiple ECM proteins, e.g. the members of the hedgehog signalling pathway, Fibroblast growth factor (FGF) and fibroblast growth factor extracellular receptor (FGFR) interaction, signalling by cytokines and chemokines, resulting in reduced pro-inflammatory response.

Example 6. Mode of Action and Selection of Compounds Using Standard Assays

SCA-744 Acting as a Heparan Sulfate (HS) Mimic

Antagonism with HS-binding proteins: As described above, SCA-744 interacts with osteopontin, a HS-binding protein, and the HS and SCA-744 binding sites are shared. Competitive antagonism is proven by NMR based measurements. Several other HS-binding proteins involved in cellular signalling are tested (e.g. those involved in hedgehog signalling).

Interference of HS with SCA-744 Mediated Effects:

SCA-744 was shown to significantly reduce cytokine production induced by LPS and induce anti-oxidative enzymes in in vitro assays. Co-incubation with HS is used to test whether HS reduces the effect of SCA-744. HS is a polymer sugar that is commercially available, but the polymer length in different preparations differ greatly. HS-subspecies (short, medium and long) are purified and their effects tested individually. Small molecular weight heparin (another sulphated polymeric carbohydrate), but not high-molecular weight forms was reported to have anti-inflammatory effect. This is also tested in parallel.

Effect on Pro-Inflammatory Signalling

An NF-κB reporter cell line is used to measure the potency and selectivity of SCA-744 to block pro-inflammatory responses (THP1-Lucia™ cells, specifically designed for monitoring the NF-κB signal transduction pathway). The modulation of NF-κB activity by SCA-744 is monitored mechanistically. NF-κB activation relies on two major signaling pathways known as the classical (or canonical) and the alternative NF-κB signaling pathways. To understand the signaling pathways involved in the anti-inflammatory kinase signaling network in response to SCA-744 engagement with cell surface receptors, KINOMEscan assays are performed. This screening platform employs a novel active site-directed competition-binding assay to quantitatively measure interactions between compounds and more than 450 kinases.

Anti-Oxidative Response

SCA-744 showed anti-oxidative properties in cell culture by inducing the expression of several genes involved in removal of reactive oxygen species (ROS). NQO1, one of the major downstream anti-oxidative genes regulated by Nuclear Factor (erythroid-derived 2)-like 2 (NRF2). NRF2 is a ubiquitously expressed and essential leucine zipper transcription factor. It regulates the expression of a variety of genes encoding proteins that play critical roles in cytoprotection, as well as the detoxification and clearance of harmful endogenous and xenobiotic substances upon binding to antioxidant response elements (AREs). Human NRF2 Reporter Cells are a stable cell line that includes the luciferase reporter gene functionally linked to a promoter containing tandem anti-oxidant response elements (AREs). Thus, quantifying changes in luciferase expression in the treated reporter cells provides a sensitive readout measure of the changes in NRF2 activity. Known NRF2 agonist is used as positive control.

Hedgehog Signaling

RNAseq transcriptome drug profiling in cell culture showed the upregulation of genes involved in the Hedgehog (Hh) signaling pathway that is a major pathway to regulate lipid/cholesterol metabolism. To study the effect of SCA-744 on Hh signaling, known Hh agonist and antagonists are used to measure the activity/expression of the major negative regulator INSG1 and the transcriptional regulator SREBF2 and also genes involved in the homeostasis of cholesterol such as hydroxymethyl glutaryl-coenzyme A reductase (HMGCR), 7-Dehydrocholesterol-reductase (DHCR7), low-density lipoprotein receptor (LDLR), and the ATP-binding cassette transporter (ABCA1).

Comparison of SCA-744 and Cortisol Induced Gene Expression

RNAseq transcriptome drug profiling is a suitable tool to study gene regulation upon drug stimuli. Based on the similarities and differences predicted by the above described in silico approach between SCA-744 and cortisol, a cortisol RNAseq drug transcriptome is generated in order to analyze the similarities and differences at a pathway level based on differential gene expression.

Phenotypic profiling of SCA-744 is performed using the BioMap™ DiscoverX (Th1 inflammation-driven macrophage activation, T-cell-dependent activation of B cells involved in chronic inflammation) to monitor changes in pro-inflammatory protein biomarkers in the presence of SCA-744 and compare those with the changes seen with cortisol.

Glucose metabolism: One of the major limitations of anti-inflammatory corticosteroids is their diabetogenic side-effect. The findings described above suggest clear differences between SCA-744 and cortisol at the level of glucose and insulin metabolism at a transcriptional level. These differences are confirmed at higher resolution, i., the phosphorylation of Akt1 and IRS1 is studied in response to insulin and cytokines in the presence of SCA-744, compared to cortisol by Western blotting; and ii., a functional assay is performed to monitor the cellular uptake of glucose using 2-NBDG, a fluorescent glucose analogue designed specifically for sensitive detection in high-throughput assays. Differences of 2-NBDG uptake in response to insulin in the presence of SCA-744 and cortisol are quantified using FACS and high-content microscopy.

Example 7. Testing SCA-744 in Human Disease Related Models

Psoriasis

MatTek Corp. has developed a human skin equivalent (HSE) 3D-tissue model for psoriasis. The model is using fibroblasts from psoriasis patients and a proprietary cytokine mixture to induce psoriasis. This model can be used to assess efficacy of Calixarenes in reducing inflammatory cytokine response at different doses. Potentially the model can be supplemented with immune cells.

While psoriasis is a strictly human disease, the imiquimod (IMQ) induced psoriasis model has been successfully used to test candidates against the disease (Horváth et al.; Scientific Reports 2019, 9, Article number: 3685]). IMQ is an innate TLR7/8 ligand, rapidly inducing inflamed skin lesions in mice resembling plaque type psoriasis and acts through the IL-23/IL-17 cytokine axis (van der Fits et al.; Journal of Immunology 2009, 182, pp. 5836-584). This model can be used to assess efficacy of systemically administered Calixarenes against the clinical signs and histopathological changes induced in the lesion, as well as to monitor changes in skin cytokine response. Lead candidates are tested in systemic and topical administration, at different doses.

Arthritis:

Complete Freund's Adjuvant (CFA) induced chronic arthritis mouse model can be employed to test efficacy of Calixarenes in reducing joint inflammation (Horváth, et al.; Arthritis Research and Therapy, 2016; 18:6.). In this model, arthritis is induced by intraplantar and repeated subcutaneous injection of CFA. Calixarenes can be administered systemically or orally daily. Clinical signs (e.g. ankle oedema), local inflammatory signs (e.g. plasma leakage) can be monitored for 3 weeks, histopathological analysis of the joint and cytokine levels in the joints.

Lead candidate molecules can be further tested in collagen induced rheumatoid arthritis model in rats. Unlike in CFA arthritis, in this model there is a general inflammation of the joints, not restricted to the ankle. Arthritis is induced by two subsequent intradermal injection of bovine collagen. Lead compounds can be administered either systemically or orally in a therapeutic setting (i.e. after the development of arthritis). As a positive control, methotrexate (an immunosuppressant used in the clinic against RA) can be used to compare efficacy. Clinical signs (joint swelling and non-specific clinical signs) and biochemical parameters of inflammation can be assessed in treated and placebo control animals. Additionally, limbs can be preserved for histopathology examination, that are performed only if the other read-outs show no significant difference between treated vs control animals.

Asthma:

It has been shown, that asthma patients have altered basal epithelial cytokine levels compared to healthy individuals (Freishtat et al.; American Journal of Respiratory Cell and Molecular Biology 2011, 44, pp. 863-869). A 3D-epithelial lung tissue model using cells from asthma patients allows testing the efficacy of anti-asthma compounds in restoring normal cytokine levels. Readouts of the test were validated with anti-inflammatory drugs used in the clinic (corticosteroids and steroid-analogs) (Damsker et al.; PLoS One 2013, 8(5):e63871) and can be used as positive controls when testing Calixarenes. Ovalbumin (OVA) induced lung inflammation model in mice can be used to assess efficacy of Calixarenes against asthma (Elekes et al.; European Journal of Pharmacology 2008, 578, pp. 313-322). In this model, after priming the animals with i.p. administered OVA, airway hyperresponsiveness is induced with intranasally administered OVA. Calixarene, prednisone or vehicle can be given systemically to mice one day before and throughout the administration of intranasal OVA. Airway responsiveness is assessed by whole body plethysmograph, and inflammatory changes in the lung will be detected with histopathological examination. Lead candidate selected against asthma can be tested at different administration routes (e.g. orally), regiments (prophylactic, therapeutic) and doses.

Steroid-Like Side-Effect Studies:

Chronic use of corticosteroids is associated with severe side-effects often limiting not only their efficacy, but even their use. Such side effects are acute and chronic increased insulin resistance (ultimately leading to diabetes), decreased bone turnover (leading to bone demineralization and fractions or growth retardation in children), depression and immunosuppression. Immunotoxic and growth-related side effects can be detected if juvenile mice treated with steroids chronically (15-week model). Calixarenes can be tested in this chronic administration model and compare growth related (overall length and tibial length) and immunotoxic (spleen size) side effects to that of dexamethasone.

Heparan Sulfate Mimicking Activity

1. NMR: Measuring physical interaction with an HS-binding protein Osteopontin (OPN) using NMR spectroscopy to directly probe the interaction and map the location of the interaction site in the protein. $^{15}N$-labelled OPN is used, where individual residue positions are directly monitored via the so-called $^{15}N$-$^{1}H$ Heteronuclear Single-Quantum Coherence (HSQC) spectroscopy, where individual cross peaks in the two-dimensional (2D) frequency spectrum corresponds to individual residue positions (amino acids) of the protein. Ligand binding changes the chemical environment of residues located in the binding site and leads to a change in the HSQC spectrum. Comparing the ligand-free and ligand-bound HSQC spectra provide unambigious proof for SCA-744 binding to OPN. Residues that display the largest chemical shift changes are typically part of the binding interface. Overlapping binding sites are indicative for competition for binding.

2. Biacore or biolayer interferometry (BLI)—Example: Osteopontin or other HS-binding proteins are coated on sensor chips (for example using biotin labelled recombinant protein on Streptavidin-coated chips), binding to HS is easily detected, addition of SCA-744 is expected to reduce or eliminate the binding signal.

3. Affinity chromatography—Example: Osteopontin or other HS-binding protein is immobilized on the chromatography matrix (e.g. biotin labelled protein of Streptavidin coated chromatography beads), HS is added, after washing the column, elution of HS by SCA-744 from the column is detected.

Example 8: SCA-744 has a Prominent Anti-Inflammatory Effect in a Murine Model of Acute Lung Inflammation Methods 8-12-week-old, female C57BL/6J mice were used in the experiments in 4 groups (5 to 7 animals/group): 1) PBS-negative control group, 2) LS only, 3) LPS+SCA-744 and 4) LPS+dexamethasone.

Endotoxin (Lipopolysaccharide: LPS)-Induced Acute Lung Inflammation Model

Acute lung inflammation was induced by intratracheal administration of 100 μg LPS (*Escherichia coli* O111:B4; Sigma Aldrich, St. Louis, MO, USA) dissolved in 60 μl sterile phosphate buffered saline (PBS) under ketamine (120 mg/kg ip.; Calypsol, Gedeon Richter Plc., Budapest, Hungary) and xylazine (6 mg/kg ip.; Sedaxylan, Eurovet Animal Health B.V., Bladel, Netherlands) anaesthesia. 24 h after administration, respiratory function parameters were assessed, and lung samples were harvested for histopathological evaluation.

Treatments and Experimental Design

SCA-744 (60 mg/kg) and its vehicle were injected intraperitoneally (i.p.), 24 h, 12 h, 20 min before and 12 h after intratracheal administration of LPS. The long-acting steroid dexamethasone (5 mg/kg; elimination T½:36-54 h) was administered ip. 24 h and 20 min before LPS treatment. Respiratory function measurement was performed 24 h after LPS administration Respiratory Function Measurement Buxco FinePoint Non-invasive Airway Mechanics (NAM) double chamber plethysmography (DSI Harvard Bioscience Inc.) was used to monitor ventilatory and bronchoconstriction parameters in awake, restrained animals without the use of anesthesia. The plethysmograph measures the nasal and thoracic flows independently. After acclimatization of the animals for 2×20 minutes on day −2 (−42 h) and −1 (−18 h), animals were placed in the plethysmography chambers 24 h after LPS administration. After 10 minutes of acclimatization period baseline pulmonary functions were assessed, such as the frequency, tidal volume, minute ventilation, expiratory/inspiratory time, peak expiratory/inspiratory flow, and specific airway resistance, a measure of bronchoconstriction.

Termination, Tissue Harvesting

After respiratory function assessment animals were anaesthetized and their lungs were harvested for histopathological evaluation.

Histopathological Evaluation

Excised lung tissue samples were formalin-fixed (6%) and embedded in paraffin, 5 μm sections cut and stained with haematoxylin-eosin for histological analysis. Assessment of airway inflammation was performed in a blind manner in order to evaluate perivascular/peribronchial edema, neutrophil, macrophage and lymphocyte inflammatory cell infiltration as well as goblet cell metaplasia on a semiquantitative scale ranging from 0 to 3 in 2 fields of vision from three depths of lung tissue from each animal.

Results

Mice treated with LPS had significantly altered respiratory functions, such as increased breath rate (Breaths Per Minute, (f) BPM), increased Functional Residual Capacity (FRC), reduced Expiratory time (Te), increase PEF relative to Te (Rpef), increased the time between nasal and thoracic breathing (add more exact description from Kata). In animals receiving SCA-744, LPS treatment did not induce statistically significant alterations in these parameters compared to those measured in control animals (not treated with LPS) (FIG. 11). Treatment with dexamethasone had some positive effects, but parameters were still significantly altered compared to control animals.

Histological examination of tissues revealed that SCA-744 treatment prevented or greatly reduced the pathological changes in perivascular oedema, and perivascular/peribronchial infiltration by neutrophils and macrophages (FIG. 12). Semiquantitative analysis of stained tissues revealed that SCA-744-treated lung samples were not statistically significantly different from untreated controls in any of the three parameters and the composite pathology score, while LPS+vehicle treated samples were, demonstrating that SCA-744 prevented the inflammation associated alterations (FIG. 13). There was a tendency for reduction in these inflammatory parameters in the dexamethasone treated group, but did not reach statistical significance, except for reducing the granulocyte numbers.

Example 9: The Beneficial Effect of SCA-744 in a Chronic Arthritis Mouse Model

Methods

Complete Freund's Adjuvant (CFA)-Induced Chronic Arthritis Model

The chronic arthritis was induced by intraplantar (i.pl.) injection of 20 μl complete Freund's adjuvant (CFA, heat-killed *Mycobacterium* suspended in paraffin oil, 1 mg/ml; Sigma Aldrich, St. Louis, MO, USA) into the right hind paw and 20 μl subcutaneously (s.c.) into the tail root. An additional s.c. injection (20 μl) was administered on the following day (day 1) into the tail root in order to potentiate the systemic effects mimicking the human condition.

Treatments and Experimental Design

SCA-744 (60 mg/kg), or the reference compound dexamethasone (60 mg/kg), as well as the vehicle of SCA-744 were injected i.p. daily starting on day 0 immediately before CFA administration and throughout the 21-day experimental period.

Measurements of Mechanonociceptive Thresholds of the Hind Paw

The dynamic plantar aesthesiometer (DPA, Ugo Basile 37400, Comerio, Italy) was used for the assessment of the mechanosensitivity of plantar surface of the hind paw. Mice were placed into plexiglass boxes with wire grid floor, then after acclimation the plantar surface was touched with a straight metal filament lifting with increasing upward force (maximum force of 10 g reached within 4 s) until the animal withdrew his paw. Mechanical hypersensitivity is represented as a percentage decrease of the initial (before CFA administration) withdrawal thresholds.

Measurements of Paw Volume

The paw volume was determined by plethysmometry (Ugo Basile Plethysmometer 7140, Comerio, Italy) and expressed in cubic centimeter (cm3), then edema is presented as percentage increase of initial values.

In Vivo Bioluminescence Imaging of Neutrophil Myeloperoxidase Activity

Neutrophil myeloperoxidase (MPO)-derived reactive oxygen species (ROS) production and the enzyme activity were assessed with luminol-derived bioluminescence. Luminol (5-amino-2,3-dihydro-1,4-phthalazine-dione) sodium salt (150 mg/kg, Gold Biotechnology, Olivette, MO, USA) dissolved in sterile phosphate buffered saline (PBS, 30 mg/mL) is injected i.p. into anesthetized mice. They were anesthetized using ketamine (120 mg/kg ip.; Calypsol, Gedeon Richter Plc., Budapest, Hungary) and xylazine (6 mg/kg ip.; Sedaxylan, Eurovet Animal Health B.V., Bladel, Netherlands). Bioluminescence imaging was performed 10 minutes post-injection using the IVIS Lumina III (PerkinElmer, Waltham, USA; 120s acquisition, Binning=8, F/Stop=1). Identical Region of Interests (ROIs) are applied around the ankles and luminescence was expressed as total radiance (total photon flux/s).

Histology

The excised tibiotarsal joints are fixed in 4% buffer formaldehye, decalcified and paraffin-embedded, sliced into sections (5 μm) and stained with hematoxylin and esosin. Arthritic changes are scored by a blinded observer using a scale of 0 to 3 according to 1) mononuclear cells infiltration into areolar tissue, 2) synovial hyperplasia, 3) cartilage destruction, 4) bone erosion.

Results

The effects of the CFA-induced inflammation in the paw region can be detected in the ankle joint and reveals as bone erosion, cartilage destruction, synovial hyperplasia and mononuclear cell infiltration (FIG. 14A). In the early stage of joint inflammation process, synovial hyperplasia is a significant finding. The synovial hyperplasia score, increased by CFA-injection, was significantly lower in mice concomitantly treated with SCA-744 and this effect was comparable to those observed upon dexamethasone treatment (FIG. 14B).

These data suggest that SCA-744 had beneficial effects leading to the prevention of the synovial tissue pathology similarly to dexamethasone, a commonly used medication in arthritis treatment.

Example 10. Route of Synthesis of Exemplary Compounds

The chemical synthesis of the calixarenes is be based on a 3+1 fragment condensation strategy and follow well-established chemical synthetic procedures (Gutsche, CD Calixarenes Revisited in "Monographs in Supramolecular Chemistry", Stoddard, F J, Ed., Royal Society of Chemistry (pg-38-47). The fragment containing three ring systems carry-OH and t-butyl substituents, linked via methylene ($—CH_2—$) linkers. The terminal (flanking) aromatic rings contain a reactive group that is used for the coupling reaction to the single fragment. The single fragment comprises the various substituted or un-substituted aryl (also heteroaryl) systems described in the generic formula, as well as two reactive functional groups for the coupling to the 3-ring fragment. For example, $—CH_2—Br$ has been described as an efficient functional group for the coupling reaction ($TiCl_4$, dioxane, 80-120 hrs reflux) to give calix[4]arenes in 25-30% yields (Gutsche, CD Calixarenes Revisited in "Monographs in Supramolecular Chemistry", Stoddard, FJ, Ed., Royal Society of Chemistry (pg-38-47).

Synthesis of Calixarene Compounds (FIG. 15)

2,6-Bis(hydroxymethyl)-4-tert-butylphenol 2[1]

An aqueous NaOH solution (2.7 g in 27 mL $H_2O$) was added to 4-tert-butylphenol 1 (10 g). After addition of an aqueous formaldehyde solution (33%; 10 mL), the mixture was stirred under argon atmosphere for 3 days at 40° C. The sodium salt precipitated after addition of brine (100 mL), was filtered off and washed with brine (30 mL). This solid was then redissolved in 35 mL of water and the resulting solution acidified to pH=1 using diluted HCl (1M). The mixture was then extracted with $CH_2Cl_2$ (3×30 mL) and the combined organic phases were subsequently washed with water (50 mL) and dried over $MgSO_4$. Evaporation of the solvents gave an oily residue, which was purified via silica gel column chromatography using a mixture of heptane and ethyl acetate (4:3) as an eluent. The product containing fractions were identified on TLC under the UV-lamp. The product fractions were combined and the solvents evaporated to give 3.4 g of compound 2 as a white solid. $^1H$-NMR (400 MHz; $CDCl_3$): 7.89 (s, 1H); 7.08 (s, 2H); 4.80 (d, 4.6 Hz, 4H); 2.54 (bs, 2H); 1.28 (s, 9H); $^{13}C$-NMR (150 MHz); $CDCl_3$): 152.37; 142.65; 125.45; 124.87; 63.96; 34.03; 31.48.

2,6-Bis(2-hydroxy-5-tert-butylbenzyl)-4-tert-butylphenol 3[2]

A mixture of 4-tert-butylphenol 1 (2.8 g) and 2,6-bis(hydroxymethyl)-4-tert-butylphenol 2 (0.5 g) were stirred in dry toluene (10 mL) in presence of p-toluenesulfonic acid monohydrate (12 mg) overnight at 140° C. oil bath temperature. The reaction mixture was brought to room temperature and toluene was removed under reduced pressure. The residual oil was redissolved in a small amount of acetone and heptane was added until the solution became turbid. The product precipitated while storing this mixture in the fridge. Compound 3 was isolated by filtration, washed with heptane and dried in vacuo to yield 415 mg, $^1H$-NMR (400 MHz; $CDCl_3$): 8.82 (s, 1H); 7.90 (s, 2H); 7.29 (d, 2.4 Hz, 2H); 7.19 (s, 2H); 7.07 (dd, 8.4 Hz, 2.4 Hz, 2H); 6.74 (d, 8.4 Hz, 2H); 3.91 (s, 4H); 1.29 (s, 9H); 1.26 (s, 18H).

2,6-Bis(bromomethyl)-4-methylphenol 5[3]

Paraformaldehyde (1.69 g) was dissolved in HBr/acetic acid (33%, 15 mL). This mixture was cooled in an ice-bath, before cresol 4 (2.7 g) was added drop-wise using a dropping funnel. Stirring was continued at 0° C. for another hour and then 1.5 h at room temperature. The mixture was poured into an ice/water mixture and extracted with $CH_2Cl_2$ (3×30 mL). The combined organic phases where washed with water (2×20 mL) and dried over $MgSO_4$. Evaporation of the solvents under reduced pressure gave an oily residue, which was again dissolved in a small amount of $CH_2Cl_2$. Precipitation of the product was induced by adding heptane and completed by storing the mixture at 4° C. The solid product was filtered off and dried in vacuo to yield 1.11 g of compound 5. $^1H$-NMR (400 MHz; $CDCl_3$): 7.08 (s, 2H); 5.41 (s, 1H); 4.54 (s, 4H); 2.26 (s, 3H).

Cyclo-(2-hydroxy-5-methyl-1,3-phenylene)methylene-tris[(2-hydroxy-5-tert-butyl-1,3-phenylene)methylene] 6[3]

2,6-Bis(bromomethyl)-4-methylphenol 5 (1.5 g) and 2,6-bis(2-hydroxy-5-tert-butylbenzyl)-4-tert-butyl-phenol 3 (2.37 g) were dissolved in acetic acid (300 mL) and slowly added to acetic acid (300 mL) using a dropping funnel at a temperature of 118° C. within 6 h. The mixture was stirred at the same temperature for another 48 h, before the solvents were removed at reduced pressure. The residue was purified using two consecutive silica gel chromatography columns (eluent: heptane/ethyl acetate (4:6) and heptane/toluene (3:1). The product-containing fractions were identified using $KMnO_4$ staining and evaporated in vacuo to yield 400 mg product 6. $^1H$-NMR (400 MHz; $CDCl_3$): 10.26 (s, 2H); 7.02-7.08 (m, 4H); 7.02 (s, 2H), 6.84 (s, 2H); 4.23 (bs, 4H); 3.47 (bs, 4H); 2.13 (s, 3H); 1.23 (s, 18H); 1.19 (s, 9H). MS (neg. mode): m/z=605.33 ($[M-H]^-$); calc. 605.36.

Cyclo-(2-hydroxy-5-methyl-1,3-phenylene)methylene-tris[(phenylene)methylene] 7

A mixture of compound 6 (248 mg), phenol (220 mg) and $AlCl_3$ (400 mg) was dissolved in dry toluene (6 mL) and stirred at 60° C. for 5 h under argon atmosphere. The reaction was brought to room temperature and after addition of 3% HCl (5 mL) stirring was continued for 30 minutes. The solution was extracted with toluene (3×30 mL) and the combined toluene phases dried over $MgSO_4$. The solvents were evaporated in vacuo and the product precipitated by addition of methanol (2 mL) to the oily residue. The resulting solid was filtered off and recrystallized from a mixture of $CH_2Cl_2$ and methanol. The reaction gave 80 mg of compound 7 as a white solid. $^1H$-NMR (400 MHz; $CDCl_3$): 10.17 (s, 4H); 7.05 (d, 7.6 Hz, 4H); 7.04 (d, 7.5 Hz, 2H); 6.84 (s, 2H); 6.73 (t, 7.5 Hz, 2H); 6.71 (t, 7.5 Hz, 1H); 4.24 (bs, 4H); 3.50 (bs, 4H); 2.13 (s, 3H). MS (neg. mode): m/z=437.1762 ($[M-H]^-$); calc. 437.1758.

Cyclo-(2-hydroxy-5-methyl-1,3-phenylene)methylene-tris[(2-hydroxy-5-sulfonato-1,3-phenylene methylene] 8

Compound 7 (80 mg) was dissolved in concentrated sulfuric acid (0.7 mL) and stirred at 80° C. for 4 h. The hot solution was added drop-wise to 2.5 mL water in an ice bath. Then, brine (2.5 mL) was added and the mixture heated to reflux for 10 minutes. The solvents were removed under reduced pressure and methanol (10 mL) was added to the residual solid. This inhomogeneous mixture was irradiated in the ultrasonication bath for 3 minutes, then centrifuged at 2500 rpm for 3 minutes and the supernatant was separated off. The same procedure of adding methanol, ultrasonication and centrifugation was repeated two more times. The solvent was evaporated from the combined supernatants, which gave 100 mg of compound 8 as a white solid compound. $^1H$-NMR (400 MHz; $CD_3OD$): 7.63 (s, 4H); 7.62 (s, 4H); 4.02 (bs, 4H); 3.93 (bs, 4H); 2.12 (s, 3H). MS (neg. mode): m/z=225.0110 ($[M-3Na]^{3-}$); calc. 225.0106.

REFERENCES

1. Modified from *Tetrahedron Lett.* 2012, 53, 7, 804-807.
2. Modified from *Synlett,* 2006, 8, 1221-1224.
3. Modified from *Makromol. Chem.* 1979, 180, 2503-2506.

Analytics

The successful outcome of the chemical synthesis was checked by NMR and mass spectrometric analysis of the resulting sulfocalixarene derivative. NMR spectroscopic analysis relied on $^1H$ and $^{13}C$ NMR spectroscopy. The chemical shifts of the individual protons are listed in the text. Mass spectrometry experiments were obtained for both negative and positive ion mode. Based on the expected molecular formula $C_{29}H_{26}O_{13}S_3$ an exact mass of 678.0536 Dalton is to be expected.

Mass spectrometric results were obtained for the sulfocalixarene variant SCA-754 showing both negative and positive ion mode spectra. and m/z peaks calculated. In the negative ion mode only the single sodium adduct was observed, while the positive mode four adduct fragments could be resolved. The experimental MS data clearly show the chemical identity of the compound and unambiguously proved the successful completion of the desired variant molecule.

Mass spectrum:

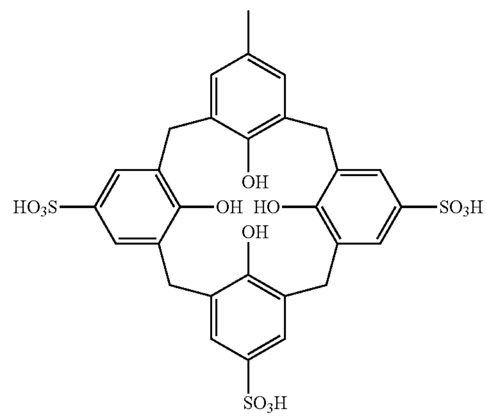

Chemical Formula: $C_{29}H_{26}O_{13}S_3$
Exact Mass: 678.0536

Neg. Mode

Calc.: $M-3H^+/3=225.018$ $M-3H^++N^a+/2=349.02$

Pos. Mode

M+Na=701.05

M+2*Na=723.05

M+3*Na=745.05

M+4*Na=767.05

Example 11 Metabolic Analysis of SCA-744

Metabolic Profiling of Human Neuroblastoma Cells

Human neuroblastoma SH-SY5Y cells were differentiated and treated with 500 μM SCA-744 for 24 h. Cell pellets were extracted using a MeOH:ACN:H2O (2:2:1, v/v) solvent mixture. Untargeted metabolic profiling was performed at the VBCF Metabolomic Unit (www.vbcf.ac.at) employing high-resolution mass spectrometry.

Identification of Key Metabolites

The untarged metabolomic data was analyzed with the Compound Discover Software (version 3.1). The first set of metabolites were analyzed through the internal database of the Vienna Biocenter Core facility. The measured retention time of a compound was compared to the retention time of a standard previously measured. In the case there was a MS2 spectrum available, this was also taken into consideration for identification. The second set of metabolites was annotated with mzCloud (match at least 75%). Identification was based on mzCloud database comparison of measured molecular weight (5 ppm tolerance) and MS2 spectra. The third set of metabolites were annotated via ChemSpider identification (CSID) through molecular weight matching (max. mass tolerance 5 ppm). P-values were calculated by the Compound Discover Software from biological and technical (T1-T2, MS) replicates. For further annotations KEGG, HMDB, BioCyc, Metabolika and PubChem databases were used.

Chemical Group Classification and Enrichment Analysis

The metabolites with a false discovery rate (FDR)<0.05 along with p-values and corresponding fold-change were extracted and subjected to chemical and metabolic network enrichment analysis. Enrichment analysis based on chemical similarity was conducted using ChemRich that is independent of biochemical pathway assignments, but rather utilizes Tanimoto substructure similarity coefficients and medical subject headings ontology to generate non-overlapping clusters of metabolites into distinct chemical classes. Statistical testing was determined by Kolmogorv-Smirnov testing and an FDR adjusted P value of <0.05 was considered significant.

Metabolic Analysis shows that SCA-744 displays a quantifiable pharmacological response, in particular in the form of altered lipid metabolism, down-regulated glycolysis and reduction of NADH, ATP. This leads to the combined interpretation that the adipocyte-inflammation axis[1] is affected by SCA-744. The analysis shows additional response such as a reduction of nucleotide and amino acid biosynthesis.

Comparison of relative metabolite abundance between control and -treated cells was determined by unpaired univariate analysis. Calculated P values were adjusted based on an FDR of 0.05 and filtered by log Fold-Change (log FC) analysis (Table 3). For illustrative purposes the metabolites are annotated on the resulting volcano plot with log FC>1 log FC<−2. A total of 261 annotated metabolites were found with an FDR<0.05. A total of 74 with an absolute log FC>1 to be significantly different in the SCA-744-treated group; represented by an increase in 11 metabolites (Table 3) and a decrease in 63 metabolites (selected metabolites are shown in Table 4).

Up-Regulation:

Only metabolites with a greater than log FC>1 change and an FDR adjusted P value of <0.05 were included in Table 3 (FIG. 10). The most up-regulated metabolite is Lysophosphatidyl (LPI). It is shown that LPI has anti-inflammatory effects in several publication including its receptor GPR55 that has therapeutical potential in the treatment of both inflammatory and neuropathic pain[2,3]. LPI can affect various functions such as cell growth, differentiation and motility in a number of cell-types. Mechanisms of LPI induced relaxation in human pulmonary arteries. It plays an important role in different physiological and pathological contexts, including a role in metabolism and glucose homeostasis. Enrichment analysis supports alternative lipid metabolism and up-regulation of Inositols (Table 3). IL-6 (down-regulated by SCA-744) is a major target of myo-inositol. Inositol has anti-inflammatory effects.

The top eleven up-regulated metabolites include also Hypoxanthine and Inosine highly significant up-regulated. It was shown that Inosine and Hypoxanthine has anti-oxidative and anti-inflammatory effects. For example, Inosine has the ability to prevent overproduction of pro-inflammatory cytokines, while it can enhance the production of the production of the protective IL-10[4].

Table 3 shows further significant up-regulated metabolites and references related to cellular anti-inflammatory and anti-oxidative response, as well as lipid metabolism.

Down-Regulation:

Table 4 (FIG. 10) is showing only selected metabolites since 63 metabolites are highly significantly down-regulated with a log FC<−1.

Enrichment analysis supports alternative lipid metabolism and the down-regulation of sugar acids and sugar phosphates. In this line, FIG. 17 shows mainly metabolites involved in glycolysis. In the metabolic regulation of inflammation, glycolysis plays an important role. Immune cells have developed different metabolic programs to supply them with cellular energy and biomolecules, enabling then to cope with changing and challenging metabolic conditions. Our top down-regulated metabolites include Dihydroxyacetone phosphate (DHAP). DHAP is an essential intermediate in lipid biosynthesis and glycolysis.

Further metabolites are included in the pentose phosphate pathways (PPP), which plays a critical role in inflammation, glucose, and vascular cell damage. It is shown that IL-ß (down-regulated in SCA-744) activates the PPP5. In turn, this leads to an over-activation of NADPH oxidase. Over-activation of PPP is a crucial mechanism for vascular damage and oxidative stress. SCA-744 significant down-regulated Glycolysis and NADH, as well as ATP.

Altered lipid metabolisms, including glycerophospholipids and lysophospholipids, is supported by the enrichment analysis of 135 metabolites (FDR<0.05, absolute log FC>0.5). Enrichment analysis, including 261 metabolites (FDR<0.05, FIG. 2) shows further metabolites in classes such as phosphatidylcholine, phosphatidylserines, phosphatidylethanolamines, and plasmalogens altered, mostly up-regulated. Unsaturated lysophospholipids, as well as unsaturated fatty-acids (FA), are down-regulated in this analysis. This is particularly interesting as unsaturated FA are precursors for inflammatory signaling molecules such as leukotrienes[6]. A low degree of fatty acid unsaturation also leads to lower lipid peroxidation. In inflammation, in particular, the pathogenesis of atherosclerosis, lipoprotein peroxidation plays a crucial role[7].

A further finding of the enrichment analysis is that amino acid metabolism is reduced. Amino acid metabolism is regulated by mTOR which in turn is related to glycerolipid metabolism and autophagy, as well as protein homeostasis.

Autophagy is activated under stress conditions; nutrient starvation, protein homeostasis and pathogen infection and is deregulated in various pathological conditions, including cancer and neurodegenerative diseases. It is generally accepted that ROS induce autophagy and that autophagy, in turn, serves to reduce oxidative damage[18].

Along this line, multiple forms of stress activate autophagy. Degradation of proteins, lipids, carbohydrates and nuclear acids, liberate amino-acids, fatty acids, among other metabolites to the cytoplasm providing internal nutrients for reutilization. Recently, the possible role of autophagy in neurodegenerative diseases and tumor suppression has increasingly been examined, as well its role in inflammation and anti-oxidative stress.

Metabolome Analysis

Up and down-regulated metabolites support that SCA-744 affects the adipocyte-inflammation axis and has anti-inflammatory and anti-oxidative effects, as well as altered lipid metabolism. Besides, Thymine and adenine nucleotides, as well as dipeptides and amino acids, are down-regulated. SCA-744 affects nucleotide and amino acid biosynthesis.

Gene-Ontology Analysis Related to Molecular Function

Gene-ontology analysis related to molecular function shows significant the function of calcium, extra-cellular matrix, glyosaminoglycan, sulfur compound, and heparin binding, FIG. 18.

Example 12: Cytotoxicity of SCA-744 and SCA-754 in Mammalian Cells

In vitro assessment of cytotoxicity of SCA-744 and SCA-754 in mammalian cells. 72 h following SCA-744 and SCA-754-treatment, cell viability was assessed using a standard ATP method, CellTiter-Glo® Luminescent Cell Viability Assay. The effective concentration at 50%, EC50 values were derived from the concentration-effect curves. The EC50 for SCA-744 was 2 mM and 1 mM for SCA-754, FIG. 19.

Example 13: Oxidative Stress Protection of SCA-744 and Variant (SCA-754, Also Referred to as CAL-X)

Figure 19A:
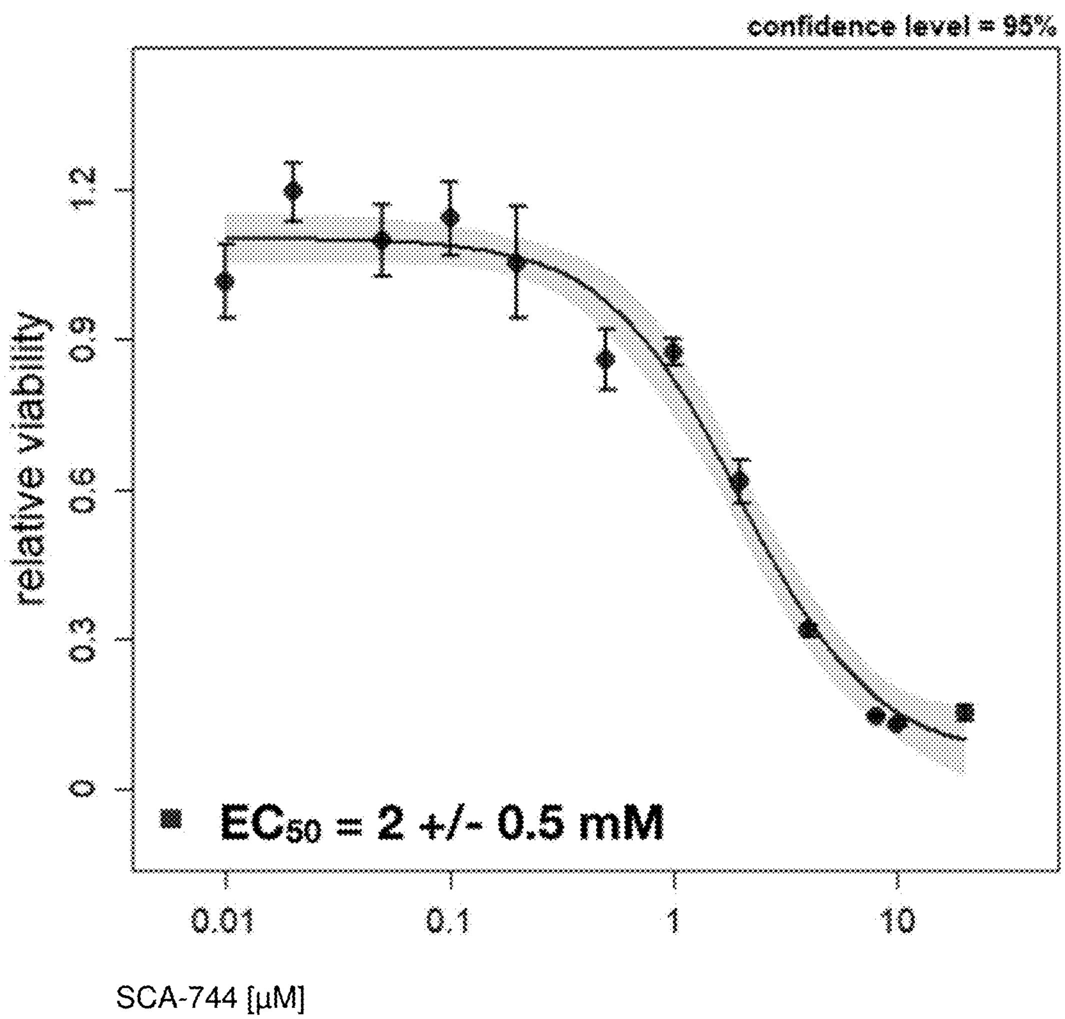
Figure 19B:
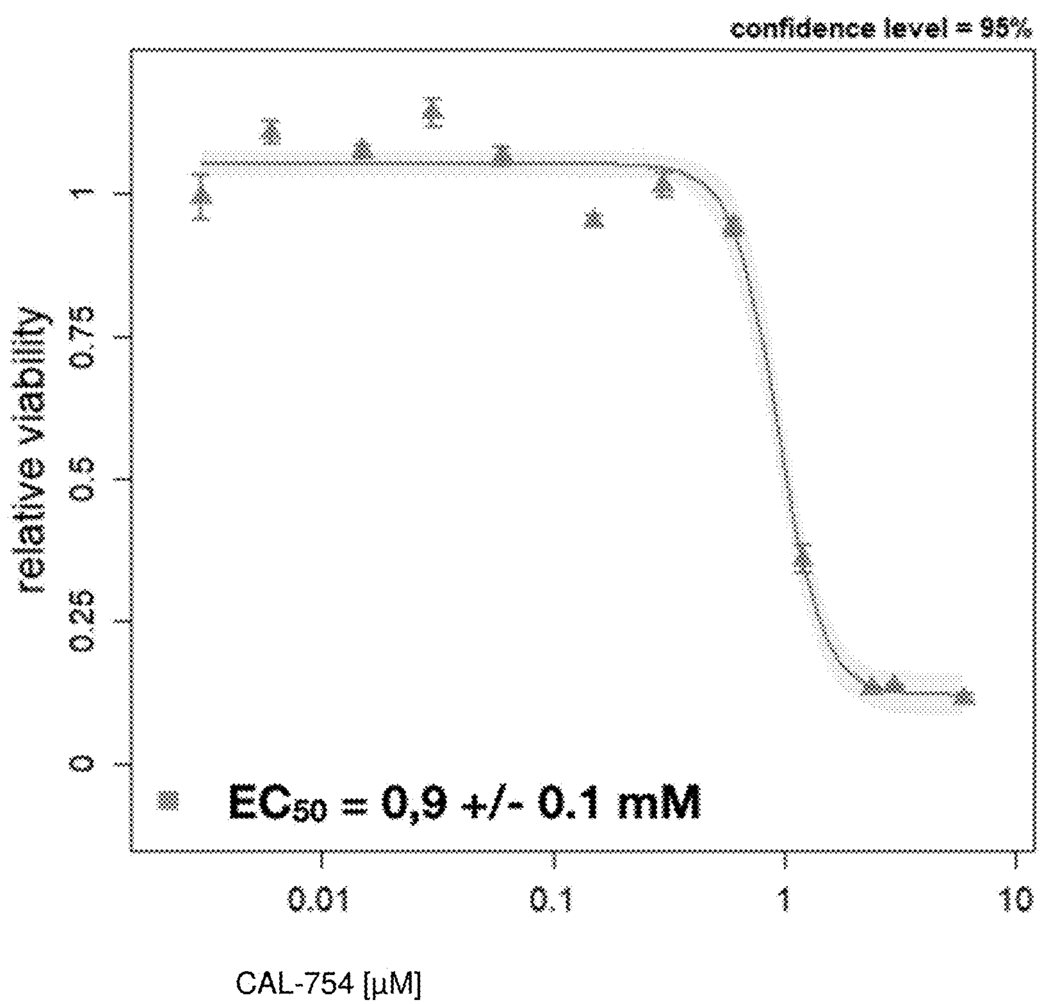
Figure 19C:
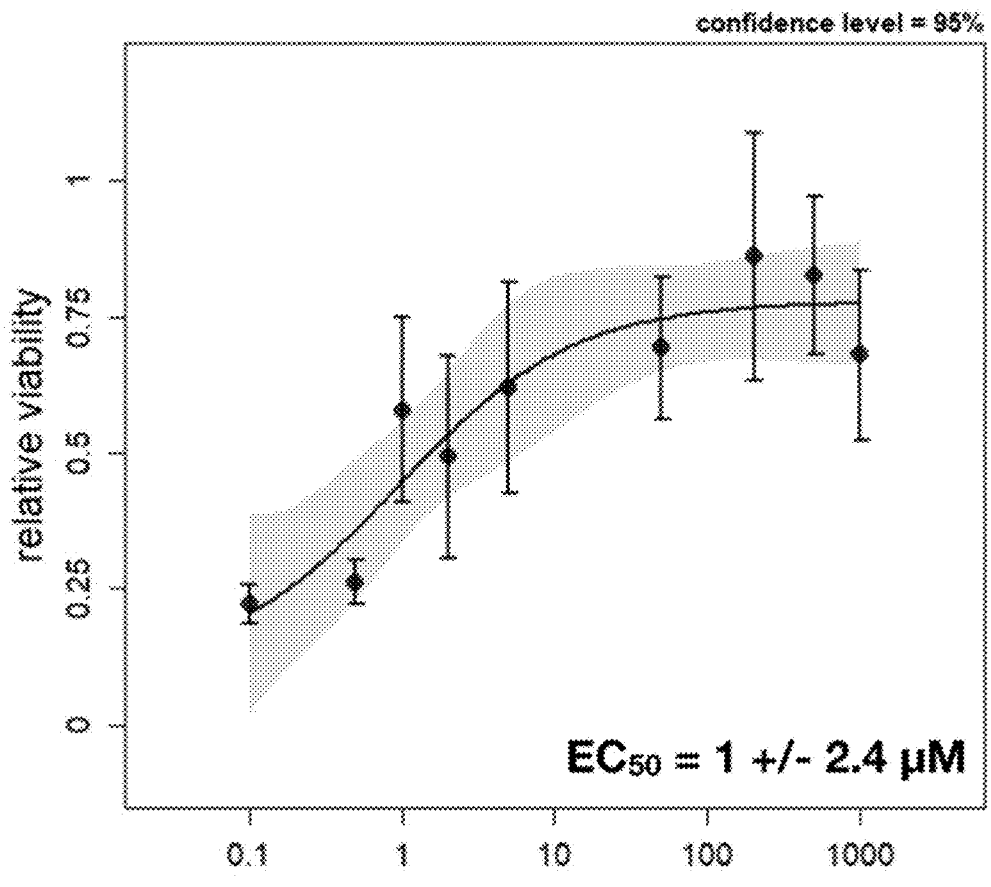
Figure 19D:
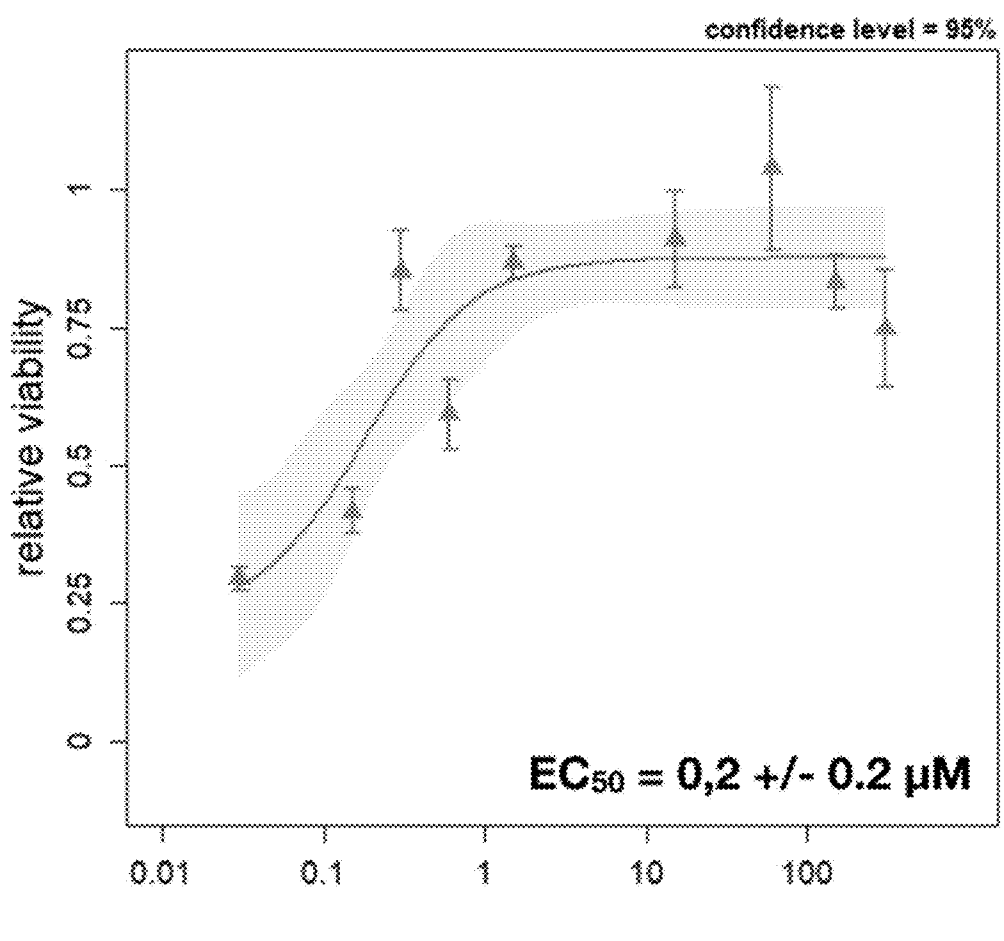

Several in-vivo and in-vitro studies find that MPP+ exerts oxidative stress on cells[22]. MPP+×toxicity is based on its uptake into dopaminergic neurons. MPP+ accumulate into the mitochondria, inhibiting the complex-I leading to ATP depletion, increased reactive oxygen species (ROS) production, and apoptotic cell death[23]. 12 h following MPP+ treatment and SCA-744 and CAL-X incubation, cell viability was assessed using a standard ATP method, CellTiter-Glo® Luminescent Cell Viability Assay. Treatment with 0.1-1000 μM of SCA-744 and CAL-X protected neuroblastoma cells from MPP+ induced apoptosis (FIG. 19C). Interestingly CAL-X MPP+ protection was 5× times more effective [0.2 μM] compared with SCA-744 [1 μM]. Taken together, these results suggest that SCA-744 and CAL-X protects mitochondrial dysfunction induced by oxidative stress, FIG. 19D.

Example 14: SCA-744 Protection on Hydrogen Peroxide $H_2O_2$ Induce Stress in Mammalian Cells Using an incubation time of 24 h, it was sufficient to determine the toxicity and rescue effect of SCA-744 in HELA cells. The effective concentration at 50%, EC50 values were derived from the concentration-effect curves. The EC50 for SCA-744 was 200 nM for a toxic $H_2O_2$ concentration of 50 mM, FIG. 20.

REFERENCES

1. Shah, A., Mehta, N. & Reilly, M. P. Adipose Inflammation, Insulin Resistance, and Cardiovascular Disease. *Jpen-parenter Enter* 32, 638-644 (2008).
2. Kallendrusch, S. et al. The G Protein-Coupled Receptor 55 Ligand 1-a-Lysophosphatidylinositol Exerts Microglia-Dependent Neuroprotection After Excitotoxic Lesion. *Glia* 61, 1822-1831 (2013).
3. Karpińska, O. et al. Mechanisms of 1-alpha-lysophosphatidylinositol-induced relaxation in human pulmonary arteries. *Life Sci* 192, 38-45 (2018).
4. Haskó, G. et al. Inosine Inhibits Inflammatory Cytokine Production by a Posttranscriptional Mechanism and Protects Against Endotoxin-Induced Shock. *J Immunol* 164, 1013-1019 (2000).
5. Peiró, C. et al. Inflammation, glucose, and vascular cell damage: the role of the pentose phosphate pathway. *Cardiovasc Diabetol* 15, 82 (2016).
6. Dennis, E. A. & Norris, P. C. Eicosanoid storm in infection and inflammation. *Nat Rev Immunol* 15, 511-523 (2015).
7. Steinbrecher, P. Role of lipoprotein peroxidation in the pathogenesis of atherosclerosis. *Clin Cardiol* 14, 865-867 (1991).
8. Scherz-Shouval, R. & Elazar, Z. Regulation of autophagy by ROS: physiology and pathology. *Trends Biochem Sci* 36, 30-38 (2011).

REFERENCES (TABLES 3 AND 4)

1. Kallendrusch, S. et al. The G Protein-Coupled Receptor 55 Ligand 1-a-Lysophosphatidylinositol Exerts Microglia-Dependent Neuroprotection After Excitotoxic Lesion. *Glia* 61, 1822-1831 (2013).
2. Karpińska, O. et al. Mechanisms of 1-alpha-lysophosphatidylinositol-induced relaxation in human pulmonary arteries. *Life Sci* 192, 38-45 (2018).
3. Bizzarri, M., Laganà, A. S., Aragona, D. & Unfer, V. Inositol and pulmonary function. Could myo-inositol treatment downregulate inflammation and cytokine release syndrome in SARS-CoV-2*? Eur Rev Med Pharmaco* 24, 3426-3432 (2020).
4. Lee, J. S. et al. Hypoxanthine is a checkpoint stress metabolite in colonic epithelial energy modulation and barrier function. *J Biol Chem* 293, 6039-6051 (2018).
5. Schulte, E. C. et al. Alterations in Lipid and Inositol Metabolisms in Two Dopaminergic Disorders. *Plos One* 11, e0147129 (2016).
6. Vimal, A. & Kumar, A. 1-Asparaginase: a feasible therapeutic molecule for multiple diseases. 3 *Biotech* 8, 278 (2018).
7. Haskó, G., Sitkovsky, M. V. & Szabó, C. Immunomodulatory and neuroprotective effects of inosine. *Trends Pharmacol Sci* 25, 152-157 (2004).
8. Haines, R. J., Pendleton, L. C. & Eichler, D. C. Argininosuccinate synthase: at the center of arginine metabolism. *Int J Biochem Mol Biology* 2, 8-23 (2011).
9. Veen, J. N. van der et al. The critical role of phosphatidylcholine and phosphatidylethanolamine metabolism in health and disease. *Biochimica Et Biophysica Acta Bba—Biomembr* 1859, 1558-1572 (2017).
10. Abuduli, M. et al. Effects of dietary phosphate on glucose and lipid metabolism. *Am J Physiol-endoc M* 310, E526-E538 (2016).
11. Marat, A. L. & Haucke, V. Phosphatidylinositol 3-phosphates—at the interface between cell signalling and membrane traffic. *Embo J* 35, 561-579 (2016).
12. Evaldsson, C., Rydén, I. & Uppugunduri, S. Anti-inflammatory effects of exogenous uridine in an animal model of lung inflammation. *Int Immunopharmacol* 7, 1025-1032 (2007).
13. Jeengar, M. K., Thummuri, D., Magnusson, M., Naidu, V. G. M. & Uppugunduri, S. Uridine Ameliorates Dextran Sulfate Sodium (DSS)-Induced Colitis in Mice. *Sci Rep-uk* 7, 3924 (2017).
14. Rozova, E. V., Mankovskaya, I. N., Belosludtseva, N. V., Khmil, N. V. & Mironova, G. D. Uridine as a protector against hypoxia-induced lung injury. *Sci Rep-uk* 9, 9418 (2019).
15. Gaber, T., Strehl, C. & Buttgereit, F. Metabolic regulation of inflammation. *Nat Rev Rheumatol* 13, 267-279 (2017).
16. Peiró, C. et al. Inflammation, glucose, and vascular cell damage: the role of the pentose phosphate pathway. *Cardiovasc Diabetol* 15, 82 (2016).
17. O'Neill, L. A. J., Kishton, R. J. & Rathmell, J. A guide to immunometabolism for immunologists. *Nat Rev Immunol* 16, 553-565 (2016).

The invention claimed is:

1. A method for treating psoriasis, arthritis, or asthma in a subject in need thereof, comprising administering to said subject an effective amount of a preparation comprising a compound of 5, 11, 17, 23-sulfonato-25, 26, 27, 28-tetrahydroxycalix[4]arene:

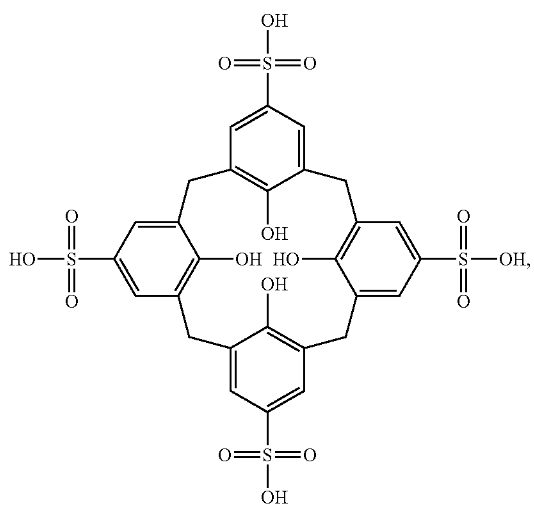 [SMILES: O=S(=O)(O)c1cc2c(O)c(c1)Cc1cc(S(=O)(=O)O)cc(c1O)Cc1cc(S(=O)(=O)O)cc(c1O)Cc1cc(S(=O)(=O)O)cc(c1O)C2]

or a pharmaceutically acceptable salt thereof.

2. The method according to claim 1, wherein the compound acts as a mimic of any one or more of a corticosteroid, heparan sulfate, or heparin.

3. The method according to claim 1, wherein the effective amount of the compound or the pharmaceutically acceptable salt thereof is sufficient to a) reduce expression of one or more proinflammatory cytokines or of one or more proinflammatory genes selected from the group consisting of IKZF1, GDF10, SPOCK3, MMP1, IL-1β, KCNMA1, CCL7, AQP1, ITIH5, ABI3BP, and BMP5;

b) increase expression of one or more anti-oxidative genes;

c) increase expression of any one or more of LDLR, ID3, NQO1, SLCGA2, or DHCR24; or d) modulate the expression of enzymes involved in cholesterol metabolism.

4. The method according to claim 3, wherein the effective amount of the compound or the pharmaceutically acceptable salt thereof is sufficient to a) reduce expression of one or more proinflammatory cytokines selected from the group consisting of IL-1β, IL-6, TNFα; or of one or more proinflammatory genes selected from the group consisting of IKZF1, GDF10, SPOCK3, MMP1, IL-1B, KCNMA1, CCL7, AQP1, ITIH5, ABI3BP, and BMP5;

b) increase expression of one or more anti-oxidative genes selected from the group consisting of CHAC1, SLC7A11, NQO1, EGR1, SGK1, SLC6A9, and DHCR24;

c) increase expression of any one or more of LDLR, ID3, NQO1, SLCGA2, or DHCR24; or d) modulate the expression of enzymes LDLR or DHCR24.

5. The method according to claim 1, wherein the administering to said subject an effective amount of said preparation comprises oral, topical, mucosal or parenteral administration of an effective amount of said preparation.

6. The method according to claim 1, further comprising administering any of a corticosteroid, an anti-TNFα inhibitor, an IL-17 inhibitor, an IL-23/IL-12 inhibitor, a PDE4 inhibitor, Fumaric Acid, a JAK kinase inhibitor, methotrexate, lefunomide, hydroxychloroquine, sulfasalazine, cyclosporin or a dissociative steroid compound.

7. A method of treating psoriasis, arthritis, or asthma in a subject in need thereof, comprising administering to said subject an effective amount of a composition comprising a compound 5, 11, 17, 23-sulfonato-25, 26, 27, 28-tetrahydroxycalix[4]arene:

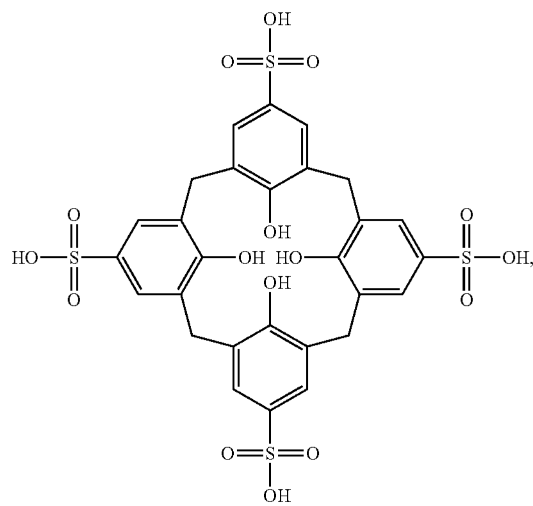 [SMILES: O=S(=O)(O)c1cc2c(O)c(c1)Cc1cc(S(=O)(=O)O)cc(c1O)Cc1cc(S(=O)(=O)O)cc(c1O)Cc1cc(S(=O)(=O)O)cc(c1O)C2]

or a pharmaceutically acceptable salt thereof, and a pharmaceutically acceptable diluent, carrier or excipient.

* * * * *